(12) United States Patent
Gottesfeld et al.

(10) Patent No.: US 6,660,255 B1
(45) Date of Patent: Dec. 9, 2003

(54) INHIBITION OF GENE TRANSCRIPTION BY POLYAMIDE DNA-BINDING LIGANDS

(75) Inventors: Joel M. Gottesfeld, Del Mar, CA (US); Peter B. Dervan, San Marino, CA (US); Donald E. Mosier, Del Mar, CA (US); Eldon E. Baird, Lexington, SC (US)

(73) Assignees: California Institute of Technology, Pasadena, CA (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/367,513

(22) PCT Filed: Feb. 11, 1998

(86) PCT No.: PCT/US98/02444
§ 371 (c)(1),
(2), (4) Date: Apr. 25, 2000

(87) PCT Pub. No.: WO98/35702
PCT Pub. Date: Aug. 20, 1998

Related U.S. Application Data

(60) Provisional application No. 60/038,384, filed on Feb. 14, 1997, provisional application No. 60/038,394, filed on Feb. 14, 1997, provisional application No. 60/056,048, filed on Sep. 2, 1997, and provisional application No. 60/058,338, filed on Sep. 10, 1997.

(51) Int. Cl.⁷ ............................................. A61K 31/785
(52) U.S. Cl. ....................................................... 424/78.36
(58) Field of Search ...................................... 424/78.36

(56) References Cited

U.S. PATENT DOCUMENTS 5,578,444 A    11/1996   Edwards et al.

FOREIGN PATENT DOCUMENTS

WO    WO-94/14980    *   7/1994

OTHER PUBLICATIONS

Trauger et al. Recognition of DNA by designed ligands at subnanomolar concentrations, Nature vol. 382, pp. 559–561, Aug. 8, 1996.*

Weisz, Angew. Chem. Int. Ed. Engl. (1997) 36(23): 2592–2594.

Wu, H., et al., "Building Zinc Fingers by Selection: Toward a Therapeutic Application," Proc. Natl. Acad. Sci. U.S.A., (1995) 92:344–8.

Yamada, O., et al., "A Chimeric Human Immunodeficiency Virus Type 1 (HIV–1) Minimal Rev Response Element–Ribozyme Molecule Exhibits Dual Antiviral Function and Inhibits Cell–Cell Transmission of HIV–1," J. Virol., (1996) 70(3):1596–1601.

Zhou, C., et al., "Inhibition of HIV–1 in Human T–Lymphocytes by Retrovirally Transduced Anti–tat and Rev Hammerhead Ribozymes," Gene, (1994) 149:33–9.

1, Science (1988) 239:910–3.

Sheridan, P.L., "Activation of the HIV–1 Enhancer by the LEF–1 HMG Protein on Nucleosome–Assembled DNA In Vitro," Genes Dev., (1995) 9:2090–104.

Smith, D.R., et al., "Domains of the Positive Transcription Factor Specific for the Xenopus 5S RNA Gene," Cell, (1984) 37:645–52.

Stutz, F., et al., "Oocyte and Somatic Tyrosine tRNA Genes in *Xenopus Laevis*," Genes Dev., (1989) 3:1190–8.

Sullenger, B.A., et al., "Overexpression of TAR Sequences Renders Cell Resistant to Human Immunodeficiency Virus Replication," Cell, (1990) 63:601–8.

Sun, L.Q., et al., "Resistance to Human Immunodeficiency Virus Type 1 Infection Conferred by Transduction of Human Peripheral Blood Lymphocytes with Ribozyme, Antisense, or Polymeric Trans–Activation Response Element Constructs," Proc. Natl. Acad. Sci. U.S.A., (1995) 92:7272–6.

Swalley, S.E., et al., "A Pyrrole–Imidazole Polyamide Motif for Recognition of Eleven Base Pair Sequences in the Minor Groove of DNA," Chem Eur. J., (1997) 3(10):1600–7.

Thiesen, H.J., "From Repression Domains to Designer Zinc Finger Proteins: A Novel Strategy of Intracellular Immunization Against HIV," Gene Expr., (1996) 5:229–43.

Trauger, J. W., et al., "Extension of Sequence–Specific Recognition in the Minor Groove of DNA by Pyrole–Imidazole Polyamides to 9–13 Base Pairs," J. Am. Chem. Soc., (1996) 118(26):6160–6.

Verrijzer, C.P., et al., "TAFs Mediate Transcriptional Activation and Promoter Selectivity," TIBS (1996) 21:338–41.

Wade, W. S., et al., "Design of Peptides that Bind in the Minor Groove of DNA at 5'–(A,T)G(A,T)C(A,T)–3' Sequences by a Dimeric Side–by–Side Motif," J. Am. Chem. Soc., (1992) 114:8783–94.

Waterman, M.L., et al., "Purification of TCF–1α, A T–Cell–Specific Transcription Factor that Activates the T–Cell Receptor CαGene Enhancer in a Context–Dependent Manner," New Biologist, (1990) 2(7):621–36.

Wei, X., et al., "Viral Dynamics in Human Immunodeficiency Virus Type 1 Infection," Nature (1995) 373:117–122.

Weiss, M.J., et al., "The Structure of Antibiotic T–1384. Synthesis of the Degradation Fragments," J. Am. Chem. Soc., (1957) 79: 1266.

White, S., et al., "Effects of the A•T/T•A Degeneracy of Pyrrole–Imidazole Polyamide Recognition in the Minor Groove of DNA," Biochemistry, (1996) 35:12532–7.

(List continued on next page.)

Primary Examiner—Russell Travers
Assistant Examiner—Shengjun Wang
(74) Attorney, Agent, or Firm—Morrison & Foerster LLP

(57) ABSTRACT

The invention provides polyamides suitable for modulating cellular or viral gene expression by binding to an identified target DNA sequence adjacent to the binding site of a minor groove transcription factor protein. The polyamides of the present invention are useful for the treatment of a human infected with a virus such as HIV-1. The polyamides of the present invention are also useful for the treatment of conditions, such as cancers, that result from the expression or over-expression of cellular genes, particularly oncogenes.

7 Claims, 38 Drawing Sheets

OTHER PUBLICATIONS

White, S., et al., "On the Pairing Rules for Recognition in the Minor Groove of DNA by Pyrrole–Imidazole Polamides," Chem. & Biol., (1997) 4(8):569–578.

Immunodeficiency Virus Type 1 Infection of Lymphocytes and Monocytes, Proc. Natl. Acad. Sci. U.S.A., (1991) 88:5011–5.

Lisziewicz, J., et al., Antisense Oligodeoxynucleotide Phosphorothioate Complementary to Gag mRNA Blocks Replication of Human Immunodeficiency Virus Type 1 in Human Peripheral Blood Cells, Proc. Natl. Acad. Sci. U.S.A., (1994) 91: 7942–6.

Liu, C., et al., "Actinomycin D Binds Strongly and Dissociates Slowly at the dGpdC Site with Flanking T/T Mismatches," Biochemistry, (1996) 35:16346–53.

Love, J. J., et al., "Structural Basis for DNA Bending by the Architectural Transcription Factor LEF–1," Nature, (1995) 376:791–5.

Maldonado, E., et al., "News on Initiation and Elongation of Transcription by RNA Polymerase II," Current Opinion in Cell Biology, (1995) 7:352–61.

Mosier, D. E., et al., "Human Immunodeficiency Virus Infection of Human–PBL–SCID Mice," Science (1991) 251:791–4.

Mosier, D. E., et al., Rapid Loss of CD4$^+$ T Cells in Human–PBL– SCID Mice by Noncytopathic HIV Isolates, Science (1993) 260:689–92.

Mrksich, M., et al., "Antiparallel Side–by–Side Dimeric Motif for Sequence–Specific Recognition in the Minor Groove of DNA by the Designed Peptide 1–Methylimidazole–2–Carboxamide Netropsin," Proc. Natl. Acad. Sci. U.S.A., (1992) 89:7586–90.

Oakley, M.G., et al., "Evidence that a Minor Groove–Binding Peptide and a Major Groove–Binding Protein Can Simultaneously Occupy a Common Site on DNA," Biochemistry, (1992) 31:10969–75.

Olsen, H.S., "Contribution of the TATA Motif to Tat–Mediated Transcriptional Activation of Human Immunodeficiency Virus Gene Expression," J. Virol., (1992) 66(9):5594–7.

Pelton, J.G., et al., "Structural Characterization of a 2:1 Distamycin A•d(CGCAAATTGGC) Complex by two–Dimensional NMR," Proc. Natl. Acad. Sci. U.S.A., (1989) 86:5723–7.

Perkins, N.D., et al., "An Interaction between the DNA–Binding Domains of Re1A(p65) and Sp1 Mediates Human Immunodeficiency Virus Gene Activation," Mol. Cell. Biol., (1994) 14(10):6570–83.

Peterson, R.C., et al., "Characterization of Two Xenopus Somatic 5S DNAs and One Minor Oocyte–Specific 5S DNA," Cell, (1980) 20:131–41.

Raillard, S.A., et al., "Targeting Sites within HIV–1 cDNA with a DNA–Cleaving Ribozyme," Biochemistry, (1996) 35:11693–701.

Roeder, R.G., "The Role of General Initiation Factors in Transcription by RNA Polymerase II," TIBS (1996) 21:327–34.

Sadaie, M.R., et al., Site–Directed Mutagenesis of Two Trans–Regulatory Genes (tat–III, trs) of HIV–.

Choo, Y., et al., "In Vivo Repression by a Site–Specific DNA–Binding Protein Designed Against an Oncogenic Sequence," Nature, (1994) 372:642–5.

Cirisano, F.D., et al., "The Role of the HER–2/neu Oncogene in Gynecologic Cancers," J. Soc. Gynecol. Investig., (1996) 3(3):99–105.

Clark, S. J., et al., "High Titers of Cytopathic Virus in Plasma of Patients with Symptomatic Primary HIV–1 Infection," N. Engl. J. Med., (1991) 324(14):954–60.

Clemens, K. R., et al., "Relative Contributions of the Zinc Fingers of Transcription Factor IIIA to the Energetics of DNA Binding," J. Mol. Biol., (1994) 244:23–5.

Dignam, J. D., et al., Eukaryotic Gene Transcription with Purified Components, Meth. Enzymol., (1983) 101:582–98.

Finnegan, L. P., "A Peppy Response to PEPI Results," Nature Med., (1995) 1(3):205–6.

Frech, K., et al., "Common Modular Structure of Lentivirus LTRs," Virology (1996) 224:256–67.

Giese, K., et al., "Assembly and Function of a TCRα Enhancer Complex is Dependent on LEF–1–Induced DNA Bending and Multiple Protein–Protein Interactions," Genes Dev., (1995) 9:995–1008.

Hartl, P., et al., "Mitotic Repression of Transcription In Vitro," J. Cell Biol., (1993) 120(3):613–24.

Hélène, C., "Reading the Minor Groove," Nature (1998) 391:436–8.

Ho, D. D., et al., "Rapid Turnover of Plasma Virions and CD4 Lymphocytes in HIV_1 Infection," Nature (1995) 373: 123–6.

Ho, S.N., et al., "Specific Inhibition of Formation of Transcription Complexes by a Calicheamicin Oligosaccharide: A Paradigm for the Development of Transcriptional Antagonists," Proc. Natl. Acad. Sci., (1994) 91:9203–7.

Hobbs, M.V., et al., "Patterns of Cytokine Gene Expression by CD4$^+$ T Cells from Young and Old Mice," J. Immunol., (1993) 150(8):3602–14.

Iverson, B.L., et al., "Adenine Specific DNA Chemical Sequencing Reaction," Nucleic Acids Res., (1987) 15(19):7823–30.

Jones, K.A., et al., "Control of RNA Initiation and Elongation at the HIV–1 Promoter," Annu. Rev. Biochem., (1994) 63:717–743.

Kim, J.Y.H., et al., "Replication of Type 1 Human Immunodeficiency Viruses Containing Linker Substitution Mutations in the –201 to –130 Region of the Long Terminal Repeat," J. Virol., (1993) 67(3):1658–62.

Klotman, M.E., et al., Kinetics of Expression of Multiply Spliced RNA in Early Human.

Bachelerie, F., et al., "HIV Enhancer Activity Perpetuated by NF–kB Induction of Infection of Monocytes," Nature, (1991) 350:709–12.

Baird, E. E., et al., "Solid Phase Synthesis of Polyamides Containing Imidazole and Pyrrole Amino Acids," J. Am. Chem. Soc., (1996) 118:6141–6.

Berkhout, B., et al., "Functional Roles for the TATA Promoter and Enhancers in Basal and Tat–Induced Expression of the Human Immunodeficiency Virus Type 1 Long Terminal Repeat," J. Virol., (1992) 66 (1):139–49.

Bevec, D., et al., "Inhibition of Human Immunodeficiency Virus Type 1 Replication in Human T Cells by Retroviral–Mediated Gene Transfer of a Dominant–Negative Rev Trans–Activator," Proc. Natl. Acad. Sci. U.S.A., (1992) 89:9870–4.

Bigey, P., et al., "Cleavage of Double–Stranded DNA by 'Metalloporphyrin–Linker–Oligonucleotide' Molecules: Influence of the Linker," Nucleic Acids Res., (1995) 23(19):3894–900.

Bordier, B., et al., "Sequence–Specific Inhibition of Human Immunodeficiency Virus (HIV) Reverse Transcription by Antisense Oligonucleotides: Comparative Study in Cell–Free Assay and in HIV–Infected Cells," Proc. Natl. Acad. Sci. U.S.A., (1995) 92: 9383–7.

Bouziane, M., et al., "Alternate Strand DNA Triple Helix–Mediated Inhibition of HIV–1 U5 Long Terminal Repeat Integration In Vitro," J. Biol. Chem., (1996) 271(17):10359–64.

Burley, S.K., et al., "Biochemistry and Structural Biology of Transcription Factor IID (TFIID)," Ann. Rev. Biochem., (1996) 65:769–99.

Chen, J., et al., "Assembly of Recombinant TFIID Reveals Differential Coactivator Requirements for Distinct Transcriptional Activators," Cell, (1994) 79: 93–105.

Cheng–Mayer, C., et al., "Biological Features of HIV–1 that Correlate with Virulence in the Host," Science (1988) 240:80–2.

Cheng–Mayer, C., et al., "Isolates of Human Immunodeficiency Virus Type 1 from the Brain May Constitute a Special Group of the AIDS Virus," Proc. Natl. Acad. Sci. U.S.A., (1989) 86:8575–.

* cited by examiner

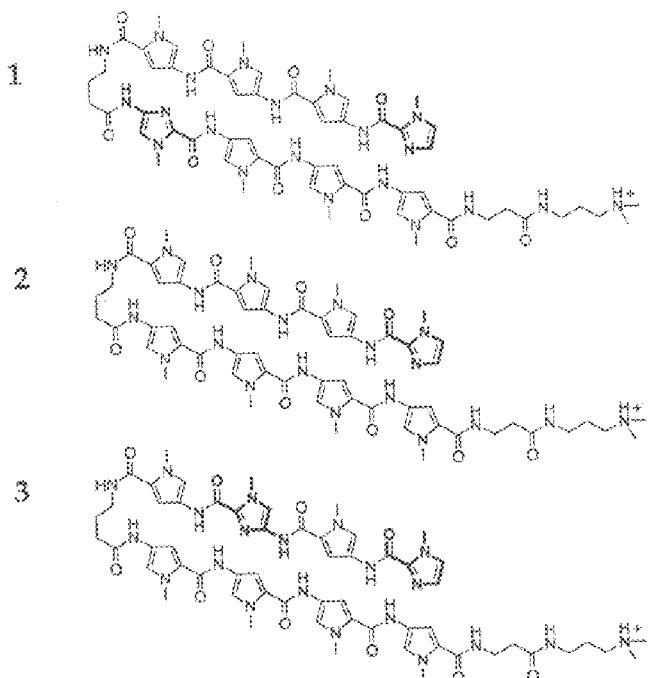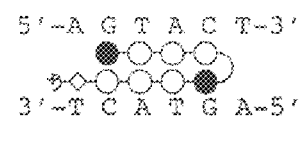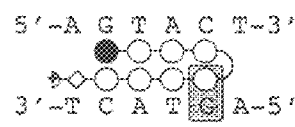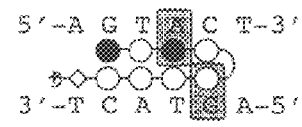
FIG. 1B      FIG. 1C

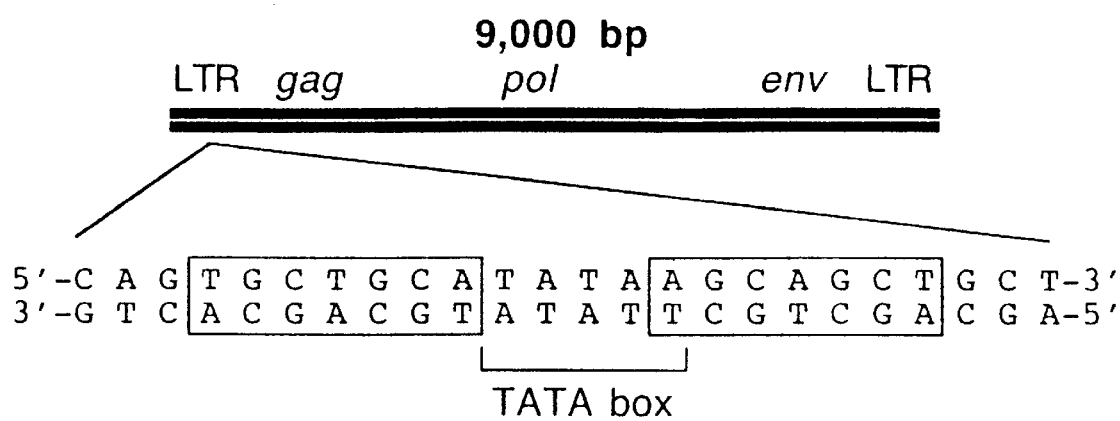
FIG. 5A
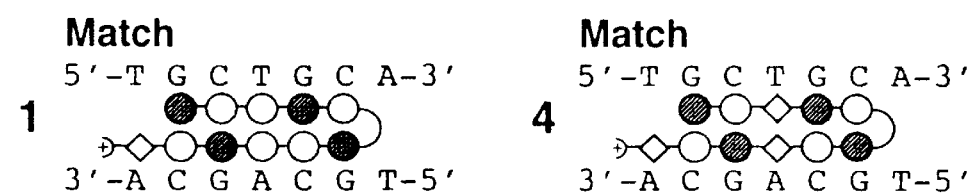
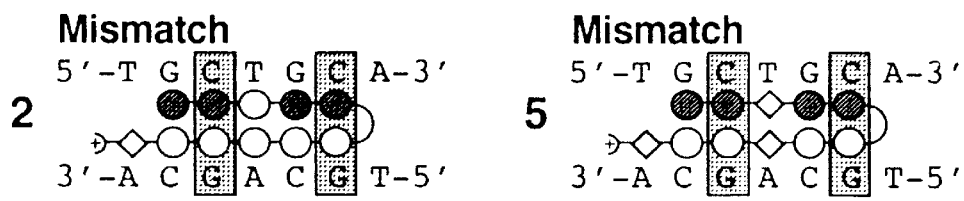
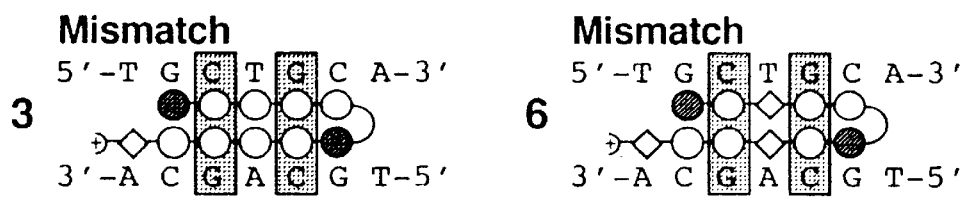
FIG. 5B

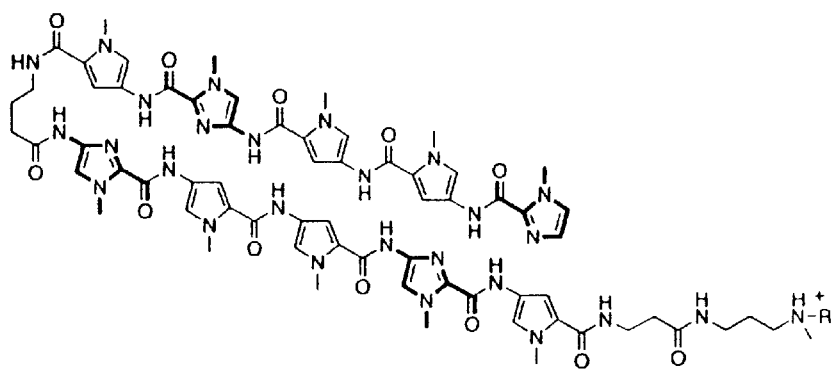
1 ImPyPyImPy-γ-ImPyPyImPy-β-Dp
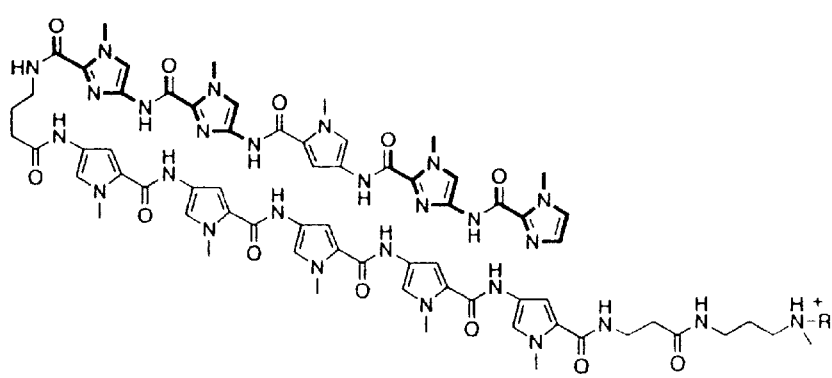
2 ImImPyImIm-γ-PyPyPyPyPy-β-Dp
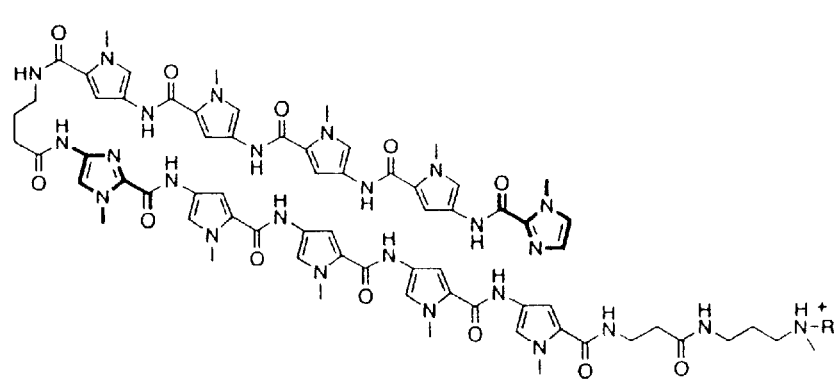
3 ImPyPyPyPy-γ-ImPyPyPyPy-β-Dp
3-E·Fe$^{II}$ ImPyPyPyPy-γ-ImPyPyPyPy-β-Dp-EDTA·Fe$^{II}$
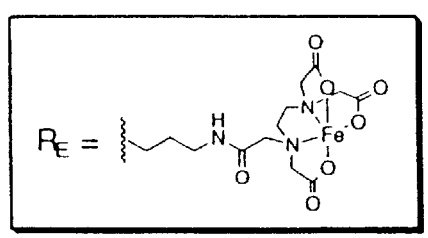
FIG. 6A

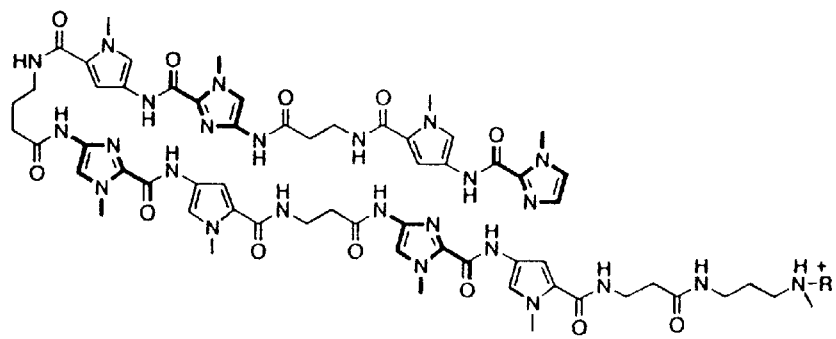
4 (R=H) ImPy-β-ImPy-γ-ImPy-β-ImPy-β-Dp
4-E·Fe$^{II}$ (R=R$_E$) ImPy-β-ImPy-γ-ImPy-β-ImPy-β-Dp-EDTA·Fe$^{II}$
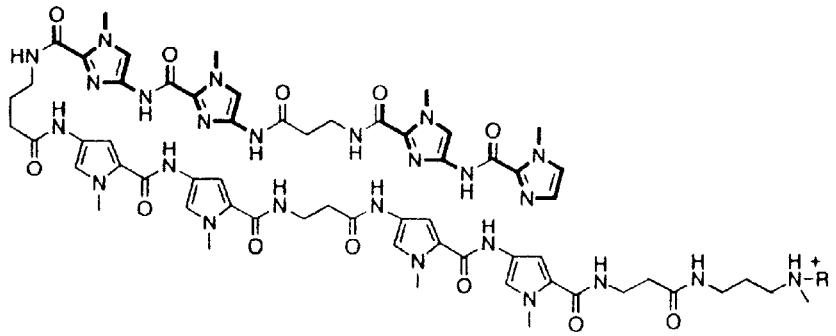
5 (R=H) ImIm-β-ImIm-γ-PyPy-β-PyPy-β-Dp
5-E·Fe$^{II}$ (R=R$_E$) ImIm-β-ImIm-γ-PyPy-β-PyPy-β-Dp-EDTA·Fe$^{II}$
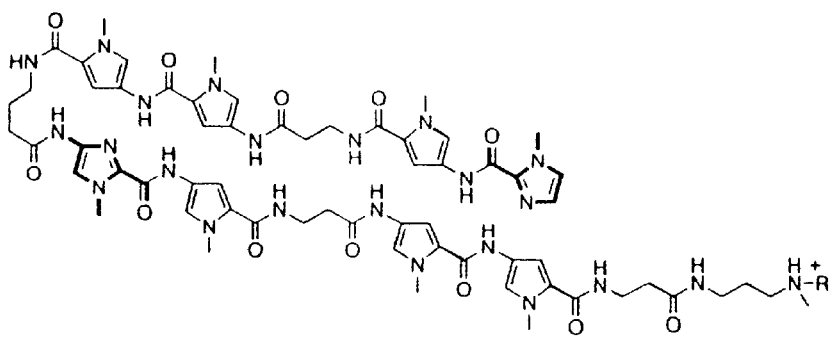
6 ImPy-β-PyPy-γ-ImPy-β-PyPy-β-Dp
6-E·Fe$^{II}$ ImPy-β-PyPy-γ-ImPy-β-PyPy-β-Dp-EDTA·Fe$^{II}$
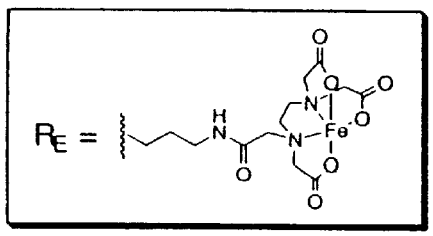
FIG. 6B

1 nM 4
1 nM 5
1 nM 6
1 nM 3
FIG. 10A
1 nM 4-E
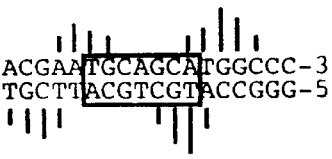
1 nM 5-E
5 nM 6-E
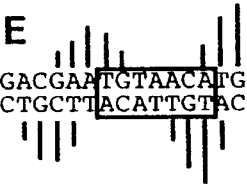
1 nM 3-E
FIG. 10B

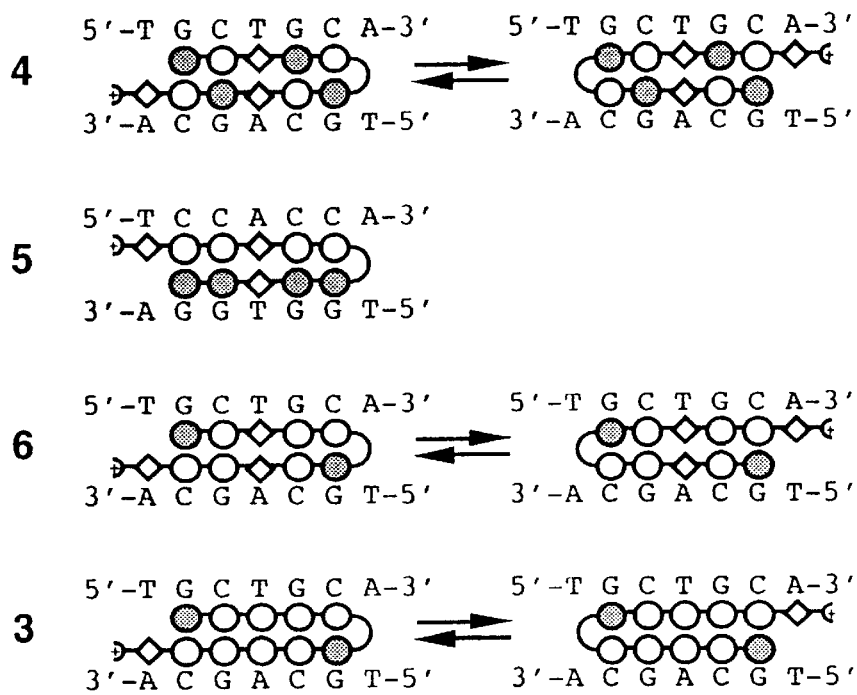

FIG. 10C

```
       -200       -190       -180       -170       -160       -150       -140
         |          |          |          |          |          |          |
5'-GTTAGAGTGGAGGTTTGACAGCCGCCTAGCATTTCATCACGTGGCCCGAGAGCTGCATCCGGAGTA
                                                 USF              ETS-1

-130       -120       -110       -100        -90        -80
         |          |          |          |          |          |
  CTACAAAGACTGCTGACATCGAGCTTTCTACAAGGGACTTTCCGCTGGGGACTTTCCAGGGAGGCG
     LEF-1                                  NF-κB      NF-κB         Sp 1

-70        -60        -50        -40        -30        -20        -10
         |          |          |          |          |          |          |
  TGGCCTGGGCGGGACTGGGGAGTGGCGTCCCTCAGATGCTGCATATAAGCAGCTGCTTTTTGCCTG
         SP-1       SP-1                           TFIID

+1        +10        +20        +30        +40        +50
         |          |          |          |          |          |
  TACTGGGTCTCTCTGGTTAGACCAGATCTGAGCCTGGGAGCTCTCTGGCTAACTAGGGAACCC-3'
```

FIG. 11

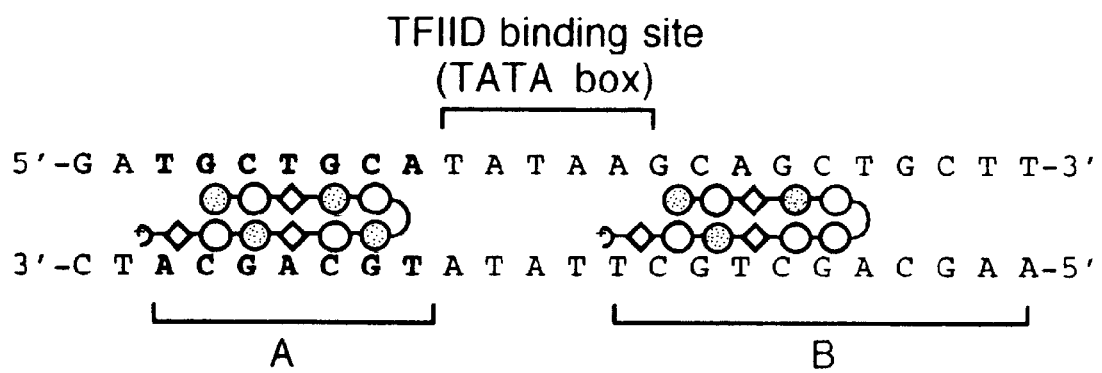
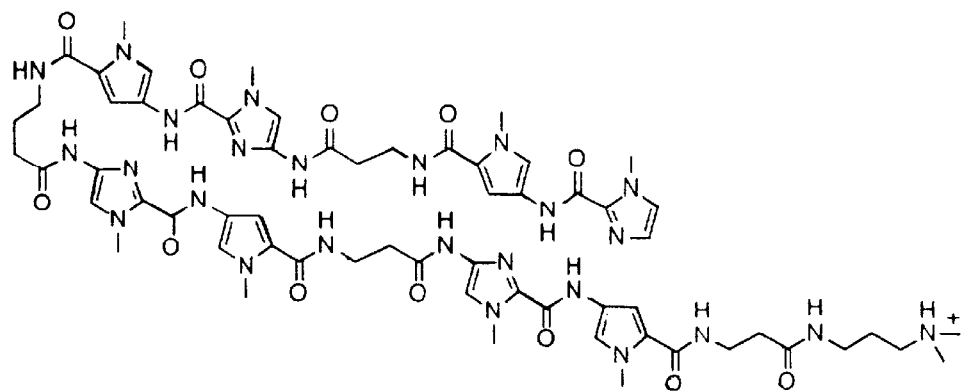
HIV-1 ImPy-β-ImPy-γ-ImPy-β-ImPy-β-Dp
FIG. 14B

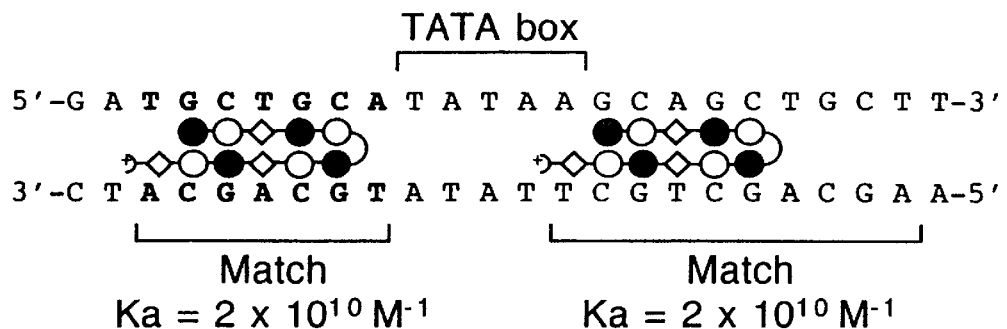
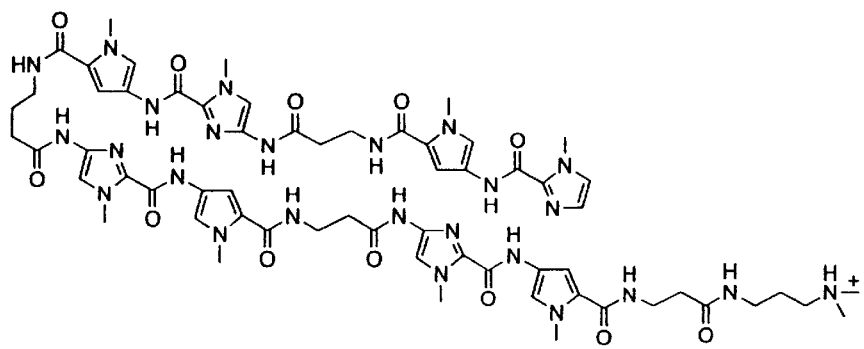
HIV-1 ImPy-β-ImPy-γ-ImPy-β-ImPy-β-Dp
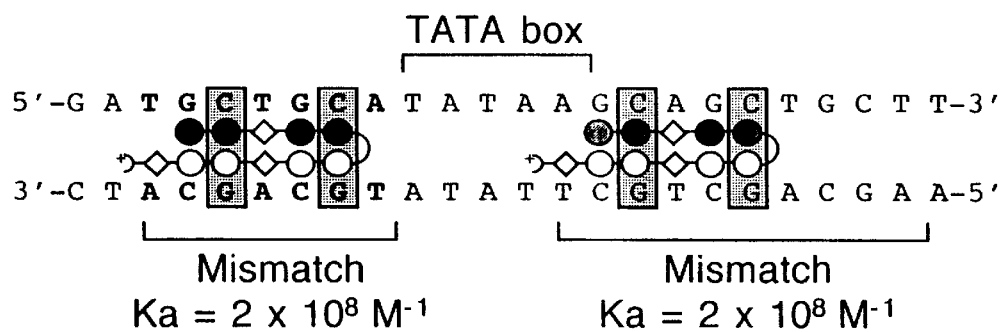
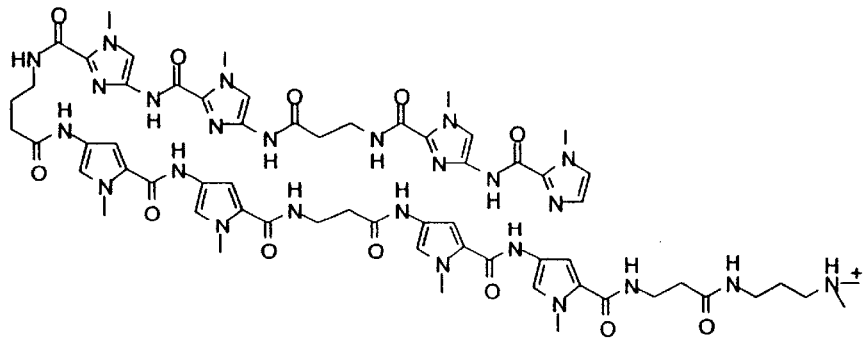
HIV-2 ImIm-β-ImIm-γ-PyPy-β-PyPy-β-Dp
FIG. 16

1a) ImPy-β-ImPy-γ-ImPy-β-ImPy-β-Dp - 7 bp
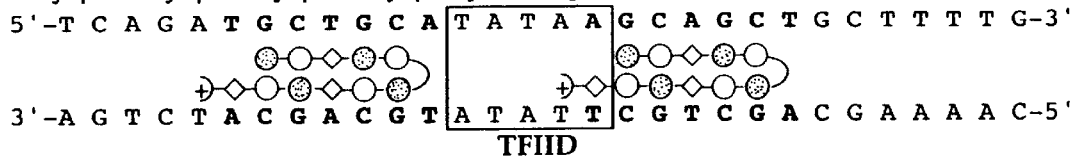
1b) ImPy-β-PyPyPyPy-β-ImPy-β-Dp - 12 bp
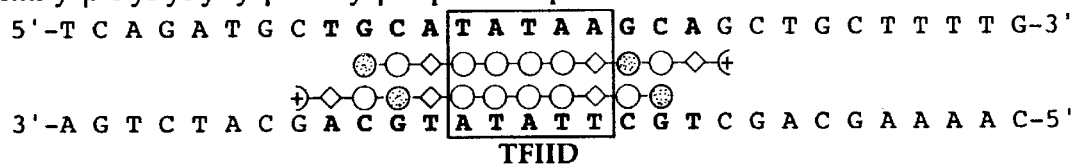
1c) ImPy-β-ImPy-β-PyPyPyPy-β-ImPy-β-ImPy-β-Dp - 16 bp
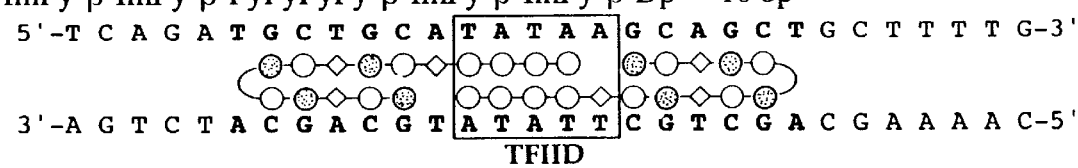
2a): ImPyPyPy-γ-ImPyPyPy-β-Dp - 6 bp
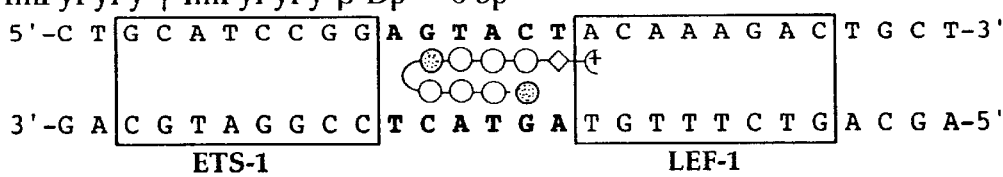
2b): ImPy-β-ImPyPyPy-γ-ImPyPyPy-β-PyPy-β-Dp - 9 bp
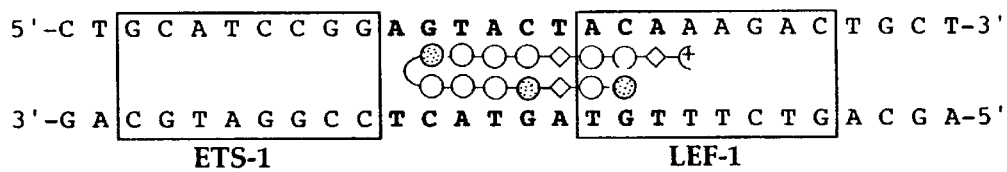
FIG. 17

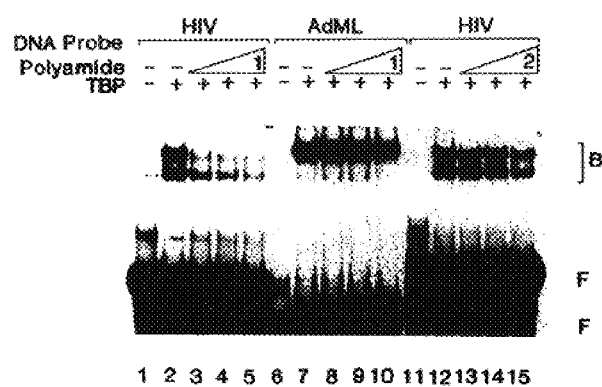
FIG. 19B
FIG. 19A

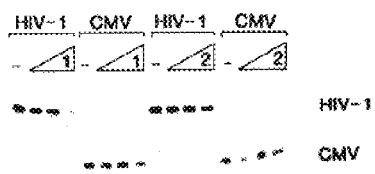
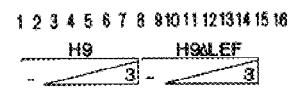
FIG. 21A
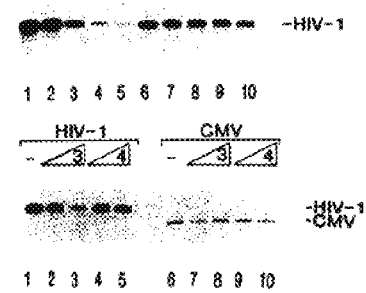
FIG. 21C
FIG. 21D
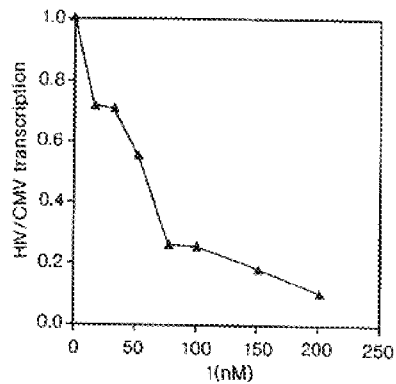
FIG. 21B

| gene | sequence flanking TATA region |
|---|---|
| HIV-1 | 5'-TGCTGCATATAAGCAGCTGCT-3' |
| IL-5 | 5'-AGCTGCcTGAGAGTTTTTAACCATTACA-3' |
| IL-2 | 5'-TTAACAGTATAAATTGCAtCTC-3' |
| IL-13 | 5'-TTGGGCCTATAAAAGCTGCcAC-3' |
| TNF-alpha | 5'-AGGGACATATAAAGGCAGTTG-3' |
| TGF-beta | 5'-GGGGCTGTATTTAAGGACACCG-3' |
| GM-CSF | 5'-CTCTGTGTATTTAAGAGCTCTT-3' |
| TNF-beta | 5'-CCTCCTCTATAAAGGGACCTGA-3' |

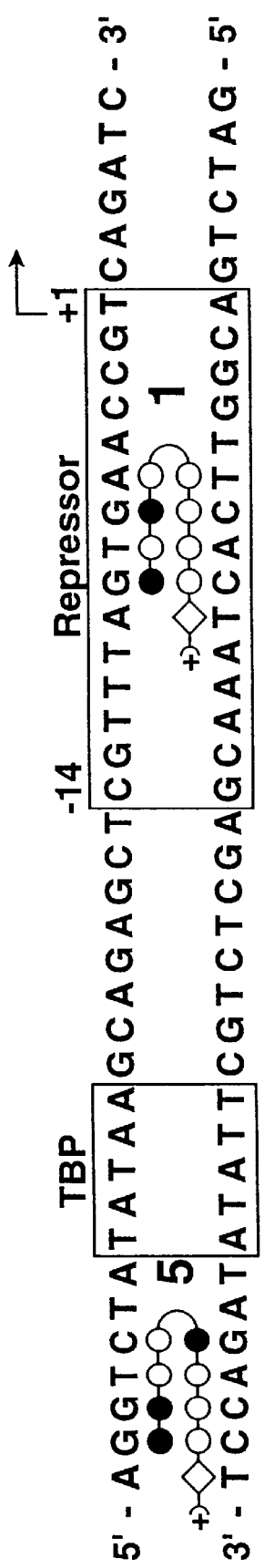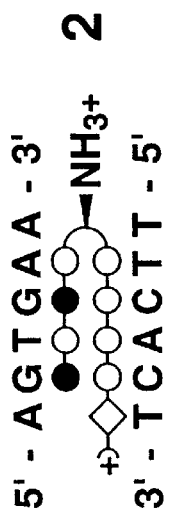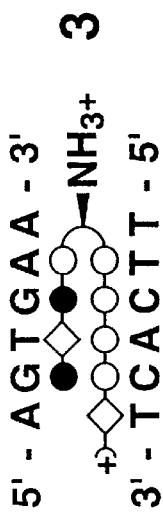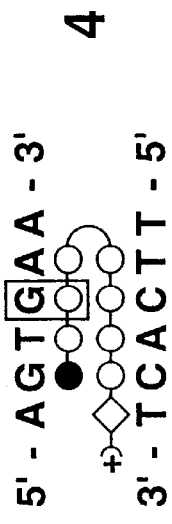
FIG. 29

SEQUENCE LISTING

<160> NUMBER OF SEQ ID NOS: 16

<210> SEQ ID NO 1
<211> LENGTH: 68
<212> TYPE: DNA
<213> ORGANISM: Artificial Sequence
<220> FEATURE:
<223> OTHER INFORMATION: Complementary oligonucleotide

<400> SEQUENCE: 1
ccggcttaag ttcgtgggcc atgctgcatt cgtgggccat ggtggattcg tgggccatgt    60
tacattcg                                                             68

<210> SEQ ID NO 2
<211> LENGTH: 68
<212> TYPE: DNA
<213> ORGANISM: Artificial Sequence
<220> FEATURE:
<223> OTHER INFORMATION: Complementary oligonucleotide

<400> SEQUENCE: 2
tcgacgaatg taacatggcc cacgaatcca ccatggccca cgaatgcagc atggcccacg    60
aacttaag                                                             68

<210> SEQ ID NO 3
<211> LENGTH: 18
<212> TYPE: DNA
<213> ORGANISM: HIV

<400> SEQUENCE: 3
tgctgcatat aagcagct                                                  18

<210> SEQ ID NO 4
<211> LENGTH: 13
<212> TYPE: DNA
<213> ORGANISM: HIV

<400> SEQUENCE: 4

-continued catataagca gct                                        13

<210> SEQ ID NO 5
<211> LENGTH: 13
<212> TYPE: DNA
<213> ORGANISM: Artificial Sequence
<220> FEATURE:
<223> OTHER INFORMATION: TATA region (mutant)

<400> SEQUENCE: 5
catataagta ctt                                        13

<210> SEQ ID NO 6
<211> LENGTH: 18
<212> TYPE: DNA
<213> ORGANISM: HIV

<400> SEQUENCE: 6
tgctgcataa aagcagcc                                   18

<210> SEQ ID NO 7
<211> LENGTH: 50
<212> TYPE: DNA
<213> ORGANISM: HIV

<400> SEQUENCE: 7
cgtccctcag atgctgcata taagcagctg cttttttgcct gtactgggtc    50

<210> SEQ ID NO 8
<211> LENGTH: 26
<212> TYPE: DNA
<213> ORGANISM: Adenovirus

<400> SEQUENCE: 8
gatcgggggc tataaaaggg ggtggg                          26

<210> SEQ ID NO 9
<211> LENGTH: 19
<212> TYPE: DNA
<213> ORGANISM: Adenovirus

<400> SEQUENCE: 9
gggggctata aaggggggt                                  19

<210> SEQ ID NO 10
<211> LENGTH: 18
<212> TYPE: DNA
<213> ORGANISM: CMV

<400> SEQUENCE: 10
gaggtctata taagcaga                                   18

<210> SEQ ID NO 11
<211> LENGTH: 11
<212> TYPE: DNA
<213> ORGANISM: Artificial Sequence
<220> FEATURE:
<223> OTHER INFORMATION: Artificial TATA

<400> SEQUENCE: 11
tataagtact t                                          11

<210> SEQ ID NO 12
<211> LENGTH: 12

```
<212> TYPE: DNA
<213> ORGANISM: HIV

<400> SEQUENCE: 12
tgctgcatat aa                                                          12

<210> SEQ ID NO 13
<211> LENGTH: 11
<212> TYPE: DNA
<213> ORGANISM: HIV

<400> SEQUENCE: 13
tataagcagc t                                                           11

<210> SEQ ID NO 14
<211> LENGTH: 10
<212> TYPE: DNA
<213> ORGANISM: CMV

<400> SEQUENCE: 14
aggtctataa                                                             10

<210> SEQ ID NO 15
<211> LENGTH: 11
<212> TYPE: DNA
<213> ORGANISM: Homo sapiens

<400> SEQUENCE: 15
tataagaatg a                                                           11

<210> SEQ ID NO 16
<211> LENGTH: 12
<212> TYPE: DNA
<213> ORGANISM: Unknown
<220> FEATURE:
<223> OTHER INFORMATION: 2-1 distamycin A-d

<400> SEQUENCE: 16
cgcaaatttg gc                                                          12
```

INHIBITION OF GENE TRANSCRIPTION BY POLYAMIDE DNA-BINDING LIGANDS

CROSS REFERENCE TO RELATED APPLICATIONS

This application is a 371 of PCT/US548/02444, filed Feb. 11, 1998, which is a continuation in part of U.S. provisional applications Ser. No. 60/038,384, filed Feb. 14, 1997, Ser. No. 60/038,394, filed Feb. 14, 1997, Ser. No. 60/056,048, filed Sep. 2, 1997, and Ser. No. 60/058,338, filed Sep. 10, 1997, which are incorporated by reference, U.S. application Ser. No. 08/853,525, filed Apr. 8, 1997, now U.S. Pat. No. 5,998,140, and PCT/US97/12733, filed Jul. 21, 1997.

The U.S. Government has certain rights in this invention pursuant to Grant Nos. GM 26453, 27681, 47530 and AI 29182 awarded by the National Institute of Health.

BACKGROUND OF THE INVENTION

Field of the Invention

This invention relates to polyamides that bind to predetermined sequences in the minor groove of double stranded DNA that are useful for diagnosis and treatment of diseases associated with gene transcription. This invention is related to modulation of cellular or viral gene expression required for maintenance and replication of pathogens in infectious disease, such as HIV-1 and CMV. This invention is also related to modulation of cellular gene expression in non-infectious disease conditions, such as cancers involving oncogenes, e.g., her-2/neu.

Gene Therapy Approaches for HIV:

Considerable effort has been expended over the past decade to devise methods to interfere with HIV-1 gene expression in living cells in the hope that therapeutic strategies will come from these studies (recently reviewed in Kohn, D. B. and N. Sarver, Gene therapy for HIV-1 infection, in *Antiviral Chemotherapy*, J. Mills, P. A. Volberding, and L. Corey, Editors. 1996, Plenum Press: New York. p. 421–427.). One approach includes interference with the translation of messenger RNA into protein by the introduction of antisense oligonucleotides into lymphoid cells, as discussed in Kohn, D. B. and N. Sarver, Gene therapy for HIV-1 infection, in *Antiviral Chemotherapy*, J. Mills, P. A. Volberding, and L. Corey, Editors. 1996, Plenum Press: New York. p. 421–427; Bordier, B., et al., *Proc. Natl. Acad. Sci. U.S.A.*, 92: 9383–9387 (1995) and Lisziewicz, J., et al., *Proc. Natl. Acad. Sci. U.S.A.*, 91: 7942–7946 (1994).

Another approach involves ribozyme-mediated destruction of specific regions of HIV-1 mRNA. See Sun, L. Q., et al., *Proc. Natl. Acad. Sci. U.S.A.*, 92: 7272–7276 (1995); Yamada, O., et al., *J. Virol.*, 70: 1596–1601 (1996) and Zhou, C., et al., *Gene*, 149: 33–39 (1994). Decoy molecules, corresponding to HIV-1 RNA domains that bind regulatory proteins required for the HIV-1 life cycle (TAR RNA which binds Tat or the Rev-response element) have been used as inhibitors of HIV-1 replication (Sullenger, B. A., et al., *Cell*, 63: 601–608 (1990). In addition, trans-dominant mutant versions of these regulatory proteins, introduced into cells with retroviral expression vectors, have been shown to inhibit HIV-1 replication (Bevec, D., et al., *Proc. Natl. Acad. Sci. U.S.A.*, 89: 9870–9874, 1992.).

Other approaches for direct inhibition of gene transcription, including designed or selected zinc finger peptides that recognize pre-determined DNA sequences, are described in Wu, H., et al., *Proc. Natl. Acad. Sci. U.S.A.*, 92: 344–348 (1995) and Thiesen, H.-J., *Gene Expr.*, 5: 229–243. (1996). DNA-cleaving ribozymes have also been tried (Raillard, S. A. and G. F. Joyce, *Biochemistry*, 35: 11693–11701(1996)). Triple helix-forming oligonucleotides have been used to block HIV-1 integration: Bouziane, M., et al., *J. Biol. Chem.*, 271: 10359–10364 (1996). Triple helix-forming oligonucleotides have also been used specifically cleave HIV-1 DNA with a metalloporphyrin group attached to the oligonucleotide, as described by Bigey, P., G. Pratviel, and B. Meunier, *Nucleic Acids Res.*, 23: 3894–3900 (1995). Additionally, the DNA-binding calicheamicin oligosaccharides have the potential for use in anti-HIV-1 therapy but have not as yet been applied to this disease. See Ho, S. N., et al., *Proc. Natl. Acad. Sci.*, 91: 9203–9307 (1994) and Liu, C., et al., *Biochemistry*, 93: 940–944 (1996).

For any gene therapy approach to be successful, several criteria must be met by the therapeutic agent: First, tile agent must not possess any general cell toxicity and should not elicit an immune response. Second, the agent must be cell-permeable or amenable to viral delivery and, in the case of the DNA-binding agents, the therapeutic agent must transit to the nucleus and bind the target sequence with high affinity and specificity in the context of cellular chromatin. Third, binding of the agent to its DNA or RNA target sequence must interfere with gene transcription or protein translation.

Each of the potential approaches listed above has its own unique advantages and limitations. For example, while nucleic acid-based approaches (antisense, decoy and triple helix-forming oligonucleotides and ribozymes) have the potential for sequence selectivity and can effectively inhibit transcription or translation in vitro, these molecules suffer from poor cell permeability and other delivery systems, such as retroviral vectors in the case of the ribozymes (Zhou, C., et al., 1994) or liposomes or other delivery strategies in the case of antisense or triple helix oligonucleotides, must be used for effective gene inhibition (reviewed in Kohn & Sarver, 1996). Similarly, zinc finger peptides must be introduced via a gene therapy approach with an appropriate viral expression vector since these peptides cannot directly enter cells. See Choo, Y., et al., *Nature*, 372: 642–645 (1994).

One additional problem with gene therapy approaches is that they must be performed on lymphoid cells ex vivo and, once an "HIV-protected" cell population is established, these cells must then be introduced into the patient.

In contrast to gene therapy approaches, HIV protease inhibitors taken in combination with standard anti-retroviral agents (AZT) have recently shown success in clinical trials. Wei, X. et al., *Nature*, 373: 117–122 (1995); Ho, D. D. et al., *Nature*, 373: 123–126 (1995).

The key to the anti-HIV properties of these drugs is that they strike at two separate phases of the virus life cycle, limiting the ability of spontaneous mutations to result in inhibitor-resistant strains of the virus. Small molecule inhibitors of HIV-1 RNA transcription which would target a third phase of the virus life cycle would be highly desirable. Cell-permeable sequence-specific DNA-binding ligands would circumvent the problems associated with other forms of gene therapy and could compliment the protease inhibitor-anti-retroviral agent cocktail approach mentioned above. The calicheamicin oligosaccharides satisfy some of the requirements for a therapeutic agent; these molecules are sufficiently hydrophobic to pass through cell membranes but these molecules possess severely limited sequence specificity (4 base pairs) and bind DNA with very low affinities (100 μM or higher required for inhibition of protein-DNA interactions. See Ho, S. N., et al., *Proc. Natl. Acad. Sci.*, 91: 9203–9307 (1994) and Liu, C., et al., *Biochemistry*, 93: 940–944 (1996)).

Thus, new classes of cell-permeable molecules that possess higher degrees of DNA sequence specificity and affinity are needed for the treatment of AIDS and other infectious diseases. We describe below the successful development of a new class of highly specific designed small molecule ligands with great potential for inhibition of HIV-1 gene transcription.

The HIV-1 Enhancer and Promoter:

A recent review has summarized our current knowledge of the protein factors required for the control of RNA initiation and elongation by RNA polymerase II at the HIV-1 promoter (Jones, K. A. and B. M. Peterlin. 1994. Control of RNA initiation and elongation at the HIV-1 promoter. *Annu. Rev. Biochem.*, 63: 717–743). Thus only those aspects of HIV-1 transcription that relate to transcription inhibition are discussed herein. For HIV, the template for synthesis of both new viral RNA and messenger RNA (for viral protein synthesis) is the integrated provirus, the product of reverse transcription of the viral RNA in the infected cell. HIV-1 utilizes the transcription machinery of the host cell but encodes its own trans-activators, Tat and Rev, that are responsible for RNA elongation and utilization. The HIV-1 promoter is located in the U3 region of the leftward (5') long terminal repeat (see FIG. 11 below, taken from Jones and Peterlin, 1994). The core promoter and enhancer elements span a region of approximately 250 base pairs and include TATA and initiator elements and the binding sites for the following cellular transcription factors: Sp1, NF-κB, LEF-1, Ets-1 and USF. Sequences upstream of the NF-κB sites contribute only marginally to HIV-1 promoter activity either in vitro or in transfected cell lymphoid cell lines. Waterman, M. L. and K. A. Jones, *New Biologist*, 2: 621–636 (1990). However, these upstream sequences, and presumably the protein factors which bind these upstream sequences, are important for viral replication, and hence promoter activity, in peripheral blood lymphocytes and in some T cell lines. Kim, J., et al., *J. Virol*, 67: 1658–1662 (1993).

Two of the binding sites in the upstream region correspond to recognition sites for activator proteins that are lymphoid cell specific (or highly enriched in T cells) and are shared with the promoter of the T cell receptor (TCRα) gene: these are the Ets-1 and LEF-1 transcription factors. The essential role of the upstream region has recently been reproduced in vitro with a chromatin reconstitution assay (Sheridan, P. L., et al., *Genes Dev.*, 9: 2090–2104 (1995)).

Packaging of the HIV-1 promoter into nucleosomes strongly repressed transcription, but this repression could be relieved by pre-incubation of the template with the HIV-1 enhancer-binding proteins, LEF-1 and Ets-1. LEF-1 and Ets-1 thus apparently act in concert to prevent nucleosome-mediated repression in vivo. Inhibition of formation of this complex by small molecule inhibitors could well represent a viable target for HIV-1 gene therapy. LEF-1 is a member of the HMG family of proteins and binds DNA as a monomer. DNA binding is in the minor groove and results in a large distortion of the DNA helix (unwinding and bending) (Love, J. J., et al., *Nature*, 376: 791–795 (1995)).

In addition to acting as an architectural transcription factor, LEF-1 possesses a strong trans-activation domain which can function when artificiality transferred to other DNA-binding proteins (Giese, K., et al., *Genes Dev.*, 9: 995–1008 (1995)). This region of the HIV-1 enhancer might thus prove to be an effective target for inhibition of viral transcription and hence virus replication.

The HIV-1 promoter also contains tandem binding sites for NF-κB, a factor that is strongly induced by HIV infection (Bachelerie, F., et al. *Nature*, 350: 709–712 (1991)) and multiple binding sites for the general transcription factor Sp1. The mechanisms of NF-κB activation have been reviewed by Jones and Peterlin, 1994. Important for this discussion, NF-κB has been shown to contact both Sp1 and the TBP subunit of the basal transcription factor TFIID. Perkins, N. D., et al., *Mol. Cell. Biol.*, 14: 6570–6583 (1994). Additionally, Sp1 has been shown to interact with the TAF110 subunit of TFIID (110 kDa TBP-associated factor) (Chen, J. L., et al., *Cell*, 79: 93–105, 1994). It is the binding of TFIID via the TBP interaction with the TATA element that nucleates the assembly of the complete RNA polymerase II transcription complex (reviewed in Maldonado, E. and D. Reinberg, *Current Opinion in Cell Biology*, 7: 352–361. 1995). Thus NF-κB may function through recruitment of Sp1 and TFIID to the HIV-1 promotor via these protein-protein interactions. Thus blocking the NF-κB-DNA and/or Sp1-DNA interaction is another potential target for HIV therapy. Since these factors, and especially Sp1 and TFIID, are utilized by a wide range of cellular genes, the binding sites for these factors would not be good targets for HIV-specific inhibition (or any gene-specific inhibition). However, the sequences adjacent to these sites, that are unique to HIV-1 proviral DNA, are excellent candidate targets for the design of inhibitory DNA ligands (see below).

Polyamide DNA-binding Ligands:

Simple rules have been developed to rationally determine the sequence-specificity of minor-groove-binding polyamidecontaining N-methylimidazole and N-methylpyrrole amino acids. These synthetic pyrrole-imidazole polyamides bind DNA with excellent specificity and very high affinities, even exceeding the affinities of many sequence-specific transcription factors (Trauger et al., *Nature*, 382: 559–561, 1996). An Im/Py pair distinguishes G.C from C.G and both of these from A.T or T.A base pairs. Wade, W. S., et al. describes the design of peptides that bind in the minor groove of DNA at 5'-WGWCW-3' sequences (where W is either A or T, and a W.W pairs is an A.T or a T.A base pairs by a dimeric side-by-side motif. *J Am. Chem. Soc.* 114, 8783–8794 (1992); Mrksich, M. et al. describes antiparallel side-by-side motif for sequence specific-recognition in the minor groove of DNA by the designed peptide 1-methylimidazole-2-carboxamidenetropsin. *Proc. Natl. Acad. Sci. USA* 89, 7586–7590 (1992); Trauger, J. W., et al., describes the recognition of DNA by designed ligands at subnanomolar concentrations. *Nature* 382, 559–561 (1996). A Py/Py pair specifies A.T from G.C but does not distinguish A.T from T.A. Pelton, J. G. & Wemmer, D.E. describes the structural characterization of a 2-1 distamycin A-d (CGCAAATTTGGC)(SEQ ID NO:16) complex by two-dimensional NMR. *Proc. Natl. Acad Sci. USA* 86, 5723–5727 (1989); White, S., et al. *Biochemistry* 35, 12532–12537 (1996) describes the effects of the A.T/T.A degeneracy of pyrrole-imidazole polyamide recognition in the minor groove of DNA, the pairing rules for recognition in the minor groove of DNA by pyrrole-imidazole polyamides, and also describes the 5'-3' N-C orientation preference for polyamide binding in the minor groove.

It has been found that a new aromatic amino acid, 3-hydroxy-N-methylpyrrole (Hp) when incorporated into a polyamide and paired opposite Py, provides the means to discriminate A.T from T.A. White S., et al., *Nature* 391 436–438 (1998). Unexpectedly, the replacement of a single hydrogen atom on the pyrrole with a hydroxy group in a Hp/Py pair regulates the affinity and the specificity of a polyamide by an order of magnitude. Utilizing Hp together with Py and Im in polyamides to form four aromatic amino acid pairs (Im/Py, Py/Im, Hp/Py, and Py/Hp) provides a code to distinguish all four Watson-Crick base pairs in the minor groove of DNA.

The preferred corresponding designed specific polyamides resulting from this invention are of the form

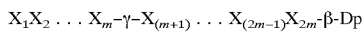

$X_1X_2 \ldots X_m\text{-}\gamma\text{-}X_{(m+1)} \ldots X_{(2m-1)}X_{2m}\text{-}\beta\text{-Dp}$ wherein $X_1$, $X_2$, $X_m$, $X_{(m+1)}$, $X_{(2m-1)}$, and $X_{2m}$ are carboxamide residues forming carboxamide binding pairs $X_1/X_{2m}$, $X_2/X_{(2m-1)}$, $X_m/X_{(m+1)}$, and $\gamma$ is $\gamma$-aminobuytic acid or 2,4 diaminobutyric acid and Dp is dimethylaminopropylamide, and where carboxamide binding pair $X_1/X_{2m}$ corresponds to base pair $N_1.N'_1$, carboxamide binding pair $X_2/X_{(2m-1)}$ corresponds to base pair $N_2.N'_2$, carboxamide binding pair $X_m/X_{(m+1)}$ corresponds to base pair $N_m.N'_m$.

In general, the specific polyamide DNA-binding ligands were designed by using a method that comprises the steps of identifying the target DNA sequence 5'-$WN_1N_2 \ldots N_mW$-3'; representing the identified sequence as 5'-Wab . . . xW-3', wherein a is a first nucleotide to be bound by the $X_1$ carboxamide residue, b is a second nucleotide to be bound by the $X_2$ carboxamide residue, and x is the corresponding nucleotide to be bound by the $X_m$ carboxamide residue; defining a as A, G, C, or T to correspond to the first nucleotide to be bound by a carboxamide residue in the identified six base pair sequence.

Carboxamide residues were selected sequentially as follows: Im was selected as the $X_1$ carboxamide residue and Py as the $X_{2m}$ carboxamide residue if a was G. Py was selected as the $X_1$ carboxamide residue and Im as the $X_2$m carboxamide residue if a was C. Hp was selected as the $X_1$ carboxamide residue and Py as the $X_{2m}$ carboxamide residue if a was T. Py was selected as the $X_1$ carboxamide residue and Hp as the $X_{2m}$ carboxamide residue if a was A.

The remaining carboxamide residues were selected in the same fashion. Im was selected as the $X_2$ carboxamide residue and Py as the $X_{2m-1}$ carboxamide residue if b was G. Py was selected as the $X_2$ carboxamide residue and Im as the $X_{2m-1}$ carboxamide residue if b was C. Hp was selected as the $X_2$ carboxamide residue and Py as the $X_{2m-1}$ carboxamide residue if b was T. Py was selected as the $X_2$ carboxamide residue and Hp as the $X_{2m-1}$ carboxamide residue if b was A.

The selection of carboxamide residues was continued through m iterations. In the last iteration, Im was selected as the $X_m$ carboxamide residue and Py as the $X_{m+1}$ carboxamide residue if x was G. Py was selected as the $X_m$ carboxamide residue and Im as the $X_{m+1}$ carboxamide residue if x was C. Hp was selected as the $X_m$ carboxamide residue and Py as the $X_{m+1}$ carboxamide residue if x was T. Py was selected as the $X_m$ carboxamide residue and Hp as the $X_{m+1}$ carboxamide residue if x was A.

In one preferred embodiment, the polyamide includes at least four consecutive carboxamide pairs for binding to at least four base pairs in a duplex DNA sequence. In another preferred embodiment, the polyamide includes at least five consecutive carboxamide pairs for binding to at least five base pairs in a duplex DNA sequence. In yet another preferred embodiment, the polyamide includes at least six consecutive carboxamide pairs for binding to at least six base pairs in a duplex DNA sequence. In one preferred embodiment, the improved polyamides have four carboxamide binding pairs that will distinguish A.T, T.A, C.G and G.C base pairs in the minor groove of a duplex DNA sequence.

DNA target sequence recognition thus depends on a code of side-by-carboxamide residue pairings in the minor groove of double stranded DNA. These compounds represent the only class of synthetic small molecules that can bind predetermined DNA sequences with affinities and specificities comparable to DNA-binding proteins.

SUMMARY OF THE INVENTION

This invention provides specific polyamides that are useful for modulating the expression of a cellular or viral gene by binding to predetermined target sequences adjacent to the binding site of a transcription factor protein in the minor groove of double stranded DNA. Suitable cellular genes include both eukaryotic and prokaryotic genes. The cellular gene can be present in the original native cells, in cells transfected or transformed with a recombinant DNA construct comprising the cellular gene or in an in vitro in a cell-free system. The viral gene can be present in a cell or in an in vitro in a cell-free system.

The polyamides of the present invention can act as specific inhibitors of gene transcription in vivo or in vitro as therapeutic agents in disease conditions related to the transcription of at least one cellular or viral gene. Studies with three accepted model systems have shown that polyamides do interfere with the binding of sequence-specific minor groove transcription factor proteins as well as with components of the basal transcription machinery and thus block transcription of target genes.

Hereinafter, N-methylpyrrole carboxamide may be referred to as "Py", N-methylimidazole carboxamide may be referred to as "Im", 3-hydroxy-N-methylpyrrole carboxamide may be referred to as "Hp", γ-aminobutyric acid may referred to as "γ", β-alanine may be referred to as "β", glycine may be referred to as "G", dimethylaminopropylamide may be referred to as "Dp", and ethylenediaminetetraacetic acid may be referred to as "EDTA".

The invention encompasses polyamides having γ-aminobutyric acid or a substituted γ-aminobutyric acid to form a hairpin with a member of each carboxamide pairing on each side of it. Preferably the substituted γ-aminobutyric acid is a chiral substituted γ-aminobutyric acid such as (R)-2,4-diaminobutyric acid. In addition, the polyamides may contain an aliphatic amino acid residue, preferably a β-alanine residue, in place of a Hp or Py carboxamide. The β-alanine residue is represented in formulas as β. The β-alanine residue becomes a member of a carboxamide binding pair. The invention further includes the substitution as a β/β binding pair for non-Im containing binding pair. Thus, binding pairs in addition to the Im/Py, Py/Im, Hp/Py and Py/Hp are Im/β, β/Im, Py/β, β/Py, Hp/β, β/Hp, and β/β.

The polyamides of the invention can have additional moieties attached covalently to the polyamide. Preferably the additional moieties are attached as substituents at the amino terminus of the polyamide, the carboxy terminus of the polyamide, or at a chiral (R)-2,4-diaminobutyric acid residue. Suitable additional moieties include a detectable labeling group such as a dye, biotin or a hapten. Other suitable additional moieties are DNA reactive moieties that provide for sequence specific cleavage of the duplex DNA.

A central aspect of the present invention is the use of unique or rare sequences adjacent to the binding sites for common transcription factors as the target sequences for the design of polyamides. It has been found that (1) sequences adjacent to the binding sites for required transcription factors are unique to the genes under study and are not found in other genes in the current nucleic acid data bases; (2)

polyamides targeted to these sequences are effective inhibitors of protein-DNA interactions; (3) such polyamides are inhibitors of transcription factor-dependent gene transcription in vitro; and (4) the polyamides are cell permeable agents and have been shown to inhibit transcription of target genes in human cells in culture.

Most importantly, several designed polyamides have been shown to inhibit transcription of specific genes in vivo and thus these compounds must be both cell permeable and once inside the cell they must be able to transit the nuclear envelope and bind their target sites within chromatin (Gottesfeld, J. M., et al., Nature, 387: 202–205, 1997). These results demonstrate that designed pyrrole-imidazole polyamides are useful in the treatment of diseases, particularly viral diseases, including AIDS, as well as many other diseases for which specific candidate gene targets have been identified.

The present invention provides specific polyamides which inhibit the transcription of DNA upstream or downstream of transcriptional factors such as the 5S RNA gene transcriptional factor TFIIIA, the minor groove-binding protein TATA-box binding protein (TBP), Ets-1 and the lymphold enhancer factor LEF-1 protein. These polyamides act as gene-specific inhibitors of transcription since these polyamides are selective for the sequences flanking these protein binding sites that are, in turn, gene-specific. The polyamides are useful as therapeutics for the treatment of cancer as well as for the treatment of diseases caused by viruses and other pathogens (such as bacterial, fungal, etc.)

The present invention provides a composition comprising a transcription inhibiting amount of at least one polyamide chosen from the group consisting of ImPyPyPy-γ-ImPyPy-β-Dp, ImPy-β-ImPy-γ-ImPy-β-ImPy-β-Dp and mixtures thereof and a pharmaceutically acceptable excipient suitable for the treatment of HIV-1 infection. The invention also provides a method of treating a human patient with an HIV-1 infection comprising the step of administering a composition comprising a transcription inhibiting amount of at least one polyamide chosen from the group consisting of ImPyPyPy-γ-ImPyPy-β-Dp, ImPy-β-ImPy-γ-ImPy-β-ImPy-β-Dp and mixtures thereof and a pharmaceutically acceptable excipient. Preferably a transcription inhibiting amount corresponds to an extracellular concentration of polyamide of about 100 nanomolar to about 10 micromolar. In one preferred embodiment, a transcription inhibiting amount corresponds to an extracellular concentration of about one micromolar to about ten micromolar ImPyPyPy-γ-ImPyPy-β-Dp mixed with about one micromolar to about ten micromolar ImPy-β-ImPy-γ-ImPy-β-ImPy-β-Dp.

The present invention provides methods of treating cells in vitro as well as treating a human patient or a non-human organism in vivo. In one preferred embodiment, the invention provides a method of treating HIV-1 infected human blood cells in vitro comprising the step of administering a composition comprising a transcription inhibiting amount of at least one polyamide chosen from the group consisting of ImPyPyPy-γ-ImPyPy-β-Dp, ImPy-β-ImPy-γ-ImPy-β-ImPy-β-Dp and mixtures thereof.

In other embodiments, the invention provides a diagnostic kit for detecting the identified target DNA sequence by employing the selective polyamides and a suitable system for the detection of the polyamide bound to the DNA.

BRIEF DESCRIPTION OF THE DRAWINGS

FIG. 5 is a schematic representation of the HIV-1 genome that encodes Gag, Pol, Env and six regulatory proteins as well as anticipated formally matched complexes of 1 and 4, and formally mismatched complexes of 2, 3, 5, and 6 with the HIV-1 target sequence 5'-TGCTGCA-3'.

FIG. 6 is a schematic representation of the structures of 5-γ-5 polyamides 1–3, and 2-β-2-γ-2 polyamides 4–6.

FIG. 10 is a representation of the results of a MPE.Fe$^{II}$ footprint experiment showing binding of a seven base pair sequence by polyamides 4, 5, 6, and 3.

FIG. 11 is a representation of the sequence of the HIV-1 enhancer/promoter element showing the binding sites for the cellular transcription factors Ets-1, LEF-1, NF-κB and SP1 along with a canonical TBP binding site, or "TATA element."

FIG. 16 is a schematic model of the binding of the polyamides ImPy-β-ImPy-γ-ImPy-β-ImPy-β-Dp, also called HIV-1, and ImIm-β-ImIm-γ-PyPy-β-PyPy-β-Dp, also called HIV-2 to the DNA sequences adjacent to the HIV-1 TATA box.

FIG. 17 is a schematic model of the binding of polyamides designed for the recognition of TFIID (1a–1c) and Ets-1/LEF-1 (2a–2b) binding sites.

FIG. 19 is a representation of the results of a footprint experiment comparing the binding of polyamides and TBP.

FIG. 21 is a representation of the results of a footprint experiment comparing the binding of polyamides, HIV-1 and CMV.

FIG. 29 is a schematic model of the binding of polyamides designed for the recognition of DNA sequence adjacent to the CMV TBP binding site and the repressor binding site.

DETAILED DESCRIPTION OF PREFERRED EMBODIMENTS

Figure 1A:
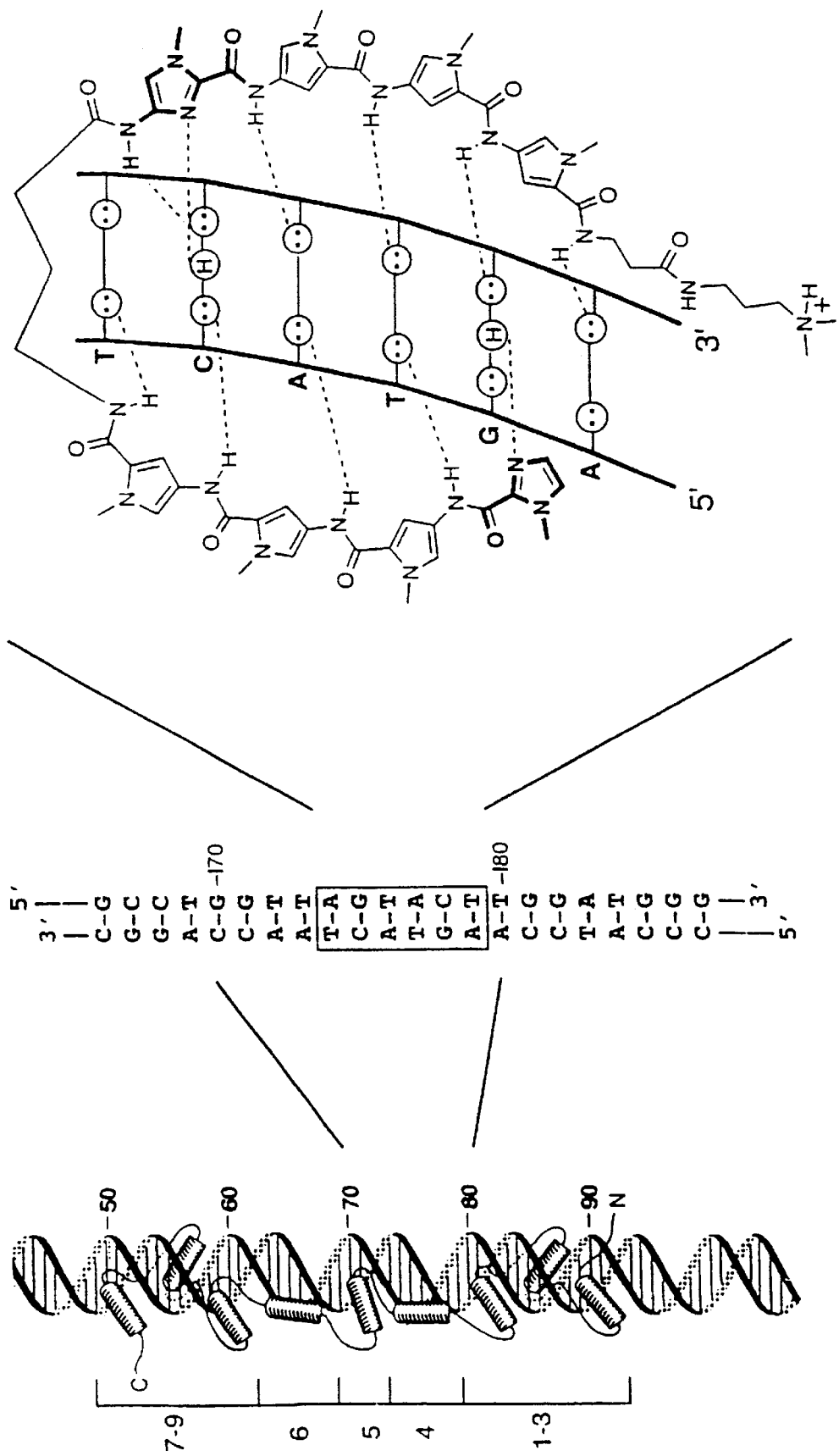
FIG. 1 is a representation of a schematic model for the interaction of the nine zinc finger protein TFIIIA with the 5S ribosomal RNA gene internal control region (ICR).

Pyrrole-imidazole polyamides represent the only class of small molecules to date that can bind any predetermined DNA sequence. DNA recognition depends on side-by side amino acid pairings in the minor groove. A pairing of imidazole (Im) opposite pyrrole (Py) targets a G-C base pair. A Py/Py combination is degenerate and targets both T-A and A-T base pairs. However, Hp/Py is specific for a T-A base pair and Py/Hp is specific for an A-T base pair. The generality of these pairing rules has been demonstrated by targeting a variety of sequences 5–13 base pairs in size and is supported directly by NMR structural studies. Eight-ring hairpin polyamides have affinities and specificities comparable to DNA-binding transcription factors.

Solid phase methods for synthesizing the polyamides of the present invention have been described by Baird & Dervan (J. Am. Chem. Soc., 118, 6141 (1996)). Alternatively, the polyamides can also be synthesized via solution phase methods as described by Weiss et al. (J. Am. Chem. Soc., 79, 1266 (1957)).

Many protein coding genes utilize both gene- and tissue-specific transcription factors as well as general transcription factors for transcription of mRNA by RNA polymerase II. The binding sites for these protein factors are found in numerous genes, whereas the sequences adjacent to these binding sites tend to be unique for each gene. Polyamide ligands can be designed which target both the sequences adjacent to the binding sites for these transcription factors as well as to the binding sequences for these factors. Polyamides that target these sequences will interfere with the binding of the protein factors to DNA and thereby inhibit transcription by RNA Polymerase II.

For example, the role of the nine zinc finger protein TFIIIA in the transcriptional regulation of the 5S RNA gene by RNA polymerase III has been extensively characterized. Zinc fingers 1–3, 5 and 7–9 bind the internal control region (ICR) of the gene through base-specific interactions in the major groove. Fingers 4 and 6 are essential for high affinity DNA binding and have been proposed to bind in or across the minor groove (FIG. 1). Well established methods exist for assessing in living cells the status of RNA polymerase III transcription complexes on the genes encoding the small 5S ribosomal RNA.

In another embodiment, polyamides have been designed and synthesized that recognize and bind the sequences immediately adjacent to the site at which the minor groove-binding protein TATA-box binding protein (TBP) binds to TATA DNA can be designed. DNA sequences adjacent to the TATA elements are gene-specific whereas TATA elements are found in many protein-coding genes. For example, a polyamide bound to the sequence adjacent to the HIV-1 TATA element has been shown to inhibit HIV-1 promoter-specific transcription by RNA polymerase II. A polyamide designed to selectively bind this site would be useful for treating diseases associated with HIV-1 infection.

In a third embodiment, a polyamide recognizes and binds the sequence immediately adjacent to the binding site of lymphoid enhancer factor LEF-1 in the HIV-1 enhancer. This polyamide inhibits the binding to LEF-1 protein to HIV-1 DNA. As above, a polyamide designed to selectively bind this site would be useful for treating diseases associated with HIV-1 infection.

In another embodiment, a polyamide recognizes and binds to an identified target sequence adjacent to the transcription factor protein binding site of a cellular gene. In one preferred embodiment, the cellular gene is a constitutively expressed gene under basal transcription control. An preferred cellular gene under basal transcription control is the gene encoding the 5S ribosomal subunit.

In yet another preferred embodiment, the minor groove transcription factor protein of the cellular gene is TBP. Such preferred cellular genes include oncogenes such as LEF-1, Ets-1 and her-2/neu. Other such preferred cellular genes include genes encoding cytokines such as interleukins, including IL-2, IL-5 and IL-13, tumor necrosis factors, including TNF-alpha and TNF-beta, growth factors, including TGF-beta, and colony stimulating factors, including GM-CSF.

Using the above described rules, a sequence-specific polyamide can be designed that selectively binds to an identified target site adjacent to the binding site of a minor groove transcription factor protein. As used herein, "adjacent" includes 1) polyamide binding sites wherein an end nucleotide base pair of the polyamide binding site is immediately contiguous to an end nucleotide of the minor groove transcription factor protein binding site, 2) polyamide binding sites wherein one to five nucleotide base pairs of the polyamide binding site are shared with the binding sites of the minor groove transcription factor protein, and 3) polyamide binding sites wherein the polyamide binding site is separated from the minor groove transcription factor protein binding site by from one to four intervening nucleotide base pairs. The binding affinity of such a designed polyamide should be greater than the binding affinity of the native transcriptional element in order to inhibit transcription. The binding affinity can be ascertained by competitive inhibition experiments against a native transcription factor.

Within this application, unless otherwise stated, definitions of the terms and illustration of the techniques of this application may be found in any of several well-known references such as: Sambrook, J., et al., Molecular Cloning: A Laboratory Manual, Cold Spring Harbor Laboratory Press (1989); Goeddel, D., ed., Gene Expression Technology, Methods in Enzymology, 185, Academic Press, San Diego, Calif. (1991); "Guide to Protein Purification" in Deutshcer, M. P., ed., Methods in Enzymology, Academic Press, San Diego, Calif. (1989); Innis, et al., PCR Protocols: A Guide to Methods and Applications, Academic Press, San Diego, Calif. (1990); Freshney, R. I., Culture of Animal Cells: A Manual of Basic Technique, 2nd Ed., Alan Liss, Inc. New York, N.Y. (1987); Murray, E. J., ed., Gene Transfer and Expression Protocols, pp. 109–128, The Humana Press Inc., Clifton, N.J. and Lewin, B., Genes VI, Oxford University Press, New York (1997).

For the purposes of this application, a promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening, non-coding sequences ("introns") between individual coding segments ("exons"). Coding refers to the representation of amino acids, start and stop signals in a three base "triplet" code. Promoters are often upstream ("5' to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the sense strand of DNA is positioned about 30 base pairs upstream of the transcription start site, the sequence forms part of the promoter region (Lewin, Genes VI, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, Genes VI, pp. 213–215).

While not being held to one hypothesis, it is believed that the binding of the polyamides of this invention modulate gene expression by altering the binding of DNA binding proteins, such as RNA polymerase, transcription factors, TBP, TFIIIA, the lymphoid enhancer factor protein LEF-1, and other minor groove transcription factor proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 in Table I lists numerous pathogens in which are found medically significant target sequences for DNA-binding drugs and in Table II lists many non-infectious diseases that may be controlled at the level of DNA binding proteins.

It is generally understood by those skilled in the art that the basic structure of DNA in a living cell includes both major and a minor groove. For the purposes of describing the present invention, the minor groove is the narrow groove of DNA as illustrated in common molecular biology references such as Lewin, B., Genes VI, Oxford University Press, New York (1997).

To affect gene expression in a cell, which may include causing an increase or a decrease in gene expression, a quantity of one or more polyamides effective to inhibit transcription is contacted with the cell and internalized by the cell. The cell may be contacted by the polyamide in vivo or in vitro. Effective transcription inhibiting extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated cell tissue culture plates and various quantities of one or more polyamide are added to separate wells. Gene expression following exposure to a polyamide can be monitored in the cells or in the medium by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and western blot. Alternatively, gene expression following exposure to a polyamide can be monitored by the detecting the amount of messenger RNA present as determined by various techniques, including northern blot and RT-PCR.

The polyamides of this invention may be formulated into diagnostic and therapeutic compositions for in vivo or in vitro use. Representative methods of formulation may be found in Remington: The Science and Practice of Pharmacy, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising, a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, ethyl red, 4-(psoraen-8-yloxy)-butyrate, tartaric acid, (+)-α-tocopheral, psoralen, EDTA, methidium, acridine, Ni(II).Gly-Gly-His, TO, Dansyl, pyrene, N-bromoacetamide, and gold particles. Such bifunctional polyamides are useful for DNA affinity capture, covalent DNA modification, oxidative DNA cleavage, and DNA photocleavage. Such bifunctional polyamides are useful for DNA detection by providing a polyamide linked to a detectable label. Detailed instructions for synthesis of such bifunctional polyamides can be found in copending U.S. provisional application No. 60/043,444, the teachings of which are incorporated by reference.

DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microtiter plate well to which microgram quantities of a contemplated polyamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

EXAMPLE 1

Transcription Inhibition in vitro and in vivo.

A high speed cytosolic extract from unfertilized Xenopus eggs was prepared as described in Hartl, et al., *J. Cell Biol.* 120, 613–624 (1993). DNA templates for transcription were the somatic-type 5S RNA gene contained in plasmid pX1s11 (50 ng per reaction; Peterson et al., *Cell* 20, 131, 1980) and the tyrD tRNA gene contained in plasmid pTyrD (100 ng per reaction; Stutz, et al., *Genes Dev.* 3, 1190, 1989) both from *Xenopus laevis*. Transcription reactions (20 μL final volume) contained the following components: 2.5 μL extract, 9 ng (12 nM) of TFIIIA isolated from immature oocytes (Smith et al., *Cell*, 37, 645, 1984), 0.6 mM ATP, UTP, CTP, 0.02 mM GTP and 10 μCi of [α-$^{32}$P] GTP, and the final buffer components 12 mM HEPES (pH 7.5), 60 mM KCl, 6 mM $MgCl_2$, 25 μM $ZnCl_2$, and 8% (v/v) glycerol. Plasmid DNAs were pre-incubated with polyamides in the same buffer prior to adding TFIIIA and other reaction components. RNA was purified and analyzed on a denaturing 6% polyacrylamide gel. A Molecular Dynamics Phosphorimager equipped with ImageQuant software was used to quantify the effects of the polyamides on the relative transcription efficiencies of the 5S and TRNA genes.

Fibroblasts from a Xenopzis kidney derived cell line (kindly provided by Dr. P. Labhart, The Scripps Research Institute) were grown at ambient temperature in 25 $cm^2$ culture flasks in Dulbecco's modified Eagle medium containing 10% (v/v) fetal calf serum. Cells were passaged for a minimum of three days prior to the addition of polyamide to the culture medium. Incubations were continued for various times and nuclei were prepared by hypotonic lysis and used as templates for transcription as described. DNA content was determined by measuring the absorbance of an aliquot of the isolated nuclei in 1% (w/v) sodium dodecyl sulfate (using an extinction coefficient at 260 nM of 1 AU=50 µg/mL DNA). The buffer components and labeled and unlabeled nucleoside triphosphates were as for the plasmid transcription reactions. Reactions were supplemented with 2 µL of RNA polymerase III (at approximately 50 µg/mL) isolated from Xenopus oocytes.

Footprinting experiments reveal 90% inhibition of TFIIIA binding in the presence of 5 nM polyamide. After incubation with 60 nM polyamide in a cell-free extract derived from Xenopus oocytes, the transcriptional activity of a 5S gene is inhibited by >80%. When 100 nM polyamide is supplied in culture medium containing Xenopus kidney cells, transcription complexes on the 5S RNA genes are selectively disrupted. These results demonstrate that pyrrole-imidazole polyamides are cell permeable and can inhibit the transcription of a specific gene in living cells.

Polyamides were synthesized by solid phase methods as described in Baird, E. E. & Dervan, P. B. *J. Am. Chem. Soc.* 118, 6141–6146 (1996). The identity and purity of the polyamides was verified by $^1$H NMR, matrix-assisted laser desorption/ionization time of flight mass spectrometry (MALDI-TOF-MS), and analytical HPLC. MALDI-TOF-MS: 1, 1223.4 (1223.3 calculated for M+H); 2, 1222.3 (1222.3 calculated for M+H); 3, 1223.1 (1223.3 calculated for M+H).

The eight-ring polyamide (labelled 1 in FIG. 1*b*) having the sequence composition ImPyPyPy-γ-ImPyPyPy-β-Dp was synthesized by solid phase methods and shown to bind the six base pair site 5'-AGTACT-3' at subnanomolar concentration (FIG. 1). This sequence is within the binding site for zinc finger 4 of TFIIIA. Quantitative DNAse I footprint titration experiments reveal that polyamide 1 of FIG. 1*b* selectively binds the six base pair target sequence with a dissociation constant, $K_d$=0.03 nM, a higher affinity than TFIIIA for its 50 base pair site ($K_d$~1 nM). For controls, mismatch eight-ring polyamides ImPyPyPy-γ-PyPyPyPy-β-Dp (labelled 2 in FIG. 1*b*) and ImPyImPy-γ-PyPyPyPy-β-Dp (labelled 3 in FIG. 1*b*) were prepared which have 100-fold ($K_d$=2.0 nM) and 1000-fold ($K_d$=33 nM) lower affinities, respectively, for the 5'-AGTACT-3'site. The models of the binding of the polyamides to the identified target sequences of double stranded DNA are illustrated in FIG. 1*c*.

The left side of FIG. 1*a* shows a schematic model for the interaction of the nine zinc finger protein TFIIIA with the 5S ribosomal RNA gene internal control region (ICR). The middle section of FIG. 1*a* shows the sequence of the ICR recognized by finger 4 in the minor groove. The six base pair region targeted by the designed "hairpin" polyamide is enclosed in a rectangle. The right section of FIG. 1*a* shows the expected complex of ImPyPyPy-γ-ImPyPyPy-β-Dp (polyamide 1) with its identified target DNA sequence, 5'-AGTACT-3'. Circles with dots represent lone electron pairs on N3 of purines and 02 of pyrimidines. Circles containing an H represent the N2 hydrogen of guanine. Putative hydrogen bonds are illustrated by dashed lines.

FIG. 1*b* shows the structures of polyamides ImPyPyPy-γ-ImPyPyPy-β-Dp (1), ImPyPyPy-γ-PyPyPyPy-β-Dp (2), and ImPyImPy-γ-PyPyPyPy-β-Dp (3). The models of binding of these polyamides to the target duplex DNA sequence are shown in FIG. 1*c*. The filled and empty circles represent imidazole and pyrrole rings, respectively, the curved line represents γ-aminobutyric acid (γ), and the diamond represents β-alanine. Hydrogen bond mismatches such as G-Py and A-Im are highlighted.

Figure 2:
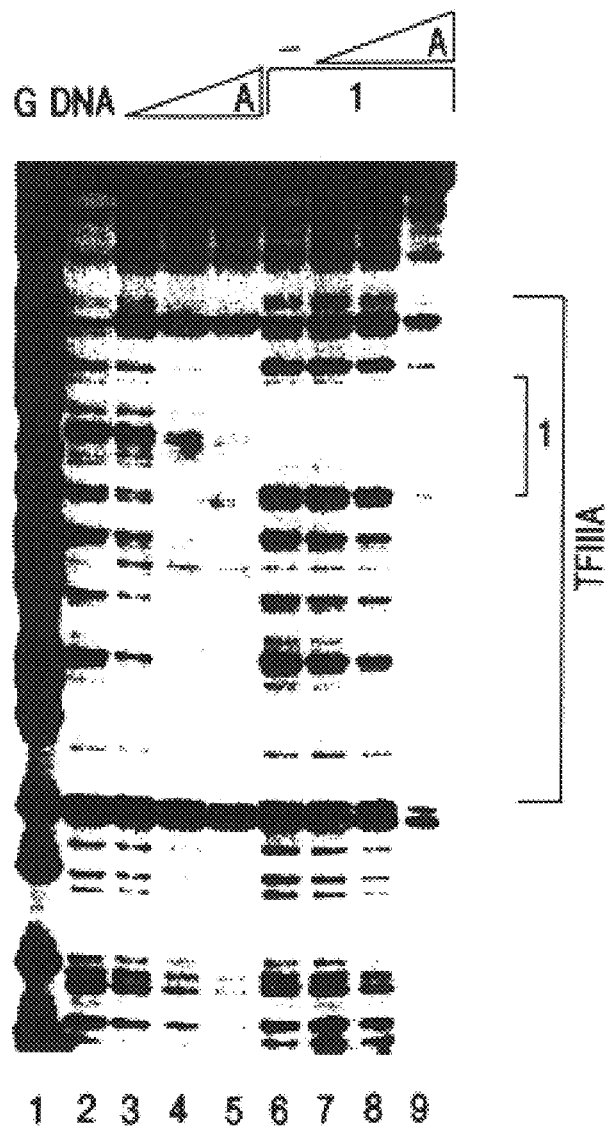
FIG. 2 is a representation of the results of DNase I footprinting analysis of the binding of polyamide 1 and TFIIIA to the 5S RNA gene ICR.

The effect of polyamide labelled 1 in FIG. 1*b* (ImPyPyPy-γ-ImPyPyPy-β-Dp) on TFIIIA binding to a restriction fragment isolated from a 5S RNA gene-containing plasmid was examined. Zfl-3, a recombinant TFIIIA analog missing fingers 4–9, binds in the major groove of the C-block promoter element (see FIG. 1*a*). DNase I footprinting demonstrates that zfl-3 and polyamide 1 can co-occupy the same DNA molecule. When 5 nM polyamide 1 was preincubated with the same DNA target, the binding of nine finger TFIIIA was inhibited by >90% (FIG. 2). FIG. 2 shows the result of DNase I footprinting analysis of the binding of polyamide 1 and TFIIIA to the 5S RNA gene ICR. 5'-end-labeled restriction fragments were derived from the 5S RNA gene by standard methods and footprinting reactions were as described in Clemens, K. R., et al., *J. Mol. Biol.* 244 23–35 (1994). Lane 1 shows a DMS G-specific sequencing ladder, lane 2, protein-free DNA, lanes 3–5, digestion products obtained in the presence of 0.5 nM, 1 nM and 2 nM TFIIIA, respectively, lane 6, digestion products obtained in the presence of 5 nM polyamide 1. Lanes 7–9 show the digestion products of reactions in which tile DNA was incubated with 1 for 30 min prior to the addition of TFIIIA (at the same concentrations as in lanes 3–5, respectively) and incubated for an additional 30 min prior to DNase treatment. The differential inhibition of zfl-3 and full-length TFIIIA provides evidence that finger 4 interacts with or is placed in the minor groove. Polyamide 1 does not inhibit TFIIIA binding to 5S RNA.

Figure 3A:
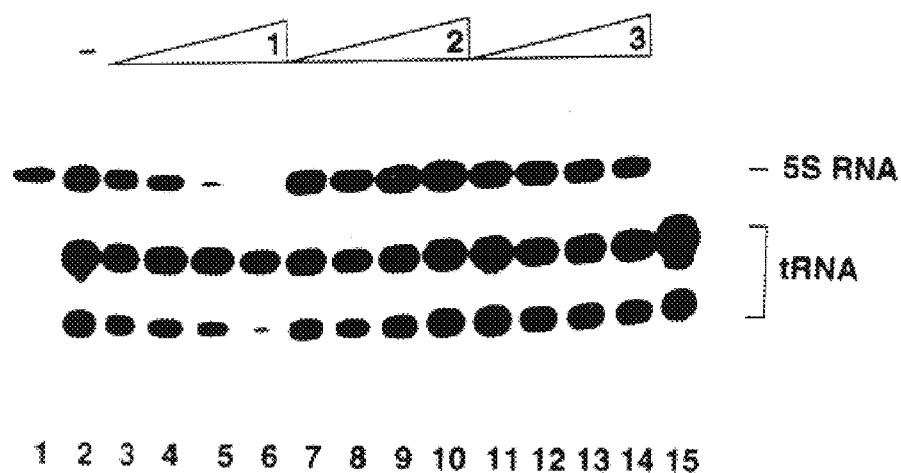
FIG. 3 is a representation of the results of experiments demonstrating inhibition of 5S RNA gene transcription in vitro.

Transcription of the 5S RNA gene in an in vitro system was monitored in the presence of increasing concentrations (10–60 nM) of polyamide 1. The results are shown in FIG. 3. In these experiments, polyamide 1 was added to a 5S RNA gene containing plasmid prior to the addition of exogenous TFIIIA (12 mM) and a crude extract derived from unfertilized Xenopus eggs. As a control, a tyrosine tRNA gene was included on a separate plasmid in these reactions. The tRNA gene has an upstream binding site for polyamide 1, but lacks a predicted protein-DNA interaction. Both genes are actively transcribed in this system, either individually (lanes 1 and 15) or in mixed template reactions (lane 2). Addition of 60 nM polyamide 1 inhibits 5S gene transcription by >80% (lane 6). Only a small degree of non-specific inhibition of tRNA transcription is observed at the concentrations of polyamide 1 required for efficient 5S RNA inhibition. The targeted 5S RNA gene is inhibited approximately 10-fold more effectively than the control tRNA gene.

Figure 3B:
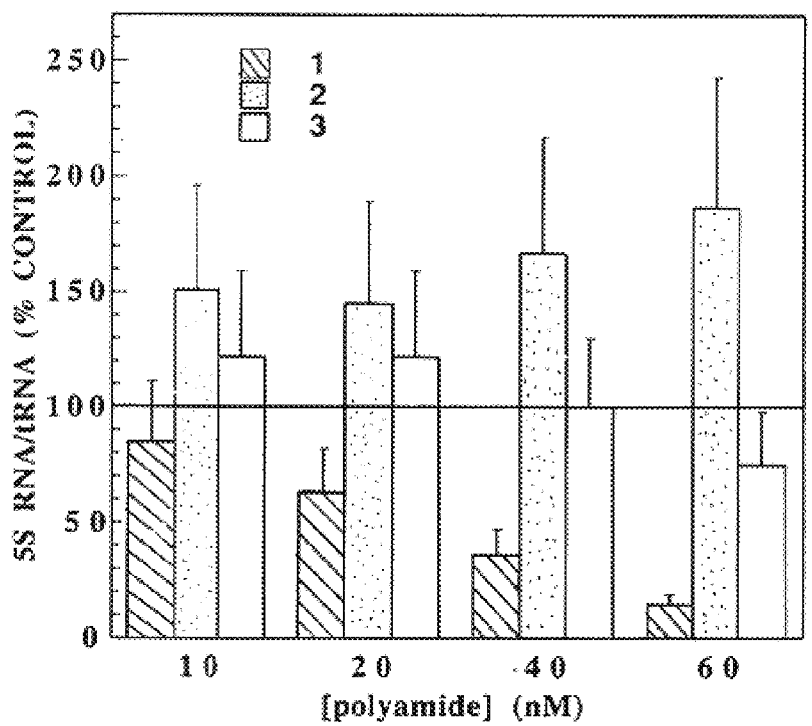

In these experiments the DNA templates were incubated with polyamide for 30 min prior to the addition of TFIIIA, a cytoplasmic extract prepared from unfertilized Xenopus eggs, and labeled and unlabeled nucleoside triphosphates. Reactions contained either the somatic-type 5S RNA gene (FIG. 3*a*, lane 1), a tRNA$^{tyrD}$ gene (lane 15), or a mixture of both genes (lanes 2–14). Reactions contained the following final concentrations of the indicated polyamide: 0 nM, lanes 1, 2, 15; 10 nM, lanes 3, 7, 11; 20 nM, lanes 4, 8, 12; 40 nM, lanes 5, 9, 13; 60 nM, lanes 6, 10, 14. Transcription reactions were stopped after 1 hour at ambient room temperature and the RNA products were analyzed on a denaturing polyacrylamide gel. The positions of 5S RNA and the tRNA primary and processed transcripts are indicated at the right of the autoradiogram. In FIG. 3*b* the results are represented graphically, with inhibition results expressed as the ratio of 5S RNA to tRNA transcription relative to the ratio obtained in the absence of polyamide. The error bars represent estimated standard deviations.

Mismatch polyamides ImPyPyPy-γ-PyPyPyPy-β-Dp (2) and ImPyImPy-γ-PyPyPyPy-β-Dp (3) did not inhibit 5S RNA transcription at concentrations up to 60 nM. If the TFIIIA-DNA complex is first allowed to form, 30 nM polyamide 1 added, and the mixture incubated for 90 minutes prior to adding egg extract, efficient inhibition (80%) of 5S RNA transcription is also observed. Shorter incubation times result in less inhibition. The required incubation time of 90 minutes is similar to the measured half-life of the TFIIIA-DNA complex and supports that polyamide 1 forms a more stable complex with DNA than does TFIIIA.

The effect of the polyamides on 5S gene transcription in vivo was determined (FIG. 4). Xenopus kidney-derived fibroblasts were grown in the presence of increasing concentrations of polyamide 1 in the culture medium for various times. Concentrations of polyamide up to 1 µM were not toxic, as measured by cell density, if growth was limited to less than 72 hours. Nuclei were prepared from cells by hypotonic lysis and equivalent amounts of the isolated nuclei from control and treated cells were used as templates for transcription with exogenous RNA polymerase III and labeled and unlabeled nucleoside triphosphates. This experiment monitors the occupancy of class III genes with active transcription complexes. 5S RNA transcription can easily be assessed since the repetitive 5S genes give rise to a prominent band on a denaturing polyacrylamide gel. An autoradiogram was taken of the gel and the following observations made base(d on the observed autoradiogram.

Figure 4A:
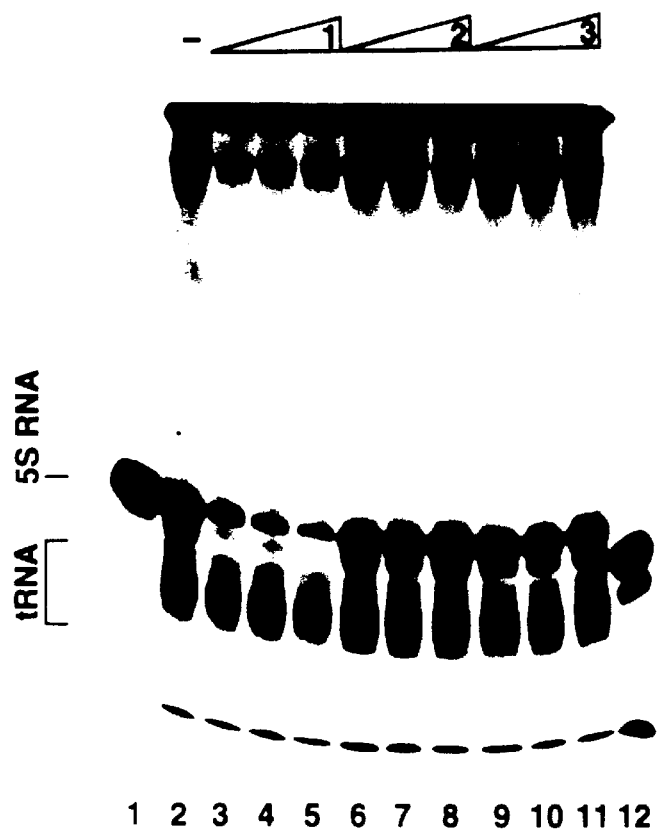
FIG. 4 is a representation of the results of an experiment demonstrating the inhibition of 5S RNA gene transcription complex formation in vivo.
Figure 4B:
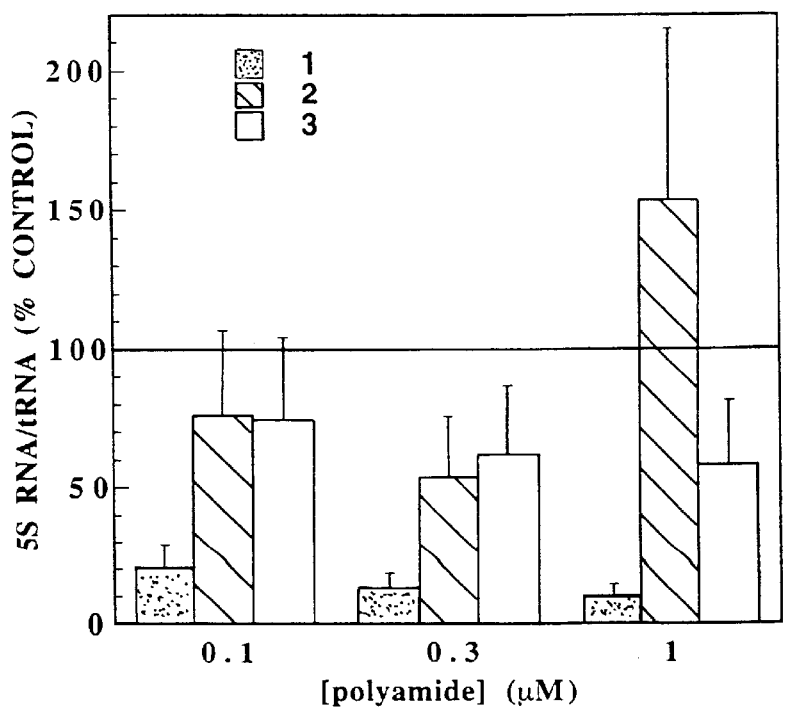

Nuclei were prepared from Xenopus kidney-derived fibroblasts that were grown in culture in the presence or absence of polyamides. Polyamides were included in culture medium (in 2.5 mL of media per 25 cm² flask) for 24 hours prior to harvesting cells and isolation of nuclei. Equal amounts of nuclei (containing 5 µg of DNA) were incubated for 2 hours in 20 µL reactions containing Xenopzis RNA polymerase III and labeled and unlabeled nucleoside triphosphates. RNA was isolated from these reactions and analyzed on a denaturing polyacrylamide gel. The results are shown in FIG. 4a in which lane 1 is a 5S RNA marker; lane 12 is a tRNA$^{tyrD}$ gene marker; lane 2, cells not exposed to polyamide; lanes 3–11, cells exposed to the indicated polyamides 1, 2, or 3 at the following concentrations: 100 nM, lanes 3, 6, 9; 300 nM, lanes 4, 7, 10; 1 µM, lanes 5, 8, 11. FIG. 4b is a graphic representation of the effects of polyamides 1, 2 and 3 on 5S RNA and tRNA transcription expressed as the ratio of 5S RNA to tRNA gene transcription relative to the ratio obtained in the absence of polyamide. Error bars represent estimated standard deviations.

Concentrations of polyamide 1 as low as 100 nM have a pronounced and selective effect on 5S transcription. At higher polyamide concentration, a general decrease in the transcriptional activity of the nuclei is observed. However, phosphorimage analysis of this experiment reveals that at each concentration tested, the effects of the polyamide are much greater on 5S RNA transcription than on tRNA transcription. Having established that nearly maximal inhibition of 5S transcription is achieved with1 µM polyamide 1, nuclear transcription was monitored after various times of cell growth in the presence of the polyamide. No inhibition is observed for zero time incubation with polyamide 1 at 1 µM concentration, indicating that disruption of transcription complexes does not occur during or after the isolation or work-up of cell nuclei. Statistically equivalent levels of 5S transcription were observed when the cells were exposed to polyamide 1 for 24, 48 or 72 hours.

These nuclear transcription experiments indicate that polyamide 1 is able to enter cells, transit to the nucleus and disrupt transcription complexes on the chromosomal 5S RNA genes. To rule out the possibility that the observed inhibition is due to some non-specific toxicity of the polyamide rather than to direct binding to the 5S RNA gene, the effects of mismatch polyamides 2 and 3 in the nuclear transcription assay were monitored. Only a small effect on 5S RNA synthesis relative to tRNA synthesis is observed with 1 µM of the mismatch polyamides 2 or 3 in the culture medium for 24 hours. This result indicates that the general inhibition of transcription observed with high concentrations of polyamide 1 may be a secondary effect of the inhibition of 5S RNA synthesis in vivo, rather than the result of non-specific polyamide interactions. Polyamide 2 affects a small enhancement of 5S RNA transcription in vitro and in vivo, indicating that polyaimdes may be able to upregulate transcription in certain cases.

EXAMPLE 2

Design and Synthesis of Optimized Polyamides Targeted to HIV-1 Promoter Sequences The experiments of Example 1 showed that an eight-ring "4-γ-4 motif" polyamide having the sequence composition ImPyPyPy-γ-ImPyPyPy-β-Dp binds specifically to the six base pair site 5'-AGTACT-3'. It has also been shown recently that the 10-ring, "5-γ-5 motif" polyamide ImPyPyPyPy-γ-ImPyPyPyPy-β-Dp specifically binds a seven base pair 5'-WGWWWCW-3' target sequence with subnanomolar affinity in a hairpin conformation (Trauger, J. W., et al., J. Am. Chem. Soc., 118 6160–6166, 1996). Applying the polyamide pairing rules to the 5-γ-5 molecular template suggested that the 10-ring hairpin polyamide ImPyPyImPy-γ-ImPyPyImPy-β-Dp would bind the HIV-1 target sequences 5'-WGCWGCW-3'. However, as reported below, polyamide polyamide ImPyPyImPy-γ-lmpyPyImPy-β-Dp specifically binds the target site 5'-TGCTGCA-3', but with relatively low affinity, necessitating development of a second-generation polyamide.

Design of Second Generation Polyamide 4. The simple amino acid β-alanine has been employed effectively as a single base pair-spanning linker in many different polyamides. In particular, in many cases in which a polyamide binds with relatively low affinity due to an apparent register mismatch between polyamide residues and their target DNA bases, substitution of one or more pyrrole residues with the flexible spacer β-alanine results in marked increases in binding affinity. These results suggested that the 8-ring polyamide ImPy-β-ImPy-γ-ImPy-β-ImPy-β-Dp (4), which differs from 1 only by the replacement of two pyrrole residues with β-alanines, would specifically bind the HIV-1 target sequences 5'-WGCWGCW-3' with high affinity using a novel 2-β-2-γ-2-β-2 motif. Equilibrium association constants were determined by quantitative DNase I footprinting titration experiments of the formally matched (according to the polyamide pairing rules) polyamides 1 and 4 and the formally mismatched polyamides 2, 3, 5, and 6 for the HIV-1 target sequence 5'-TGCTGCA-3' (FIGS. 5b and 6). To further demonstrate the general usefulness of the 2-β-2-γ-2-β-2 motif, the binding of 2 and 5, and 3 and 6 to their respective formal match sequences 5'-TGGTGGA-3' and 5'-TGTTACA-3' was examined. MPE.Fe$^{II}$ footprinting and affinity cleavage studies were performed for a subset of these compounds. Finally, the equilibrium association constants of polyamide 4 for the HIV-1 target sequence 5'-TGCTGCA-3' were determined at either 24° C. or 37° C., and using either standard polyamide assay solution conditions or approximate intracellular solution conditions.

NMR spectra were recorded on a GE 300 instrument operating at 300MHz ($^1$H). Spectra were recorded in DMSO-$d_6$ with chemical shifts reported in parts per million relative to residual DMSO-$d_5$. Polyamide concentrations were determined by UV absorbance measurements made on a Hewlett-Packard Model 8452A diode array spectrophotometer. Matrix-assisted, laser desorption/ionization time of flight mass spectrometry was carried out at the Protein and Peptide Microanalytical Facility at the California Institute of Technology. Analytical HPLC was performed on a HP 1090M analytical HPLC using a Rainen C18, Microsorb MV, 5 m, 300×4.6 mm reversed phase column in 0.1% (wt/v) TFA with acetonitrile as eluent and a flow rate of 1.0 ml/min, gradient elution 1.25% acetonitrile/min. Preparative HPLC was carried out on a Beckman instrument using a Waters Deltapak 25×100 mm, 100 m $C_{18}$ column in 0.1% (wt/v) TFA, gradient elution 0.25%/min. $CH_3CN$. E. coli XL-1 Blue competent cells were obtained from Stratagene. Restriction endonucleases were i.purchased from Boeringher-Mannheim or New England Biolabs. Plasmid isolation kits were obtained from Promega Plasmid sequencing was carried at the Sequence Analysis Facility at the California Institute of Technology. Sequenase (version 2.0) was obtained from United States Biochemical, and DNase I (FPLCpure) was obtained from Pharmacia. [$\alpha$-$^{32}$P]-Thymidine-5'-triphosphate ($\geq$000 $C_i$/mmol), [$\alpha$-$^{32}$P]-deoxyadenosine-5'-triphosphate ($\geq$6000 $C_i$/mmol), and [$\alpha$-$^{32}$P]-adenosine-5'-triphosphate were purchased from Du Pont/NEN. Water was obtained from a Millipore Milli-Q water purification system.

Synthesis. Polyamides were prepared by stepwise solid-phase synthesis using BOC-protected monomers as described by Baird, E. E.; Dervan, P. B. *J. Am. Chem. Soc.* 1996, 118, 6141–6146.

Plasmids. Plasmid pJT2B2 was prepared by hybridizing the complementary oligonucleotides, 5'-CCGGCTTAAG TTCGTGGGCC ATGCTGCATT CGTGGGCCA TGGTGGA TTCG TGGGCCATGT TACATTCG-3' (SEQ ID NO:1) and 5'-TCGACGAATG TAACATGGCC CAC-GAATCCA CCATGGCCCA CGAATGCAGC ATGGC-CCACG AACTTAAG-3' (SEQ ID NO:2), and ligating the resulting duplexes to the large pUC19 AvaI/Sal I restriction fragment.

The plasmid was transformed into *E.coli*, and plasmid DNA isolated using standard methods, and the sequence of the insert confirmed by sequencing. The 3'-$^{32}$P end-labeled Eco RI/Pvu II restriction fragment was prepared by simultaneous digestion with Eco RI and Pvu II and 3'-fill-in using Sequenase, [$\alpha$-$^{32}$P]-deoxyadenosine-5'-triphosphate, and [$\alpha$-$^{32}$P]-thymidine-5'-triphosphate. The 282 bp fragment was isolated by nondenaturing gel electrophoresis. The 5'-$^{32}$P-end-labeled EcoRI/PvuII fragment was prepared using standard methods. See Sambrook, J.; Fritsch, E. F.; Maniatis, T. *Molecular Cloning*; Cold Spring Harbor Laboratory: Cold Spring Harbor, N.Y., 1989.

A-specific chemical sequencing was carried out as described by Iverson, B. L.; Dervan, P. B. *Nucleic Acids Res.* 1987, 15, 7823–7830. Standard methods as described by Sambrook, et al. (1989) were used for all DNA manipulations.

Quantitative DNase I Footprinting. Equilibrium association constants for polyamide-DNA complexes were determined by quantitative DNase I footprint titration experiments. Reactions were carried out in a total volume of 400 $\mu$L in the absence of carrier DNA. A polyamide stock solution or $H_2O$ (for reference lanes) was added to a solution containing 3'-end-labeled restriction fragment (15,000 cpm) affording final solution conditions of either 10 mM Tris.HCl, 10 mM KCl, 10 mM $MgCl_2$, 5 mM $CaCl_2$, pH 7.0. at 24° C., or 10 mM HEPES.HCl, 140 mM KCl, 10 mM NaCl, 1 mM $MgCl_2$, 1 mM spermine, pH 7.2 as indicated in Tables 1 and 2. The solutions were allowed to equilibrate at 24° C. or 37° C. as indicated in Tables 1 and 2 for 12–16 hr. Cleavage reactions were initiated by the addition of 10 $\mu$L of a DNase I stock solution (at the appropriate concentration to give ~55% intact DNA) containing 1 mM dithiothreitol, allowed to proceed for 7 min. at 24° C., or 3.5 min. at 37° C., and stopped by the addition of 50 $\mu$L of a solution containing 2.25 M NaCl, 150 mM EDTA, 0.6 mg/mL glycogen, and 30 $\mu$M base-pair calf thymus DNA, and precipitated with1 mL ethanol. Reactions were then resuspended in 1×TBE/80% formamide, heated at 85° C. for 10 min, placed on ice, and the reaction products separated by electrophoresis on an 8% polyacrylaride gel (5% cross-link, 7 M urea) in 1×TBE at 2000 V. Gels were dried, exposed to a storage phosphor screen (Molecular Dynamics), and imaged using a Molecular Dynamics 400S PhosphorImager. Data was obtained from the imaged gels by quantitation using ImageQuant software (Molecular Dynamics). Background-corrected volume integration of rectangles encompassing the footprint sites and a reference site at which DNase I reactivity was invariant across the titration generated values for the site intensities ($I_{site}$) and the reference intensity ($I-_{ref}$). The apparent fractional occupancy ($\theta_{app}$) of the sites was then calculated using the equation:

$$\theta_{app} = 1 - \frac{I_{site}/I_{ref}}{I^o_{site}/I^o_{ref}} \qquad (1)$$

where $I^o{}_{site}$ and $I^o{}_{ref}$ are the site and reference intensities, respectively, from a control lane to which no polyamide was added. The ([L]$_{tot}$, $\theta_{app}$) data points were fit to a general Hill equation (eq. 2) by minimizing the difference between $\theta_{app}$ and $\theta_{fit}$:

$$\theta_{fit} = \theta_{min} + (\theta_{max} - \theta_{min})\frac{K_a^n[L]_{tot}^n}{1 + K_a^n[L]_{tot}^n} \qquad (2)$$

where [L]$_{tot}$ is the total polyamide concentration, $K_a$ is the equilibrium association constant, and $\theta_{min}$ and $\theta_{max}$ are the experimentally determined site saturation values when the site is unoccupied or saturated, respectively. The data were fit using a nonlinear least-squares fitting procedure with $K_a$, $\theta_{max}$, and $\theta_{min}$ as the adjustable parameters, and with a fixed value for n. For hairpin polyamides 1–6, binding isotherms were adequately fit by Langmuir isotherms (eq. 2, n=1), consistent with formation of a 1:1 polyamide-DNA complexes. For unlinked polyamides 7–9 binding to their match sequences, binding isotherms were adequately fit by a cooperative isotherm (eq. 2, n=2) consistent with cooperative dimeric binding. Reported association constants are the average value obtained from at least three independent footprinting experiments.

MPE.FE$^{II}$ Footprinting and Affinity Cleavage Experiments. Exact binding sites were determined by MPE.Fe$^{II}$ footprinting. Binding orientation was probed using affinity cleavage experiments. All reactions were carried out in a total volume of 400 $\mu$L. A stock solution of polyamide (for MPE.Fe$^{II}$ footprinting), polyamide-EDTA (for affinity cleavage), or $H_2O$ (for reference lanes) was added to a solution containing 3'- or 5'-end-labeled restriction fragment (15,000 cpm) affording final solution conditions of 20 mM HEPES, 200 mM NaCl, 50 $\mu$g/mL glycogen, and pH 7.3, and the solution allowed to equilibrate for 12 hr at 24° C. Next, for MPE.Fe$^{II}$ footprinting reactions, MPE.Fe$^{II}$ was added to a final concentration of 0.5 $\mu$M and the solution allowed to equilibrate for 10 min. (a 5 $\mu$M MPE.FE$^{II}$ stock solution was prepared by mixing equal volumes of 10 $\mu$M MPE and freshly prepared 10 μM Fe(NH$_4$)$_2$(SO$_4$)$_2$), and for affinity cleavage reactions, freshly prepared Fe(NH$_4$)$_2$(SO$_4$)$_2$ was added to a final concentration of 1 μM and the solution allowed to equilibrate for 30 min. For both MPE.Fe$^{II}$ footprinting and affinity cleavage, cleavage was initiated by the addition of dithiothreitol to a final concentration of 5 mM and allowed to proceed for 30 min at 24° C., then stopped by adding 1 mL ethanol. Next, 10 μL of a solution containing calf thymus DNA (140 μM base-pair) (Pharmacia) and glycogen (Boehringer-Mannheim) (2.8 mg/mL) was added, and the DNA precipitated. The reactions were resuspended in 1×TBE/80% formamide, heated at 85° C. for 10 min, placed on ice, and the reaction products separated by electrophoresis on an 8% polyacrylamide gel (5% cross-link, 7 M urea) in 1×TBE at 2000 V. Gels were dried and imaged target site 5'-TGTTACA-3' with very high affinity (K$_a$=5× 10$^{10}$ M$^{-1}$). (FIG. 8, Table 1).

Quantitative DNase I footprinting experiments reveal that the three 2-β-2-γ-2-β-2 motif polyamides 4, 5 and 6 selectively target their respective match sequences 5'-TGCTGCA-3' (the HIV-1 target sequence), 5'-TGGTGGA-3', and 5'-TGTTACA-3' with equilibrium association constants greater than 1×10$^9$ M$^{-1}$ (FIG. 8, Table 1), demonstrating that the 2-β-2-γ-2-β-2 motif allows specific targeting of a range of 7 base pair sequences with subnanomolar affinity, and is generally useful for all 5'-WNNWNNW-3' sequences. Polyamide 4 specifically binds the HIV-1 target sequence 5'-TGCTGCA-3' with subnanomolar affinity (Ka=2×10$^{10}$ M$^{-1}$), and thus represents a solution to the present polyamide design problem.

TABLE 1

| Polyamide | Equilibrium association constants (M$^{-1}$)$^a$ | | |
|---|---|---|---|
| | 5'-aTGCTGCAt-3' | 5'-aTGGTGGAt-3' | 5'-aTGTTACAt-3' |
| 5-γ-5 motif: | | | |
| 1 ImPyPyImPy-γ-ImPyPyImPy-β-Dp | 8.3 × 10$^7$ (1.5) | <1 × 10$^7$ | <1 × 10$^7$ |
| 2 ImImPyImIm-γ-PyPyPyPyPy-β-Dp | <5 × 10$^7$ | <5 × 10$^7$ | <5 × 10$^7$ |
| 3 ImPyPyPy-γ-ImPyPyPyPy-β-Dp | 1.2 × 10$^9$ (0.4) | <5 × 10$^8$ | 5.1 × 10$^{10}$ (1.1) |
| 2-β-2-γ-2-β-2 motif: | | | |
| 4 ImPy-β-ImPy-γ-ImPy-β-ImPy-β-Dp$^b$ | 1.5 × 10$^{10}$ (0.3) | <5 × 10$^8$ | <5 × 10$^8$ |
| 5 ImIm-β-ImIm-γ-PyPy-β-PyPy-β-Dp | 1.7 × 10$^8$ (0.3) | 7.6 × 10$^9$ (1.0) | <1 × 10$^8$ |
| 6 ImPy-β-PyPy-γ-ImPy-β-PyPy-β-Dp | <1 × 10$^8$ | <1 × 10$^8$ | 2.6 × 10$^9$ (1.0) |
| Unlinked dimer motif: | | | |
| 7 ImPyPyPyPy-β-Dp | 1.1 × 10$^7$ (0.2) | <1 × 10$^7$ | 3.9 × 10$^8$ (0.6) |
| 8 ImPy-β-ImPy-β-Dp | 3.0 × 10$^6$ (0.2) | <2 × 10$^5$ | 1.5 × 10$^6$ (0.3) |
| 9 ImPy-β-PyPy-β-Dp | <5 × 10$^5$ | <5 × 10$^5$ | 2.8 × 10$^6$ (0.1) |

$^a$Values reported are the mean values from at least three DNase I footprint titration experiments.
The standard deviation for each value is indicated in parentheses.
The assays were carried out at 24° C.
pH 7.0, in the presence of 10 mM Tris.HCl, 10 mM KCl, 10 mM MgCl$_2$, and 5 mM CaCl$_2$.
Nucleotides flanking polyamide binding sites are in lowercase type.
Association constants corresponding to formally matched complexes are in bold type.
$^b$This polyamide binds the site 5'-tgttacatTCGTCGAc-3' adjacent to the 5'-TGTTACA-3' site with an equilibrium association constant of 2.1 × 10$^9$ M$^{-1}$ (0.1).

as described above. Relative cleavage intensities were determined by volume integration of individual cleavage bands using ImageQuant software (Molecular Dynamics).

Results and Discussion

Synthesis

Polyamides were synthesized by solid phase methods as described in Baird, E. E.; Dervan, P. B. *J. Am. Chem. Soc.*, 118, 6141–6146 (1996).

Binding Affinities

Figure 7:
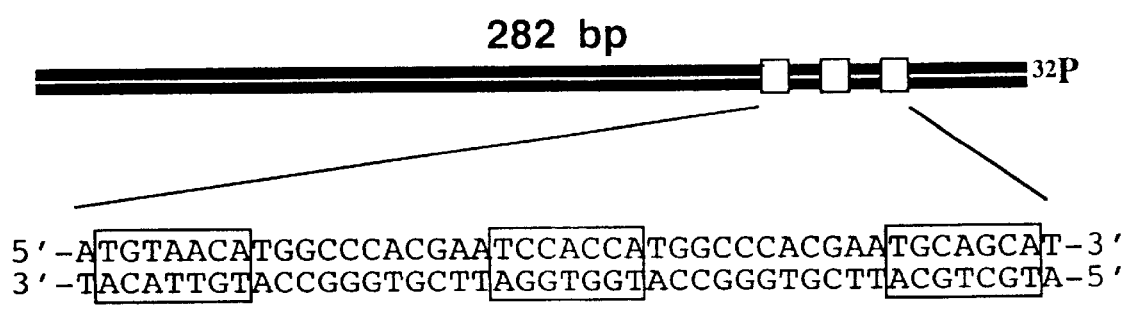
FIG. 7 is a schematic representation of part of the sequence of the restriction fragment used in quantitative DNase I footprinting experiments. The three 7 base pair target sites 5'-TGCTGCA-3' (the HIV-1 target site), 5'-TGGTGGA-3', and 5'-TGTTACA-3' are highlighted.
Figure 8A:
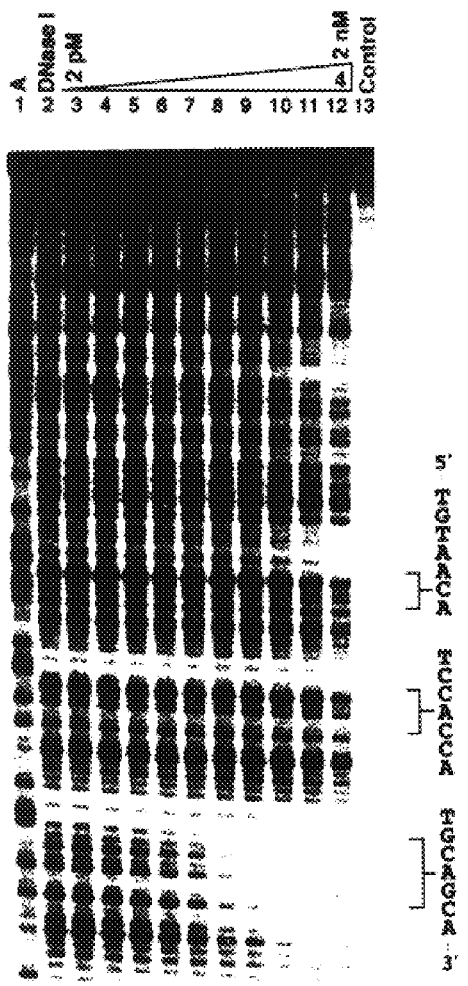
FIG. 8 is a representation of the results of a footprint experiment demonstrating the binding of polyamides 4–6 and 3.
Figure 8B:
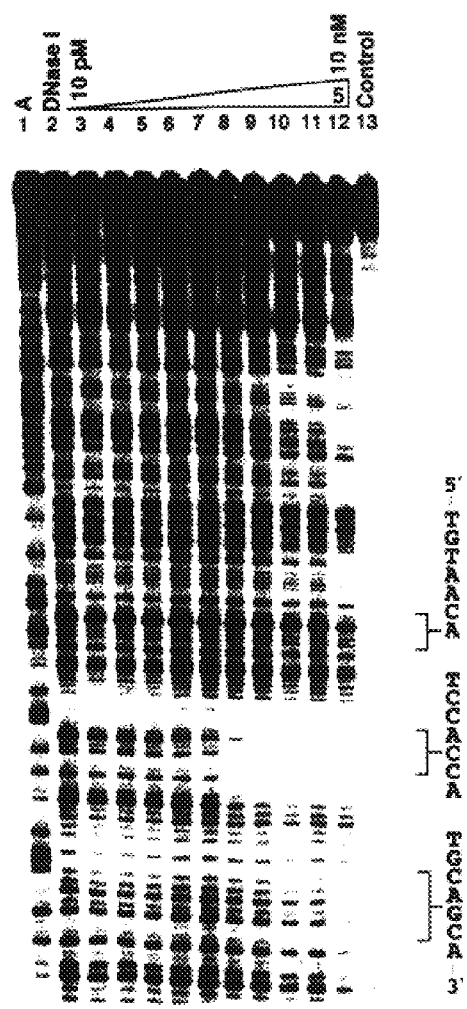
Figure 8C:
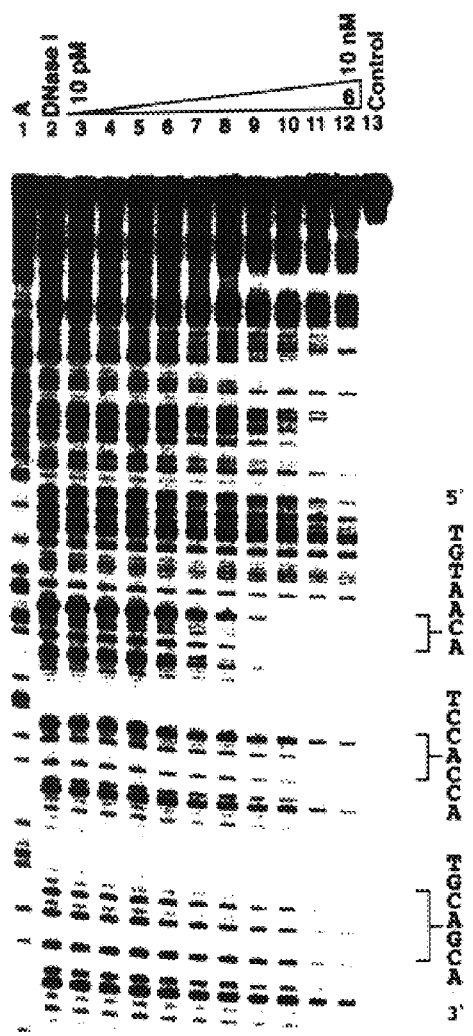
Figure 8D:
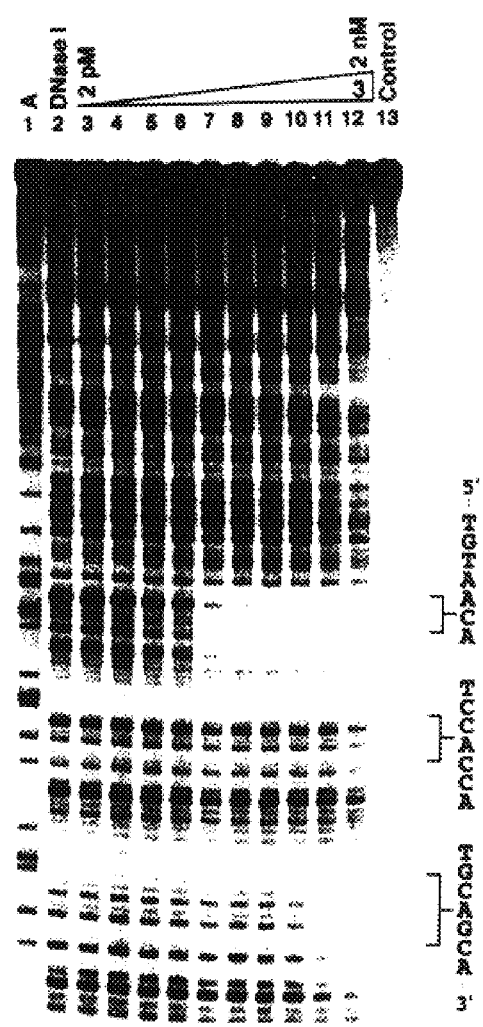

Quantitative DNase I footprint titration experiments (10 mM Tris-HCl, 10 mM KCl, 10 mM MgCl$_2$, 5 mM CaCl$_2$, pH 7.0, 24° C.) were carried out on the 282 bp, 3'-$^{32}$P end-labeled pJT2B2 EcoRI/PvuII restriction fragment which contains the three target sites 5'-TGCTGCA-3' (the HIV-1 target sequence), 5'-TGGTGGA-3', and 5'-TGTTTACA-3' (FIG. 7). These experiments reveal that the 5-γ-5 motif polyamide 1 binds the HIV-1 target sequence 5'-TGCTGCA-3' with a relatively low equilibrium association constant, K$_a$=8×10$^7$ M$^{-1}$, while no binding of the 5-γ-5 polyamide 2 to its target site 5'-TGGTGGA-3' is observed (K$_a$<5×10$^7$ M$^{-1}$). In contrast, 5-γ-5 polyamide 3 binds its Failure of Polyamide 1

The failure of polyamide 1 to bind the HIV-1 target sequence with high affinity is consistent with previous results. For example, the 4-γ-4 motif polyamides ImPyPyPy-γ-ImPyPyPy-β-Dp, ImPyPyPy-γ-PyPyPyPy-β-Dp and ImImPyPy-γ-ImImPyPy-β-Dp bind respective 6 base pair target sequences with subnanomolar affinity (Ka≧10$^{10}$ M$^{-1}$), while ImPyImPy-γ-ImPyImPy-β-Dp and ImImImIm-γ-PyPyPyPy-β-Dp bind respective target sequences with substantially lower affinity (Ka<10$^8$ M$^{-1}$). Based on these and additional results, the common feature of hairpin polyamides that bind with high affinity appears to be the placement of imidazole residues only at the first and second positions of polyamide subunits, counting from the N-terminal end, although in some cases substitution at the third position is tolerated. Imidazoles placed beyond the second position of a polyamide subunit are not positioned optimally for specific ligand-DNA contacts.

The 5-γ-5 polyamides 1, 2, and 3 are analogs of 4, 5, and 6, respectively, in which the β-alanine residues have been changed to pyrrole residues (FIG. 6). Polyamides 1 and 2, which have imidazole residues beyond the second position of a polyamide subunit, have equilibrium association constants for their match sites more than 100-fold lower than their β-alanine-substituted analogs 4 and 5, respectively (Table 1). Thus, the 2-β-2-γ-2-β-2 motif is essential for high-affinity recognition in these cases. In contrast, polyamide 3 having no imidazoles beyond the second position of a polyamide subunit binds its match site with an equilibrium association constant ~20-fold higher than its β-alanine-substituted analog 6 (Table 1).

The following model is consistent with our data: 1) In the 2-β-2-γ-2-β-2 polyamides 4 and 5 the flexible β-alanine linkers correctly position the imidazole residues following them for specific hydrogen bond contacts with their target guanine bases, while in 5-γ-5 polyamides 4 and 5 the analogous hydrogen bonds cannot form. 2) In contrast, for both 2-β-2-γ-2-β-2 polyamide 6 and polyamide 5-γ-5 3, the pyrroles beyond the second positions within polyamide subunits are correctly positioned, and 3 binds with lower affinity than 6 due to its greater conformational entropy.

These results indicate that the optimal binding positions, or "binding register," is different for imidazole and pyrrole residues, consistent with previous results which suggest that, for subunits composed entirely of rings (i.e. without β-alanine linkers), imidazole residues go out of register after 2–3 residues with substantial drops in affinity, while pyrrole residues go out of register after 5 rings with a gradual leveling of affinity before a substantial drop at 8 rings. Finally, these results indicate that the 2-β-2-γ-2-β-2 and 5-γ-5 motifs are complementary for recognition of 7 base pair sequences, with the optimal motif dependent on the sequence composition of the desired target site.

Relative Effects of Covalent Linkage with γ-Aminobutyric Acid

Equilibrium association constants for the "unlinked dimer motif" polyamides 7, 8, and 9 were measured to allow comparison with their corresponding γ-aminobutyric acid-linked polyamides 3, 4, and 6. Polyamides 4 and 6, which are composed of 2-γ-2 subunits, bind with ~6000-fold and ~1000-fold higher affinity, respectively, relative to their respective unlinked analogs 8 and 9. Polyamide 3, which is composed five-ring subunits, binds with ~100-fold higher affinity than its unlinked analog 7. The significantly larger increase in affinity upon linkage with γ-aminobutyric acid for 8 and 9 relative to 7 is consistent with the greater structural rigidity and consequently greater preorganization of 7.

Exact Binding Sites and Binding Orientations

Figure 9A:
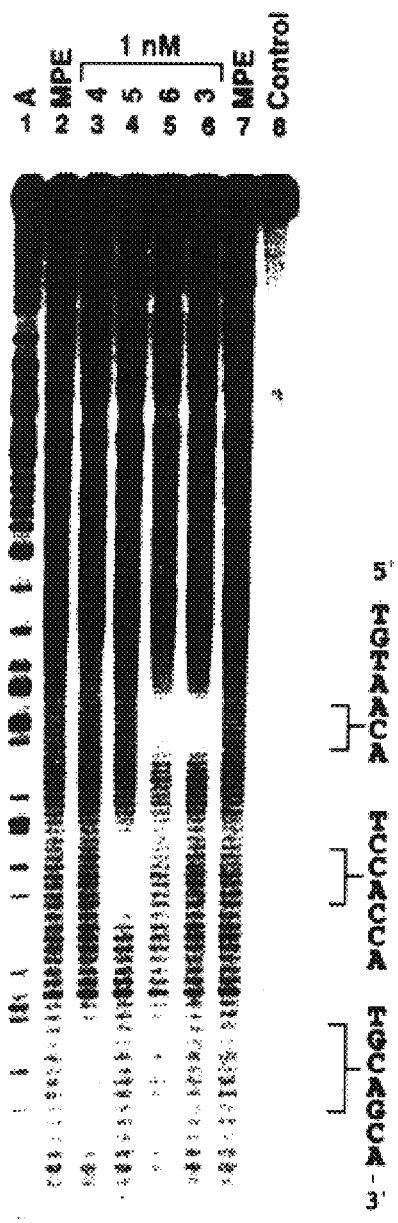
FIG. 9 is a representation of the results of a MPE.Fe$^{II}$ footprint experiment using polyamides 4, 5, 6, and 3 at 1 nM.
Figure 9B:
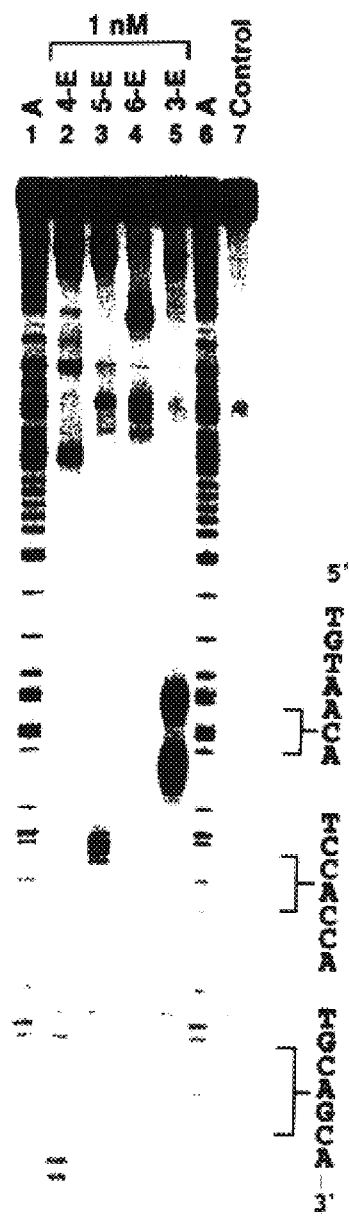

MPE.Fe$^{II}$ footprinting experiments carried out with the four polyamides 4, 5, 6, and 3, which have subnanomolar binding affinities, confirm that these compounds specifically bind their respective seven base pair match sites (FIGS. 9a and 10a). Affinity cleavage experiments were performed with the EDTA-polyamides 4-E, 5-E, 6-E, and 3-E to identify the location of the C-termini of these polyamides when bound to their target sites (FIGS. 6, 9b, 10b). The symmetric polyamides 4-E, 6-E, and 3-E produce cleavage patterns at both sides of their binding sites as expected, consistent with two distinct binding orientations (FIG. 9c). It appears that, in general, side-by-side polyamide-DNA complexes preferentially bind in the 5' to 3' (N- to C-terminus) orientation. Recent results of studies with hairpin polyamides are consistent with formation of 3' to 5'-oriented polyamide-DNA complexes, and suggest that such "reversed orientation" complexes typically have affinities ~10fold lower than analogous 5' to 3'-oriented complexes. Consistent with this trend, polyamide 4 binds the "reversed orientation" match site 5'-TCGTCGA-3' with an affinity ~10-fold lower than it binds the site 5'-TGCTGCA-3' (see footnote to Table 1). Inconsistent with this trend, however, the assymmetric polyamide 5-E produces a cleavage pattern (FIG. 10b) consistent with the polyamide binding preferentially in the reversed orientation (3' to 5', N- to C-terminus) as illustrated (for the parent compound 5) in FIG. 10c.

Effect of Physiological Salt and Temperature.

Quantitative DNase I footprinting experiments indicate that increasing the equilibration temperature from 24° C. to 37° C., and changing the solution conditions from standard polyamide assay conditions (10 mM Tris.HCl, 10 mM KCl, 10 mM MgCl$_2$, 5 mM CaCl$_2$, pH 7.0 at 24° C.) to conditions modeling those encountered within a typical mammalian cell (140 mM KCl, 10 mM NaCl, 1 mM MgCl$_2$, 1 mM spermine, pH 7.2) has little effect on polyamide binding affinity (Table 2).

TABLE 2

Equilibrium association constants ($M^a$) of polyamide 4 for its match site 5'-TGCTGCA-3'.[a]

| Buffer[b] | Temp. | 5'-aTGCTGCA-3' |
|---|---|---|
| A | 24° C. | $1.5 \times 10^{10}$ (0.3) |
|   | 37° C. | $8.4 \times 10^{9}$ (2.3) |
| B | 24° C. | $1.9 \times 10^{10}$ (0.6) |
|   | 37° C. | $1.1 \times 10^{10}$ (0.2) |

[a]Values reported are the mean values from at least three DNase I footprint titration experiments. The standard deviation for each value is indicated in parentheses.
[b]Buffer A: 10 mM Tris.HCl, 10 mM KCl, 10 mM MgCl$_2$, and 5 mM CaCl$_2$, pH 7.0 at 24° C.; Buffer B: 10 mM HEPES.HCl, 140 mM KCl, 10 mM NaCl, 1 mM MgCl$_2$, 1 mM spermine pH 7.2.

EXAMPLE 3

Binding of Polyamides to HIV-1 Promoter Sequences

Sequence-specific DNA-binding small molecules that can permeate human cells could potentially regulate transcription of specific genes. Pyrrole-imidazole polyamides were designed to bind DNA sequences proximal to binding sites for the cellular transcription factors TBP and LEF-1 utilized by HIV-1 for RNA synthesis. These synthetic ligands inhibit HIV-1 transcription in cell-free assays and virus replication in isolated human peripheral blood lymphocytes. The ability of small molecules to target predetermined DNA sequences located within RNA polymerase II promoters suggests a general approach for regulation of gene expression, as well as a mechanism for the inhibition of viral replication.

In Example 1, above, it was demonstrated that an eight-ring hairpin polyamide targeted to a specific region of the transcription factor TFIIIA binding site inhibits 5S RNA gene transcription by RNA polymerase III in Xenopus kidney cells. See also Gottesfeld, J. M., et al., Nature 387, 202 (1997). Using a similar approach, it has been found that polyamides can inhibit HIV-1 transcription in cell-free assays and viral replication in human lymphocytes.

The HIV-1 enhancer/promoter element contains binding sites for the cellular transcription factors Ets-1, LEF-1, NF-kB and SP1 along with a canonical TBP binding site (TATA element) and an initiator sequence (FIG. 11, taken from K. A. Jones & B. M. Peterlin Annu. Rev. Biochem. 63, 717 (1994)). Jones & Peterlin (1994) describe the composition of the HIV-1 enhancer region sequence. Binding sites for such transcription factors are not optimal polyamide target sequences because they are found in the promoters of many protein-coding genes. However, the sequences immediately flanking these transcription factor binding sites vary from gene to gene. In some cases, transcription factor flanking sequences are conserved for a particular gene providing an address for gene-specific targeting of common transcription factors. For example, the sequences immediately upstream and downstream from the HIV-1 TATA element are of the form 5'-WGCWGCW-3' (where W=A or T). At least one copy of the 5'-WGCWGCW-3' sequence is located adjacent to the HIV-1 TATA element in all sequences of the HIV 1 LTR found in the EMBL and Genbank data bases. K. Frech, R. Brack-Werner, T. Werner describe the common modular structure of viral LTR's. *Virology* 224, 256 (1996). However, the 5'-TGCTGCATATAAGCAGCT-3' (SEQ ID NO:3) TATA element is found only in strains and isolates of HIV-1 and in no other sequence in either data base. The activity of the HIV-1 promoter, and especially Tat-induced activity, is critically dependent upon this sequence. For example, point mutations in the TATA flanking region reduces activated transcription by 10-fold without effecting basal transcription. Tat-transactivation is essential for HIV-1 RNA synthesis and virus replication. B. Berkhout, K.-T. Jeang describe TAT induced expression of the HIV-1 long terminal repeat *J Virol.* 66, 139 (1992); H. S. Olsen, C. A. Rosen, describe contribution of the TATA motif to the TAT-mediated transcriptional activation of HIV-1 gene expression. *J Virol.*, 66, 5594 (1992). M. R. Sadaie, T. Benter, F. Wong-Staal, describe site directed mutagenesis of the 2-trans regulatory genes of HIV-1.

Figure 12:
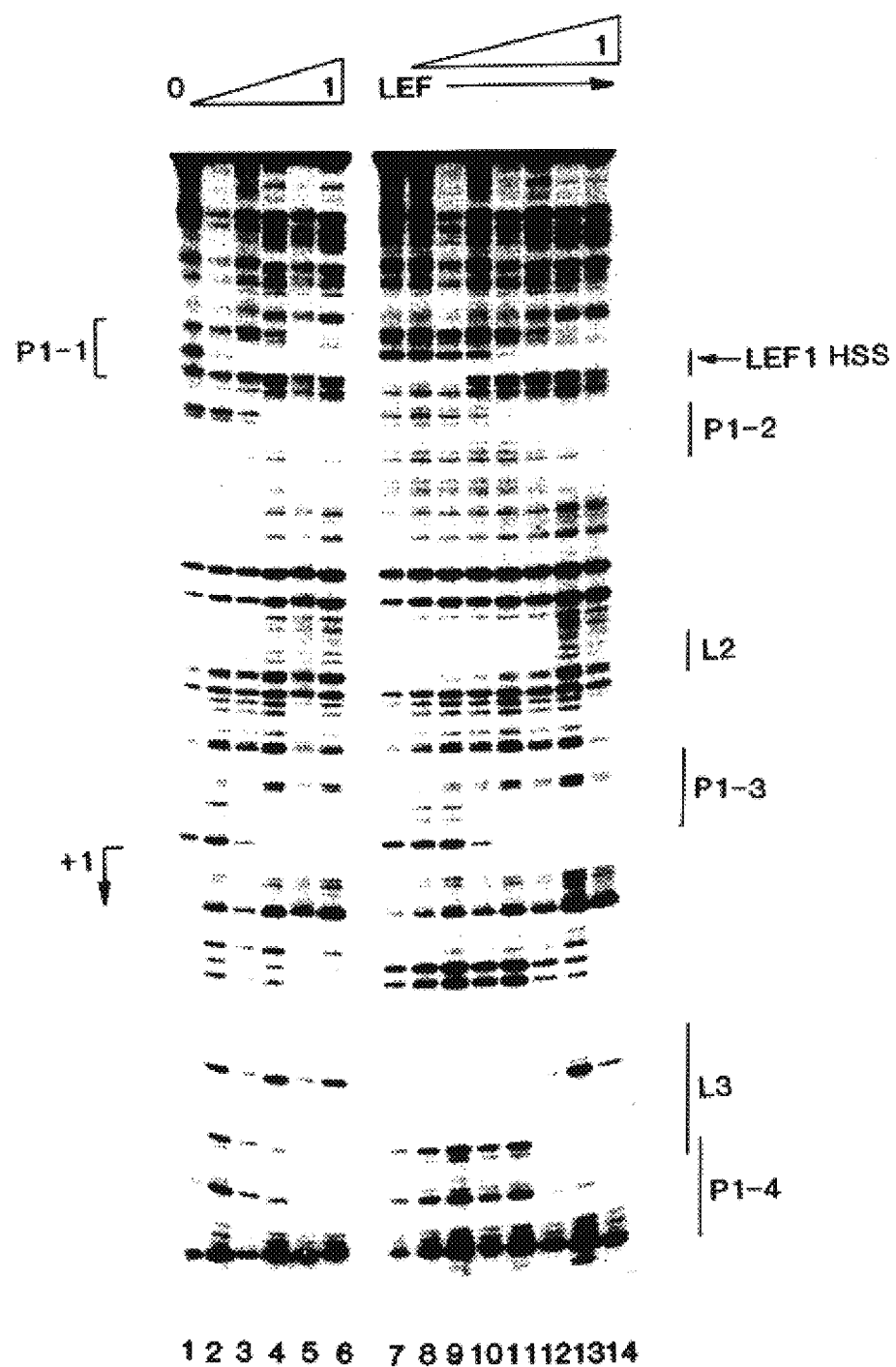
FIG. 12 is a representation of the results of an experiment demonstrating inhibition of LEF-1 binding to the HIV-1 enhancer by polyamide 1.

DNase footprint titrations showed that polyamide 1 bound to the site adjacent to the LEF-1 binding site with an apparent dissociation constant of 0.1 nM (FIG. 12, site P1-1). The labeled DNA was incubated with the following concentrations of polyamide 1 for 45 min prior to the addition of LEF-1 DBD to a final concentration of 8 nM (in the reactions of lanes 7 to 14): no polyamide (lanes 1 and 7); 10 pM (lanes 2 and 8); 30 pM (lane 9); 0.1 nM (lanes 3 and 10); 0.3 nM (lane 11); 1 nM (lanes 4 and 12); 3 nM (lanes 5 and 13); 10 nM (lanes 6 and 14). After a second incubation period of 45 min, the samples were subjected to DNase I digestion and analyzed by gel electrophoresis. The location of polyamide sites P1-1 to P1-4, LEF-1 sites L1–L3, the LEF-1 DNase hypersensitive (HSS) site and the start-site for transcription (+1) are shown along the side the autoradiogram. Three additional potential binding sites for polyamide 1 are present in the HIV-1 promoter (5'-TGTACT-3') and coding sequence (5'-AGATCT-3') and polyamide 1 also binds these sequences (P1-2 to P1-4, FIG. 12). In agreement with previous published studies, recombinant LEF-1 protein (recombinant DNA binding domain) bound to its target site with an apparent dissociation constant of 1.5 nM (as determined by DNase footprint titrations). Two additional LEF-1 sites are found in the HIV-1 promoter and coding sequences (sites L2 and L3, FIG. 12). Importantly, polyamide 1 proved to be an effective inhibitor of LEF-1 binding to each of these sites with a Ki of 0.1 nM for the enhancer site. Importantly, inhibition was observed either when the polyamide was incubated with the DNA before adding LEF-1 or after preincubation of the DNA with LEF-1. In similar DNase footprinting experiments, the mismatch polyamides did not inhibit LEF-1 binding even at a 100-fold higher concentration that that needed for inhibition by polyamide 1.

Based on the results described above, it was expected that polyamide inhibition of LEF-1 binding would inhibit LEF-1-dependent transcription in an appropriate in vitro assay system. The effects of polyamide 1 and mismatch polyamide 2 on HIV-1 transcription were tested in an in vitro system consisting of a cell-free extract prepared from cultured human lymphoid H9 cells. This whole-cell extract contains high levels of LEF-1 protein but supports only low levels of transcription, suggesting a limitation for other transcription components in this extract. The H9 cell extract was supplemented with the HeLa cell-derived nuclear extract in order to obtain high levels of transcription. The H9 cell extract stimulates HIV-1 transcription ~2.5 to 3-fold over the level of transcription observed with the HeLa extract alone and immunodepletion of LEF-1 protein from the H9 extract abolishes this activated transcription. Polyamide 1 is an effective inhibitor of HWV-1 transcription in this system: 50% inhibition of transcription is obtained in polyamide titration experiments between 10 and 30 nM polyamide 1 in the reaction. Polyamide 1 fails to inhibit HIV-1 transcription in the LEF-1-depleted extract or with the HeLa extract alone. Similarly, LEF-1 depletion had no effect on CMV MIEP transcription. The effects of the mismatch polyamide 2 on HIV-1 and CMV transcription were tested as additional controls. No potential binding sites for either polyamide 1 or 2 are present in the CMV MIEP sequence. As expected, polyamide 1 fails to inhibit CMV transcription and mismatch polyamide 2 fails to inhibit either HIV-1 or CMV transcription.

Notably, HIV-1 transcription was not inhibited by polyamide 1 at concentrations as high as 1 μM even though binding sites for the polyamide occurred near the start-site for transcription (−2 to −7) and within the transcribed sequence (+20 to +25). A polyamide was designed and synthesized in inhibition studies with the human cytomegalovirus (CMV) immediate early promoter. A potential binding site for polyamide 3 (FIG. 1 above) is located near the start-site for CMV transcription. Similar to our results with polyamide 1 and HIV-1 transcription, polyamide 3 had no effect on CMV transcription in our reconstituted assay system. These results with both the HIV-1 and CMV promoters suggest that RNA polymerase II can initiate transcription and read through DNA bound with a polyamide in the minor groove. Thus, a polyamide must interfere with an essential DNA-binding protein to be an inhibitor of transcription.

Another well-studied minor groove DNA-binding protein is the TATA-box binding protein [TBP]. X-ray crystallographic studies of the TBP-DNA complex have clearly shown that TBP binds DNA in the minor groove and that binding results in a severe distortion of the DNA duplex (unwinding and bending).

Since TATA elements are found in many protein-coding genes (with the exception of the so-called "housekeeping" genes), the TATA element itself is not a good candidate for a polyamide target sequence. However, the sequences immediately flanking TATA boxes are unique to each individual gene with little or no homology between genes. Thus, by analogy with our LEF-1 results, it would be expected that targeting the sequence immediately adjacent to a TATA element with a polyamide might inhibit TBP binding and thus inhibit transcription of that gene by interfering with assembly of the RNA polymerase II transcription complex. Note that it is the binding of the TBP subunit of TFIID that nucleates the assembly of the RNA polymerase II transcription machinery for TATA-containing genes.

As a model system the polyamide 1 binding site was introduced immediately adjacent to the HIV-1 TATA element by oligonucleotide-directed mutagenesis. Thus the TATA region sequence was changed from 5'-CATATAAGCAGCT-3' (WILD-TYPE) (SEQ ID NO:4) to 5'-CATATAAGTACTT-3' (SEQ ID NO:5) (MUTANT, polyamide I site underlined).

Figure 13:
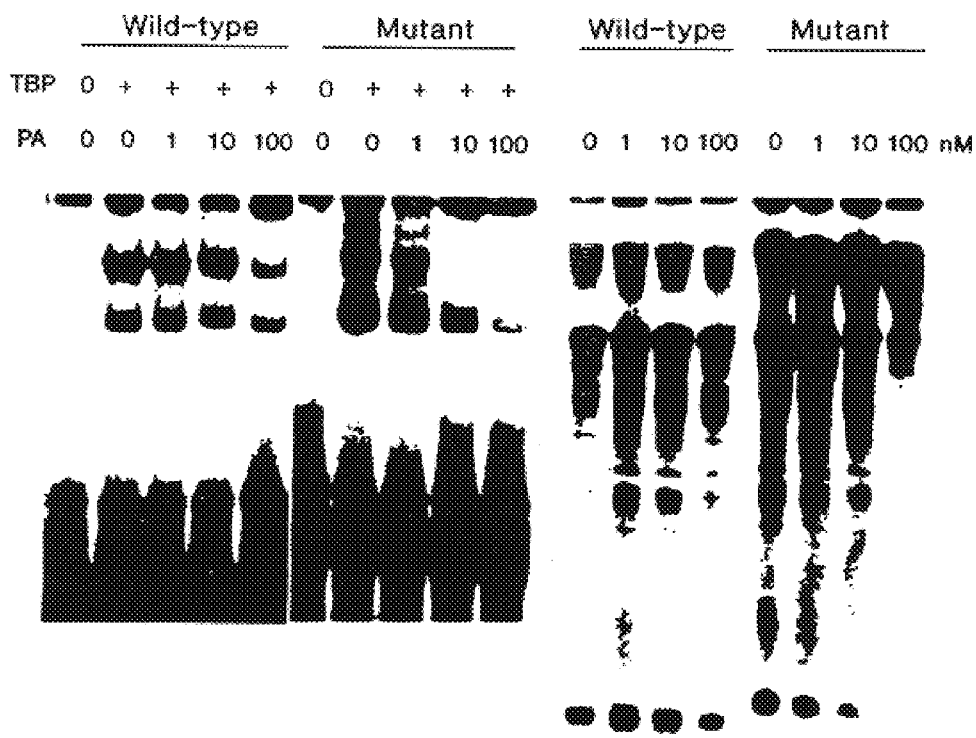
FIG. 13 is a representation of the results of an experiment demonstrating binding to wild type and mutant forms of the HIV-1 enhancer by polyamide 1.

The effect of the polyamide on the formation and stability of the TBP-DNA complex was determined using a gel mobility shift assay. As observed in previous gel mobility shift assays with recombinant TBP, both monomer and dimer TBP-DNA complexes are observed with both the wild-type and mutant TATA-box DNA fragments. Polyamide 1 inhibited TBP binding to the "mutant" HIV-1 promoter DNA probe but did not significantly inhibit TBP binding to the wild-type HIV-1 promoter probe (FIG. 13A). Similarly, polyamide 1 inhibited basal transcription from the "mutant" HIV-1 promoter but not from the wild-type promoter in a reconstituted transcription system containing a HeLa cell nuclear extract (FIG. 13B, below). Approximately 70% inhibition of basal RNA polymerase II-mediated transcription was observed in this assay with polyamide I at a concentration of 100 nM. Additionally, neither of the mismatch polyamides inhibited TBP binding or transcription.

Figure 14A:
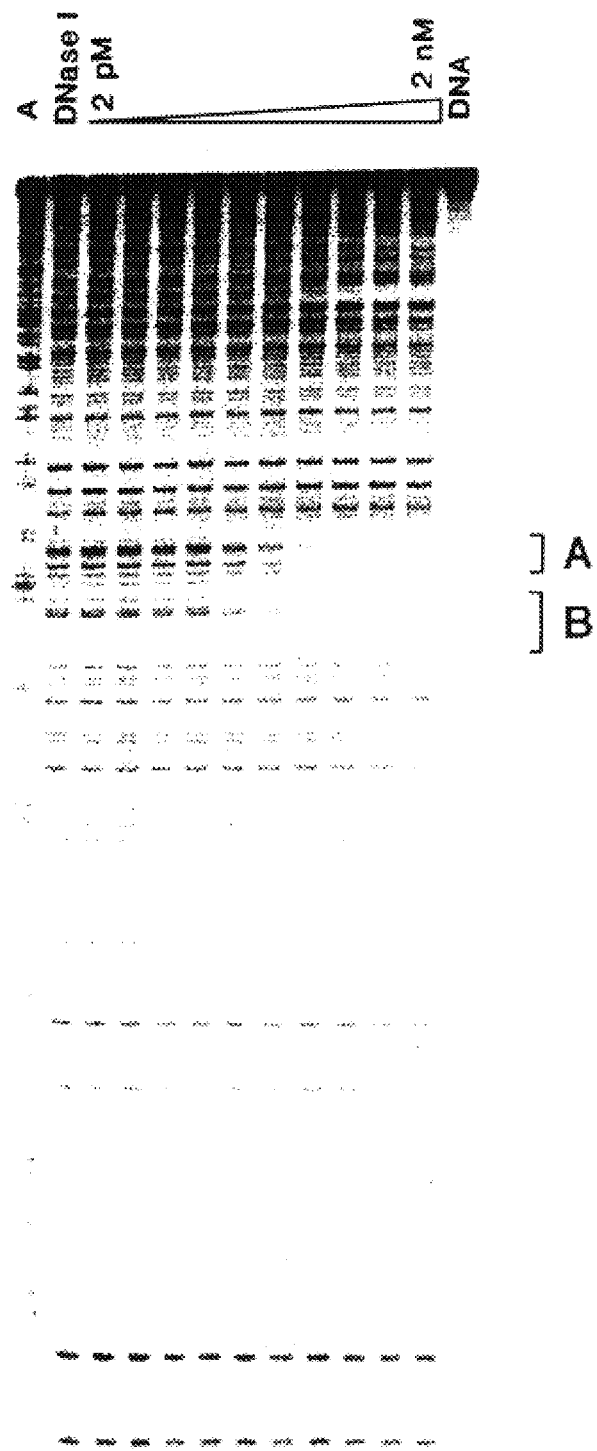
FIG. 14 is a representation of the results of an DNase footprint experiment demonstrating binding to the HIV-1 enhancer of the polyamide ImPy-β-ImPy-γ-ImPy-β-ImPy-β-Dp, also called HIV-1.
Figure 15:
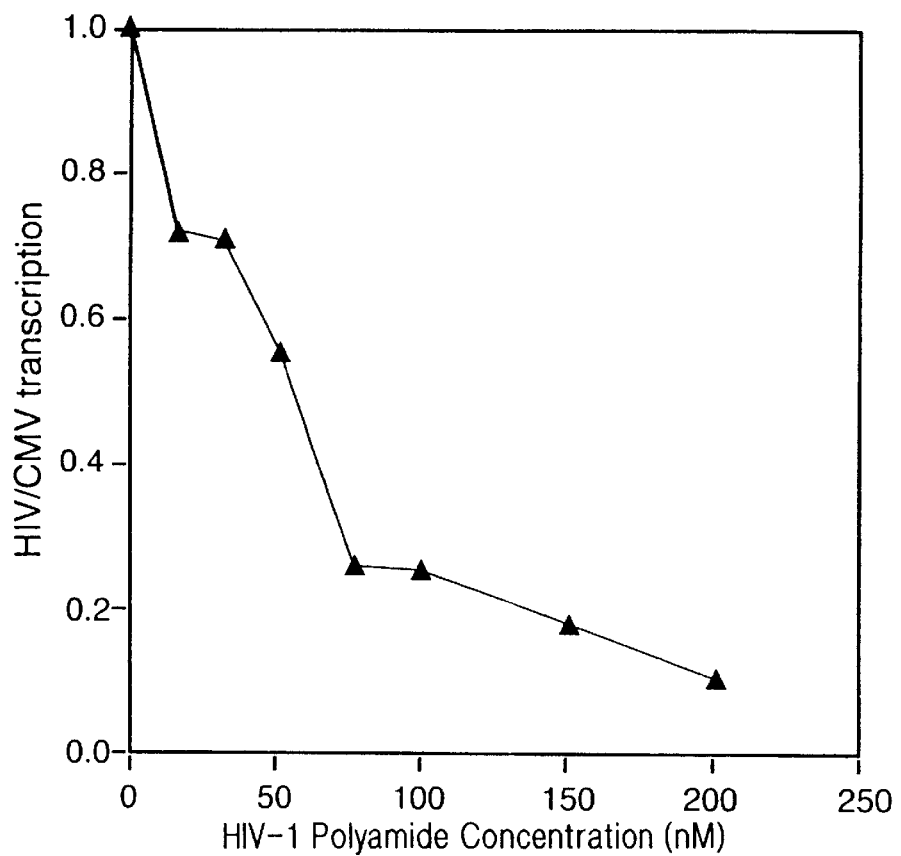
FIG. 15 is a representation of the inhibition of HIV-1 transcription by the polyamide ImPy-β-ImPy-γ-ImPy-β-ImPy-β-Dp, also called HIV-1.

Based on these results, another polyamide was designed and synthesized to specifically target the HIV-1 TATA element as described in Example 2 (FIG. 14, below): As shown below, this polyamide (ImPy-β-ImPy-γ-ImPy-β-ImPy-β-Dp, called HIV-1 in FIGS. 14–116 and polyamide 1 in FIGS. 18–24) was designed to recognize the sequences immediately 5' and 3' to the HIV-1 TATA element. The recognition sites for polyamide HIV-1 are of the form 5'-WGCWGCW-3" (where W=A or T). Since a pyrrole-pyrrole pair can recognize either an A-T base pair or a T-A base pair, polyamide HIV-1 will recognize both the 5' and 3' flanking sequences of the HIV-1 TATA element. Binding of the polyamide was confirmed by DNase I footprinting and an apparent dissociation constant of 0.05 nM ($K_a = 2 \times 10^{10}$ $M^{-1}$) was determined for both sites (FIG. 14). This polyamide inhibits HIV-1 transcription in an in vitro transcription assay with the lymphoid cell nuclear extract and a wild-type HIV-1 promoter but not transcription of a control template lacking the binding site (the CMV immediate early promoter). A quantitative representation of the data is shown in FIG. 15. Fifty percent inhibition of HIV-1 transcription is observed at approximately 50 nM polyamide in the reaction. This concentration corresponds to only a 16-fold excess of polyamide over specific binding sites in the HIV-1 plasmid DNA (3 nM).

A corresponding control polyamide was also synthesized (ImIm-β-ImIm-γ-PyPy-β-PyPy-β-Dp, named HIV-2 in FIG. 16 and polyamide 2 in FIGS. 18–24). This polyamide differs from the HIV-1 polyamide only in the placement of the imidazole and pyrrole amino acids and recognizes the TATA box region of the HIV-1 LTR with at least 100-fold reduced affinity relative to the HIV-1 polyamide ($K_a = 2 \times 10^8$ $M^{-1}$). In FIG. 16, the structures of polyamides HIV-1, ImPy-β-ImPy-γ-ImPy-β-ImPy-β-Dp and HIV-2, ImIm-β-ImIm-γ-PyPy-β-PyPy-β-Dp, are shown along with polyamide binding models for the HIV-1 TATA box region. The filled and unfilled circles represent imidazole and pyrrole rings, respectively, the curved line represents γ-aminobutyric acid, and the diamond represents β-alanine. Single hydrogen bond mismatches are highlighted.

As noted above, the sequences immediately flanking TATA boxes are unique to each individual gene with little or no homology between genes. The sequences immediately 5' and 3' to the HIV-1 TATA element are of the form of 5'-WGCQGCW-3' (where W=A or T). A data base search revealed that at least on copy of the 5'-WGCQGCW-3' sequence is located adjacent to the HIV-1 TATA element in all sequences of the HIV-1 LTR found in the EMBL and GenBank data bases. Furthermore, the 5'-TGCTGCATATAAGCAGCT-3' (SEQ ID NO:3) TATA element and the other prevalent HIV-1 TATA element (5'-TGCTGCATAAAAGCAGCC-3') (SEQ ID NO:6) are found only in the various strains and isolates of HIV-1 and in no other reported sequence in either GenBank or the EMBL data base.

These polyamides were next used in DNase I footprinting experiments and gel mobility shift assays with TBP and an HIV-1 LTR restriction fragment or TATA box oligonucleotides (as described above). As expected, the match polyamide HIV-1 inhibited TBP binding to the HIV-1 TATA element but the mismatch polyamide HIV-2 did not inhibit TBP binding to this same DNA fragment (FIG. 19A). DNase I footprint titrations of polyamides HIV-1 and -2 were preformed in the presence or absence of recombinant human TBP (rhTBP) (− or +TBP). A radiolabeled HIV-1 LTR restriction fragment was incubated for 30 min with the following concentrations of polyamides prior to addition of rhTBP where indicated: no polyamide, lanes 2, 6, 10, 14; 2.5 nM polyamide, lanes 3, 7, 11, 15; 5 nM, lanes 4, 8, 12, 17; 10 nM, lanes 5, 9, 13, 17. After an additional 30 min incubation, samples were digested with DNase I. G+A chemical sequencing reactions are shown in lanes 1 and IS. The extent of the footprints generated by polyamide HIV-1 and TBP, respectively, are indicated at the sides of the autoradiogram.

Complete inhibition of TBP binding was observed at a polyamide concentration of 2.5 nM, which represents only a five-fold excess of polyamide over DNA binding sites in this assay. The HIV-1 polyamide did not inhibit TBP binding to an oligonucleotide corresponding to the TATA box region of the adenovirus major late promoter (data not shown). The half-life of the HIV-1 polyamide was determined in an experiment in which the polyamide-DNA complex was first formed and then challenged with a large molar excess of unlabeled DNA. Samples were taken for digestion with DNase after various incubation times and the apparent half-life of the HIV-1 polyamide-DNA complex is in excess of 2.5 hours.

FIG. 17 illustrates the binding of several classes of polyamides to the DNA sequence adjacent to the HIV-1 TATA box (FIG. 17, sections 1a–1c) and adjacent to the Ets-1/ LEF-1 binding sites. As described above, the polyamide HIV-1 (FIG. 17, 1a) is a hairpin molecule that binds to a seven base pair sequence of the form 5'-WGCWGCW-3' (where W=A or T). A longer twelve base pair sequence can be bound by an antiparallel dimer of the non-hairpin polyamide ImPy-β-PyPyPyPy-β-ImPy-β-Dp (FIG. 17, 1b). An even longer sixteen base pair sequence can be bound by an antiparallel dimer of the hairpin polyamide ImPy-β-ImPy-β-PyPyPyPy-β-ImPy-β-ImPy-β-Dp (FIG. 17, 1c). Similarly, a six base pair sequence between the Ets-1 binding site and the LEF-1 binding site can be bound by the polyamide ImPyPyPy-γ-ImPyPyPy-β-Dp (FIG. 17, 2a). The same sequence plus a portion of the LEF-1 binding site extending a total of nine base pairs can be bound by the polyamide ImPy-β-ImPyPyPy-γ-ImPyPyPy-β-PyPy-β-Dp (FIG. 17, 2b).

EXAMPLE 4

Inhibition of TBP Binding by Polyamide Ligands

Figure 18A:
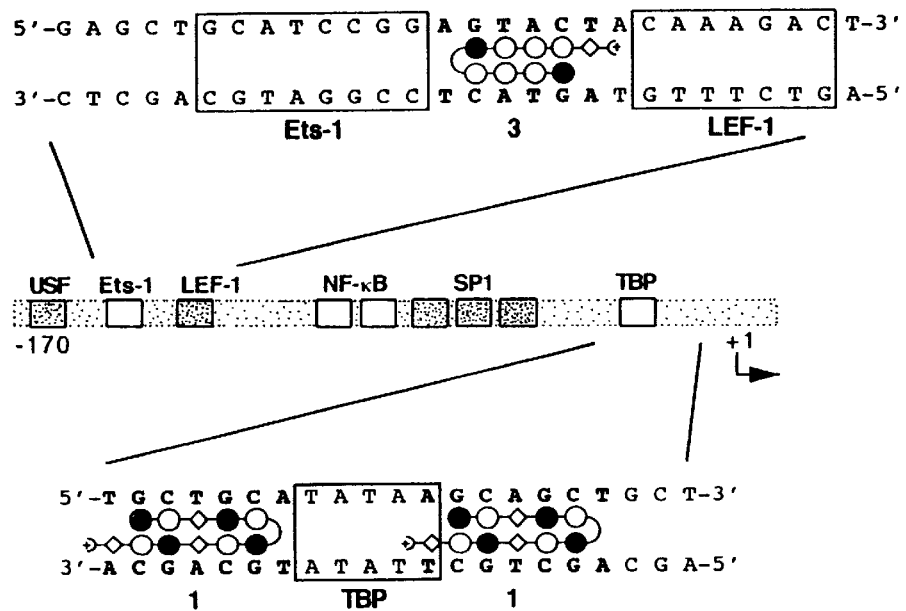
FIG. 18 is a representation of the HIV-1 promoter and DNA-binding sites for polyamide hairpins designed to target the HIV-1 promoter.
Figure 18B:
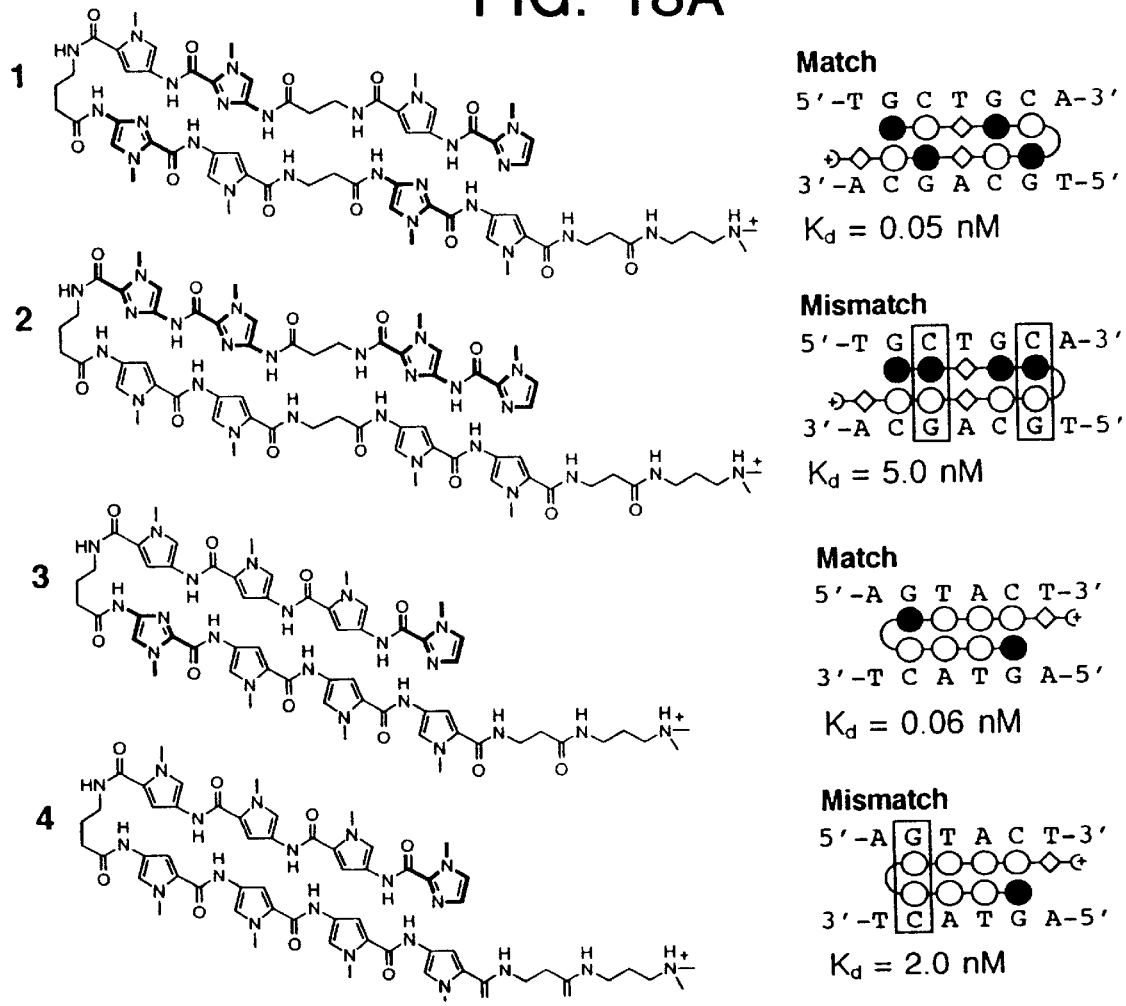

FIG. 18 schematically depicts the HIV-1 promoter and DNA-binding sites for polyamide hairpins designed to target the HIV-1 promoter. In FIG. 18A, the DNA binding sites for hairpin polyamides designed to target the HIV-1 enhancer and promoter are illustrated, showing the binding of the polyamide ImPyPyPy-γ-ImPyPyPy-β-Dp, here designated polyamide 3, also labeled above as polyamide 1 in FIGS. 1–4 and 12–13. As before, in the binding model illustration, the shaded and unshaded circles represent imidazole (Im) and pyrrole (Py) rings, respectively, the curved lines represent γ-aminobutyric acid (γ), and the diamonds represent β-alanine (β). The shaded bar schematic of the HIV-1 enhancer and promoter shows nucleotide positions −170 to the transcription start site at +1. The binding sites for the transcription factors USF, Ets-1, LEF-1, NF-κB, SP1 and TFIID (TBP) are indicated. The binding sites for polyamides 1, called HIV-1 above, and 3, called HIV-2 above, are indicated. The structures of polyamides ImPy-β-ImPy-γ-ImPy-β-ImPy-β-Dp (1), ImIm-β-ImIm-γ-PyPy-β-PyPy-β-Dp (2), ImPyPyPy-γ-ImPyPyPy-β-Dp (3), and ImPyPyPy-γ-PyPyPyPy-β-Dp (4), are shown in FIG. 18B, where Dp=dimethyaminopropylamide. Binding models and measured dissociation constants ($K_d$) are shown. Mismatched base pairs are highlighted.

It is known that binding of the TBP subunit of TFIID in the minor groove nucleates assembly of the RNA polymerase II transcription machinery for TATA-containing genes. In general. S. K. Burley, R. G. Roeder describe the biochemistry and structural biology of the transcription factor TFIID *Ann. Rev. Biochem.* 65, 769 (1996); C. P. Verrijzer, R. Tjian describe TAFS which mediate transcription activity and promoter selectivity *TIBS* 21, 338 (1996); R. G. Roeder describes the role of general initiation factors in transcription by RNA polymerase II *TIBS.*, 21, 327 (1996).

According to the pairing rules for DNA recognition, the 5'-WGCWGCW-3' sequence adjacent to the HIV-1 TATA element is targeted by hairpin polyamide 1 having sequence composition ImPy-β-ImPy-γ-ImPy-β-ImPy-β-Dp (FIG. 18). The imidazole-pyrrole pair (Im/Py) targets a G.C base pair and Py/Im targets C.G. Since the β/β pairing recognizes both A.T and T.A base pairs polyamide 1 is expected to bind both the 5' and 3' flanking sequences of the HIV-1 TATA element (FIG. 18A). White, S., Baird, E. E. & Dervan, P. B. describes the pairing rules for recognition in the minor groove of DNA by pyrrole-imidazole polyamides. *Chem. & Biol.* 4, 569–578 (1997); Swalley, S. E., Baird, E. E. & Dervan, P. B. describe the sequence specificity of the β/β pairing *Chem Eur. J.* 3, 1600 (1997). Quantitative footprint titration experiments reveal that polyamide 1 binds both TBP sites as well as a 5'-AGCTGCA-3' match site overlapping the binding site for Ets-1 with an equilibrium dissociation constant ($K_d$) of 0.05 nM (FIG. 19A, lanes 3–5). For DNase I footprinting a 400-bp restriction fragment containing the HIV-1 enhancer and promoter regions was isolated from pHIV LTR-CAT plasmid DNA (obtained from Dr. K. A. Jones of The Salk Institute, La Jolla, Calif.) (P. L. Sheridan et al., describe the sequence composition of the plasmid pHIV LTR-CAT *Genes Dev.* 9, 2090 (1995)). Labeled DNA was incubated with polyamide (45 minutes) and digested with DNase I under single-hit conditions.

Regions of polyamide protection were determined by analysis of the digestion products on a 6% denaturing polyacrylamide sequencing gel. Storage phosphorimage analysis of the data was used to obtain dissociation constants for the binding reactions (using Kodak Storage Phosphor Screens and a Molecular Dynamics SF PhosphorImager). Recombinant human TBP (rhTBP) was obtained from Promega and was used in footprinting and gel mobility shift experiments as recommended. The reaction mixtures also contained 100 ng of poly dG-poly dC per 10 μL gel shift reaction or 50 μL footprinting reaction. For gel mobility shift assays, 6% polyacrylamide gels (20:1, acrylamide to bisacrylamide) contained 44 mM Tris-borate, pH 8.3, 1 mM EDTA, 4 nM $MgCl_2$ and 0.02% (v/v) NP-40. The same buffer was used for electrophoresis of 1 mm thick gels at 15 volts/cm for 2 hours at 4° C.

The HIV-1 TATA region double-stranded oligonucleotide, used as probe for the gel assay, had the top-strand sequence: 5'-CGTCCCTCAGATGCTGCATATAAGCAGCTGCTT TTTGCCTGTACTGGGTC-3' (SEQ ID NO:7) , and the complementary bottom-strand sequence. The adenovirus major late promoter TATA region oligonucleotide has the top-strand sequence 5'-GATCGGGGCTATAA AAGGGGGTGGG3' (SEQ ID NO:8), and the complementary bottom-strand sequence. Each DNA strand (50 ng) was labeled in separate reactions with $\gamma\text{-}^{32}\text{P}$-ATP and T4 polynucleotide kinase and the double-stranded oligonucleotides were prepared by annealing equal molar amounts of the two complementary strands. Gel shift reactions contained 15 fmol of double stranded oligonucleotide (1.5 nM) and, where indicated in the figure legends, 50 pg of rhTBP (0.14 nM). Footprinting reactions contained the HIV-1 DNA probe (0.5 nM), and polyamide and 5 ng of rhTBP (3 nM) as indicated.

The inhibition of TBP binding to the HIV-1 TATA element by polyamide 1 is shown in FIG. 19. FIG. 19A shows DNase I footprint titrations of polyamides 1 and 2 in the presence or absence of rhTBP. The radiolabeled HIV-1 LTR restriction fragment was incubated for 30 min with the following concentrations of polyamide 1 or 2 prior to addition of rhTBP here indicated (+): no polyamide, lanes 2, 6, 10, 14; 2.5 nM polyamide, lanes 3, 7, 11, 15; 5 nM, lanes 4, 8, 12, 16; 10 nM, lanes 5, 9, 13, 17. After an additional 30 min incubation, samples were digested with DNase I. G+A chemical sequencing reactions are shown in lanes 1 and 18. The location of the transcription start site, and the extent of the footprints generated by polyamide 1 and TBP (+1), are indicated at the sides of the autoradiogram. Binding sites for polyamide 1 are located adjacent to the TATA element and additional sites are found overlapping the binding site for the transcription factor Ets-1 (FIG. 18A) and in the vector DNA sequence (upstream of position −170).

A mismatch control polyamide ImIm-β-ImIm-γ-PyPy-β-PyPy-β-Dp (2) which differs only in the placement of imidazole and pyrrole amino acids binds the HIV-1 TATA box region with 100-fold reduced affinity relative to polyamide 1. TBP binds the HIV-1 TATA element with a $K_d$ of ~1–3 nM. DNase footprinting assays reveal that polyamide 1 inhibits TBP binding at a concentration of 2.5 nM, which represents only a five-fold excess of polyamide over DNA binding sites in this assay (FIG. 19A., lane 7). Mismatch polyamide 2 fails to inhibit TBP binding (FIG. 19A., lanes 15–17).

A gel mobility shift assay which distinguishes the TBP-DNA complex from free DNA and polyamide-DNA complexes was carried out. The results are illustrated in FIG. 19B. Radiolabeled HIV-1 TATA box (lanes 1–5 and 11–15) or adenovirus major late promoter TATA box duplex oligonucleotides (lanes 6–10) (11) were incubated with the following concentrations of polyamide prior to addition of rhTBP, where indicated (+): no polyamide, lanes 1, 2 ,6, 7, 11, 12; 50 nM polyamide, lanes 3, 8, 13; 100 nM, lanes 4, 9, 14; 200 nM, lanes 5, 10, 15. After an additional 30 min incubation, samples were subjected to electrophoresis. The positions of free DNA probes (F) and the monomer and dimer TBP-DNA complexes (B) are indicated alongside the figure. Polyamide 1 inhibits TBP binding to a double stranded oligonucleotide corresponding to the HIV-1 TATA box region, while no inhibition is observed for control polyamide 2 (FIG. 13B). Additionally, polyamide 1 does not inhibit TBP binding to the TATA box region of the adenovirus major late (AdML) promoter (5'GOOQGCTATAAAAGGGGGT-3') (SEQ ID NO:9) which contains mismatch (underlined) flanking sequences. The half-life of the polyamide 1-DNA complex was determined by competition experiments to be in excess of 2.5 hours.

EXAMPLE 5

Inhibition of LEF-1 Binding

Polyamides were designed and synthesized to target a sequence adjacent to the binding site for LEF-1, a cellular transcriptional activator used by HIV-1. LEF-1 is a member of the HMG family of minor-groove binding proteins. J. J. Love, et al. describe the structure of the LEF-1-DNA complex. *Nature* 376, 791 (1995); J. Kim, F. Gonzales-Scarano, S. Zeichner, J. Alwine. Describe replication of HIV-1 containing linker substitution mutations in the −201 to −130 region of the long terminal repeat *J. Virol* 67, 1658 (1993);. In addition to acting as an architectural transcription factor, LEF-1 possesses a strong trans-activation domain and has been shown to be essential for viral transcription and replication in lymphoid cells. The LEF-1 binding site is immediately, flanked on one side by the sequence 5'-AGTACT-3'. According to the polyamide pairing rules, this sequence should be bound by hairpin polyamide 3 of sequence composition ImPyPyPy-γ-ImPyPyPy-β-Dp which has already been characterized. Trauger, J. W., Baird, E. E. Dervan, P. B. describes the recognition of DNA by designed ligands at subnanomolar concentrations. *Nature* 382, 559–561 (1996).

Quantitative footprint titration experiments reveal that polyamide 3 binds the 5'-AGTACT-3' site adjacent to the LEF-1 binding site with $K_d$ of about 0.06 nM. (site P3-1 in FIG. 20A). DNase I footprint titration experiments were performed as described for TBP above. Three additional polyamide 3 binding sites present in the HIV-1 enhancer/promoter restriction fragment were bound with $K_d$ about 1 nM: 5'-TGTACT-3' (located at −7 to −2, P3-3 in FIG. 20A); 5'-AGATCT-3' (located at +20 to +25, P3-4 in FIG. 20A) and a single base mismatch site 5'-TCTACA-3' (located at −106 to −111, P3-2 in FIG. 20A). DNase I footprinting failed to detect any high affinity sites for mismatch polyamide 4 on the HIV-1 enhancer/promoter fragment (FIG. 20B). Three sites on the HIV-1 promoter/enhancer restriction fragment are bound by the 86-amino acid LEF-1 DNA binding domain (DBD), sites L1, L2, and L3 (FIG. 20A) with $K_d$=1.4, 5.8, and 4.9 nM, respectively. Recombinant LEF-1 protein containing the 86 amino acid DNA-binding domain (DBD) was the generous gift of J. Love (Scripps Research Institute) and was expressed and purified as described. J. J. Love, et al. describe the structure of the LEF-1-DNA complex. *Nature* 376, 791 (1995). LEF-1 was diluted into a buffer containing 10 mM Hepes-OH, pH 7.5, 100 mM KCl, 1 mM dithiothreitol, 1 mM $MgCl_2$, 10% (v/v) glycerol and 250 µg/mL BSA.

DNA binding reactions were performed in the same buffer (without BSA) and also contained 250 ng of poly dG-poly dC and the HIV-1 DNA probe at 50 pM in a final volume of 50 µl. For assessing LEF-1 occupancy by DNase I footprinting, the intensity of a protein-induced DNase I hypersensitive site was used as a hallmark of LEF-1 binding.

The LEF-1 footprint at site L1, characterized by a marked DNase I hypersensitive site (HSS), clearly changes to the polyamide footprint in the presence of match polyamide 3. LEF-1 binding is inhibited 50% at a polyamide 3 concentration of approximately 60 pM. Thus, polyamide 3 located in the minor groove immediately adjacent to site L1 inhibits LEF-1 DBD binding to this site. Polyamide 3 only inhibits LEF-1 binding to sites L2 and L3 at markedly higher polyamide concentrations (3 nM and above, lanes 13–14). Inhibition was observed either by adding the polyamide to the DNA before LEF-1 or after preincubation of the DNA with LEF-1, consistent with the relative dissociation constants for the two binding reactions. Mismatch polyamide 4, which binds to the 5'-AGTACT-3' sequence with >100-fold reduced affinity, fails to inhibit LEF-1 binding (FIGS. 20B & C).

Figure 20A:
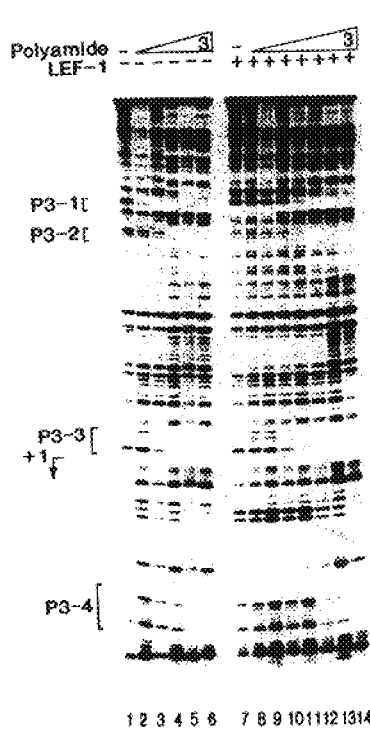
FIG. 20 is a representation of the results of a footprint experiment comparing the binding of polyamides and LEF-1.
Figure 20B:
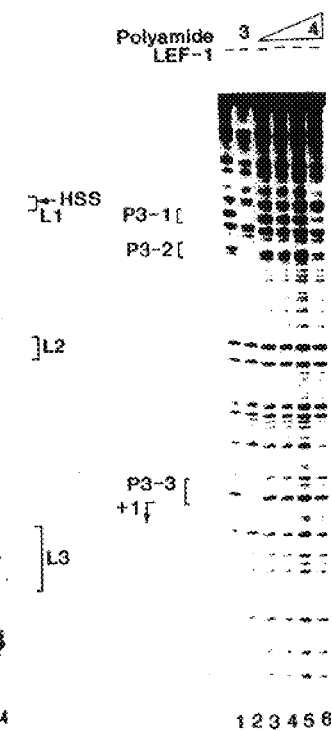
Figure 20C:

The inhibition of LEF-1 binding to the HIV-1 enhancer by polyamide 3 is shown in FIG. 20. In FIG. 20A, the $3'$-$^{32}P$ end-labeled HIV-1 LTR restriction fragment was incubated with 10 pM–10 nM polyamide 1 for 45 min prior to the addition of LEF-1 DBD to a final concentration of 8 nM (lanes 7 to 14). After an additional 45 min, the samples were subjected to DNase I digestion and analyzed by gel electrophoresis. The polyamide concentrations were: no polyamide (lanes 1 and 7); 10 pM (lanes 2 and 8); 30 pM (lane 9); 0.1 nM (lanes 3 and 10); 0.3 nM (lane 11); 1 nM (lanes 4 and 12); 3 nM (lanes 5 and 13); 10 nM (lanes 6 and 14). In FIG. 20B, mismatch polyamide 4 does not bind to the the HIV-1 enhancer/promoter. The labeled DNA was incubated with the following concentrations of polyamides for 45 min: no polyamide (lane 1), 10 nM polyamide 3 (lane 2), 1, 3, 10, and 60 nM polyamide 4 (lanes 3–6). In FIG. 20C, mismatch polyamide 4 does not inhibit LEF-1 binding to the HIV-1 enhancer/promoter. The labeled DNA was incubated with the following concentrations of polyamide 4 for 45 min prior to the addition of LEF-1 DBD: 1 nM (lanes 1); 3 nM (lanes 2); 10 nM (lanes 3); and, 30 nM (lanes 4). LEF-1 DBD was added to a final concentration of 8 nM and, after an additional 45 min incubation, the samples were subjected to digestion with DNase I. The location of polyamide sites P3-1 to P3-4, LEF-1 sites L1 to L3, the LEF-1 HSS site and the start-site for transcription (+1) are shown alongside the autoradiogram.

EXAMPLE 6

Inhibition of RNA Polymerase II Transcription by Synthetic DNA-Binding Ligands The effects of polyamides 1 and 2 on HIV-1 transcription were tested in an in vitro transcription assay with a HeLa cell nuclear extract (FIG. 21A). The effects of the polyamides on basal transcription by RNA polymerase II was monitored with a nuclear extract prepared from HeLa cells (J. D. Dignam, P. L. Martin, B. S. Shastry, R. G. Roeder, Describe eukaryotic gene transcription with purified components *Meth. Enzymol.* 101, 582 (1983)). The human lymphloid cell line H9 (ATCC HTB 176) was grown in suspension culture in RPMI medium (Bio Whittaker) supplemented with 10% fetal calf serum (Tissue Culture Biological). Whole cell extracts of H9 cells in log phase growth were prepared by hypotonic lysis and contained 20 mg/ml protein, as determined by the Bradford reaction. Run-off RNA transcripts of ~300 bases (CMV MIEP linked to a guanine-less cassette, plasmid pEIB-GL and ~500 bases (pHIV LTR-CAT) where obtained with EcoRI-digested plasmid DNA (100 ng per 25 µL reaction).

Polyamide-DNA complexes were allowed to form at ambient temperature for 30 min prior to addition of the nuclear extract. Transcription complexes were allowed to form for 1 h at 30° C. prior to a transcription step for 1 h at 30° C. with 10 μCi of a-$^{32}$P-ATP, 10 μM unlabeled ATP, and 600 μM of the remaining unlabeled nucleoside triphosphates. RNA was purified by extraction with RNAzol (TelTest, Friendswood, Tex.) and analyzed by electrophoresis on a denaturing (8.3 M urea) 6% polyacrylamide gel. Autoradiograms were obtained by exposure of the dried gel to Kodak BioMax film with DuPont Cronex Lightning Plus intensifying screens for 1 to 18 h at −80° C. Relative levels of transcription were estimated by storage phosphorimage analysis.

Polyamide 1, which targets the HIV-1 TATA box, inhibits basal transcription from the HIV-1 promoter mediated by the general transcription factors SP1 and RNA polymerase II (FIG. 21A, lanes 2–4). HIV-1 transcription was inhibited 50% in the presence of between 50 and 100 nM polyamide 1 in several independent experiments. Polyamide 1 does not inhibit transcription from the CMV major intermediate early promoter (MIEP), which contains a mismatched TATA-flanking sequence (5'-GAGGTCTTATAAGCAGA-3') (SEQ ID NO:10). The mismatch polyamide 2 does not inhibit transcription from either promoter (FIG. 21A). Titrations were performed of polyamide 1 over a wide range of concentrations (1 to 200 nM) with both the HIV-1 and CMV templates in the same reaction. Under these conditions, 50% inhibition of HIV-1 transcription was observed at 30 nM polyamide 1, which corresponds to a 3–5 fold excess of polyamide over binding sites. No inhibition of CMV transcription was observed even at the highest concentrations of polyamide 1 (FIG. 21B). Polyamide 1, which has an additional binding site in the HIV-1 enhancer at nucleotide positions −153 to −147 (overlapping the Ets-1 site at −149 to −142), inhibits the DNA binding activity of the Ets-1 transcription factor.

The effects of polyamides 3 and 4 on HIV-1 transcription in an in vitro system consisting of a cell-free extract prepared from cultured human lymphoid H9 cells supplemented with HeLa cell extract were determined. The H9 extract contains high levels of LEF-1 protein but was found to support only low levels of transcription, suggesting a limited amount of other transcription components in this extract. The H9 cell extract was supplemented with small amounts of a HeLa cell-derived nuclear extract in order to obtain high levels of transcription (FIG. 21C, lane 1). The H9 HeLa cell extract stimulates HIV-1 transcription 2.5–3-fold over the level of transcription observed with the HeLa extract alone. Immunodepletion of LEF-1 protein from the H9 extract abolishes this activated transcription (FIG. 21C, compare lanes 1 and 6).

For immunodepletion and western blot analysis the H9 cell extract was depleted of LEF-1 protein with antibody to LEF-1 pre-bound to protein A sepharose beads. A mixture of 5 μl of antiserum and 50 μl of a 1:1 (v/v) slurry of protein A sepharose in transcription buffer supplenmented with 2.5 mg/ml bovine serum albumin (BSA) was incubated on a rotator at 4° C. for 1 hour. For mock immunodepletion, an equivalent volume of beads was treated identically without antibody. Unbound antibody and BSA were removed by brief centrifugation and the beads were washed three times with 50 μl of transcription buffer. For immunodepletion, the packed protein A beads were incubated with 10 μl of H9 cell extract, 45 μl of transcription buffer and 7.5 μl of 50 mM MgCl$_2$ on a rotator at 4° C. for 1 hour. The beads were then pelleted by brief centrifugation and the supernatant was tested for transcription activity. The efficiency of immunodepletion was determined by subjecting the depleted and mock-depleted extracts to SDS-PAGE and western blotting and was found to be greater than 95%. The blot was probed with antibody to LEF-1 (diluted 1:2500, kindly provided by K. Jones, Salk Institute, La Jolla, Calif.) and detected by enhanced chemiluminescence (Amersham ECL kit). Kodak Bio-Max film was used for detection.

Polyamide 3 inhibits HIV-1 transcription in this system (lanes 2–5) with a 50% reduction of transcription observed at 10–30 nM polyamide. Polyamide 3 fails to inhibit HIV-1 transcription in the LEF-1-depleted extract (lanes 7–10). The activity of the CMV MIEP was observed in both the mock-depleted and LEF-1 depleted H9 cell extract, with the result that LEF-1 depletion had no effect on CMV transcription. The effect of the mismatch polyamide 4 on HIV-1 transcription) (FIG. 21D, lanes 4 and 5) and polyamides 3 and 4 on CMV transcription (FIG. 21D, lanes 6–10) were examined as additional controls. No potential binding sites for either polyamide 3 or 4 are present in the CMV MIEP sequence. As expected, polyamide 3 fails to inhibit CMV transcription (FIG. 21D, lanes 7–8). The mismatch polyamide 4 fails to inhibit either HIV-1 or CMV transcription (lanes 4–5 and 9–10, respectively).

In FIG. 21A the inhibition of basal transcription with polyamide 1 is demonstrated. DNA templates containing the HIV-1 promoter (lanes 1–4, 9–12) and the CMV major immediate early promoter (lanes 5–8, 13–16) were incubated with the following concentrations of polyamide 1 (lanes 2–4, 6–8) or polyamide 2 (10–12, 14–16) prior to the addition of a HeLa cell nuclear extract (16): no polyamide, lanes 1, 5, 9, 13; 50 nM polyamide, lanes 2, 6, 10, 14; 100 nM, lanes 3, 7, 11, 15; 200 nM, lanes 4, 8, 12, 16. In FIG. 21B the relative levels of HIV-1 transcription/CMV transcription are plotted as a function of polyamide 1 concentration. Data were obtained from mixed template reactions containing both DNA templates as described in FIG. 21A. In FIG. 21C the inhibition of polyamide 3 on LEF-1-activated transcription is shown. Transcription reactions were performed with EcoRI-digested plasmid pHIV LTR-CAT and the H9 whole cell extract (2 μl) supplemented with 1 μl of the HeLa nuclear extract (lanes 1–5) or with 2 μl of the LEF-depleted H9 extract and the HeLa extract (lanes 6–10). Plasmid DNA was incubated with polyamide 3 for 15 min prior to addition of cell extracts and other reaction components. The final concentrations of polyamide in the reaction were: no polyamide (lanes 1 and 6), 10 nM (lanes 2 and 7), 30 nM (lanes 3 and 8), 100 nM (lanes 4 and 9) and 300 nM (lanes 5 and 10). In FIG. 21d, transcription with mismatch control polyamide 4 and a control CMV template. Plasmid DNA was incubated with polyamide 3 (10 nM, lanes 2 and 7; 100 nM, lanes 3 and 8) or polyamide 4 (10 nM, lanes 4 and 9; 100 nM, lanes 5 and 10) for 15 min at ambient temperature prior to addition of cell extracts and other reaction components.

Notably, polyamide 3 does not inhibit basal transcription with the HeLa nuclear extract although binding sites for this polyamide are present at the start-site for transcription and within the HIV-1 mRNA coding sequence present in plasmid pHIV-CAT. These observations suggest that RNA polymerase II can transcribe DNA with a polyamide bound in the minor groove and that polyamides are only inhibitory to transcription when these compounds interfere with the DNA binding activity of a required transcription factor.

EXAMPLE 7

Inhibition of RNA Pol II Transcription in Human Cells by Synthetic DNA-Binding Ligands The polyamides of the present invention have been demonstrated to inhibit HIV-1 transcription in virus-infected human cells. In general, M. E. Klotman, S. Kim, A. Buchbinder, A. DeRossi, D. Baltimore, F. Wong-Staal describe the kinetics of expression of multiply spliced RNA in early HIV-1 infection of lymphocytes and monocytes, *Proc. Natl. Acad. Sci. U.S.A.* 88, 5011–5015 (1991). Since there are multiple spliced and unspliced species of HIV-1 RNA with different turnover kinetics, viral transcription was not monitired by measuring levels of RNA. Instead, the effects of the polyamides on the levels and kinetics of HIV-1 replication in isolated human peripheral blood mononuclear cells (PBMC) was observed in culture. PBMC were infected with the T cell-tropic HIV-1 strain WEAU1.6, or the macrophage-tropic strain SF162. S. J. Clark et al describe high titers of cytopathic virus in plasma of patients with symptoms of primary human imunodeficiency virus type-1 infection. *N. Engl. J. Med.* 324, 954 (1991); P. Borrow, et al., describe antiviral pressure exerted by HIV-1 specific cytotoxic T-lymphocytes (CTLS) during primary infection demonstrated by rapid selection of CTL escape virus *Nature Med* 3, 205 (1997); C. Cheng-Mayer, D. Seto, M. Tateno, J. A. Levy describe biologic features of HIV-1 that correlate with virulence in the host. *Science* 240, 80 (1988); C. Cheng-Mayer, C. Weiss, D. Seto, J. A. Levy, Describe isolates of HIV-1 from the brain may not constitute a special group of the AIDS virus. *Proc. Natl. Acad. Sci. USA* 86, 8575 (1989). Polyamides were added to the culture medium and the levels of HIV-1 p24 viral capsid protein in the culture media were determined on subsequent days using a standard ELISA assay.

Human PBMC were separated from whole blood collected from normal adult volunteers by density gradient centrifugation as described. D. E. Mosier, et al. describe HIV-1 infection of human-PBL-SCID mice *Science* 251, 791 (1991); D. Mosier, R. Gulizia, P. MacIsaac, B. Torbett, J. Levy, describe rapid loss of CD4+ T-cells in human-PBL-SCID mice by noncytopathic HIV isolates *Science*, 260, 689 (1993). Donors were provided by the General Clinical Research Center of The Scripps Research Institute, which is supported by NIH grant MO1 RR00833. Human PBMC were activated with 2 $\mu$g/mL PHA and 20 units/mL of IL-2 for 2–3 days prior to HIV-1 infection. Each culture of $5\times10^5$ PBMC was infected with $10^3$ tissue culture infectious doses of HIV-1 for 24 hours. Free virus was removed by washing the cells in medium, and polyamides added to the culture. In the experiment shown in FIG. 22C, polyamides were added 24 hours prior to virus exposure, and were continuously present thereafter. Virus replication in culture was measured by HIV-1 p24 viral capsid antigen ELISA (DuPont Medical Products, Boston, Mass.).

Assays of HIV-1 replication representative of five replicate experiments with five human PBL donors are shown in FIGS. 22 and 23, illustrating results from two experiments employing different donors. Each experiment is controlled by using polyamides which differ by single atomic substitution from the inhibitory polyamides. In control PBMC cultures with no added polyamide, viral replication resulted in increasing p24 levels between day 4 and day 10 of culture (FIG. 23). Addition of mismatch control polyamides 2 and 4 had no effect on the level of virus in the medium, either alone (FIGS. 22, A, B, & D) or in combination (FIG. 22C).

Figure 22A:
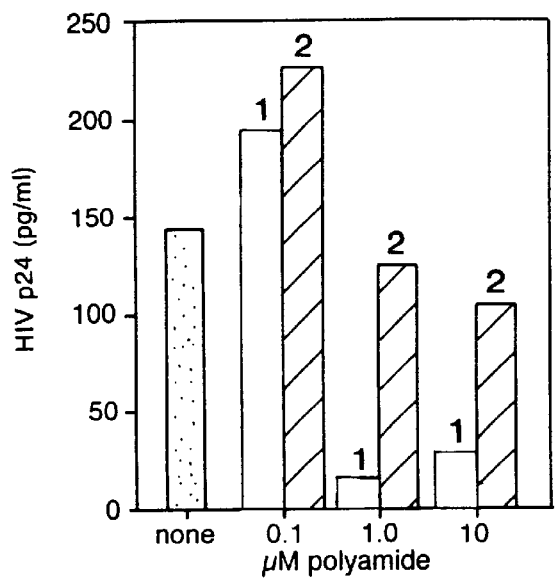
FIG. 22 its a graphical representation of the results of a experimental treatment of human white blood cells infected with HIV.
Figure 22B:
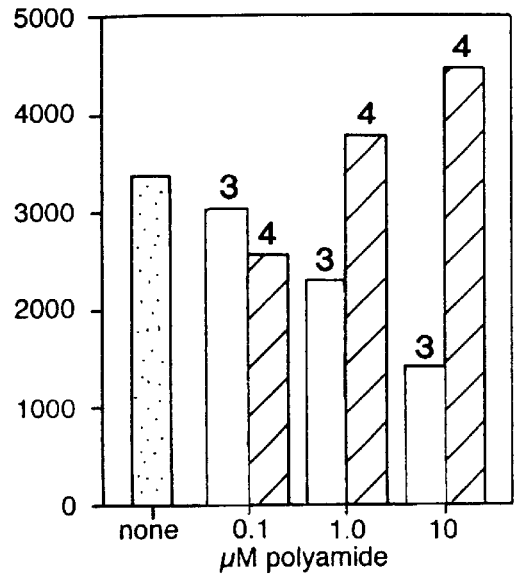
Figure 22C:
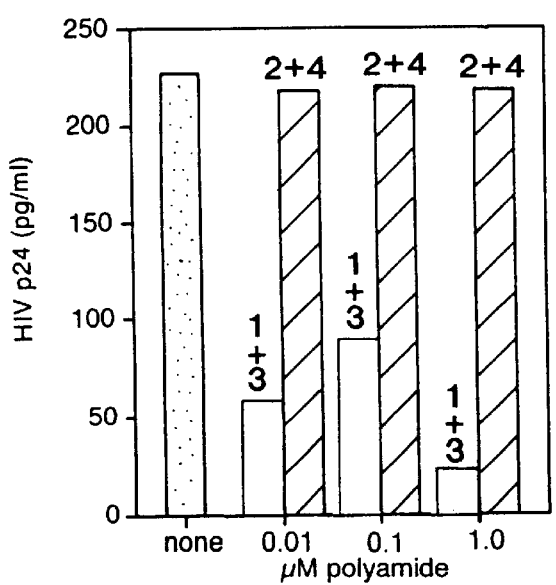

In contrast, both polyamides 1 and 3 added to the culture medium reduced p24 levels in a dose-dependent manner (FIGS. 22A & B). Polyamide 1 at 1 $\mu$M concentration caused an 80% reduction in virus (FIG. 22A), while polyamide 3 at 10 $\mu$M concentration caused a 60% reduction (FIG. 22B). These inhibitory effects were clear at 6 or 8 days of culture, but became less pronounced at later times. The two polyamide ligands, when used individually, delay the appearance of virus rather than absolutely inhibit virus production.

Figure 22D:
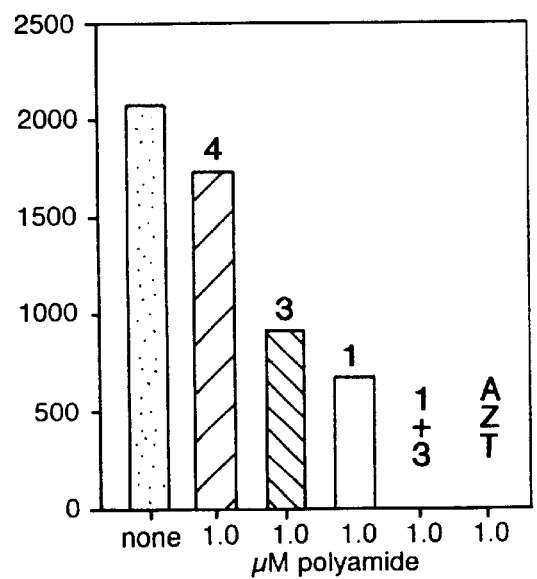
Figure 23B:
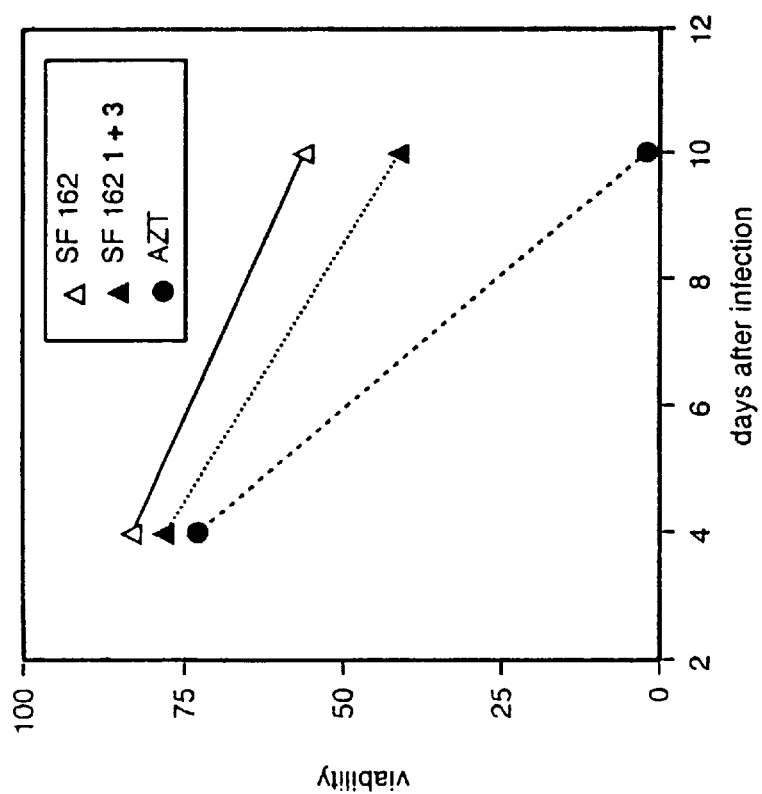
FIG. 23 is a graphical representation of the results of a experimental treatment of human white blood cells infected with HIV.
Figure 23A:
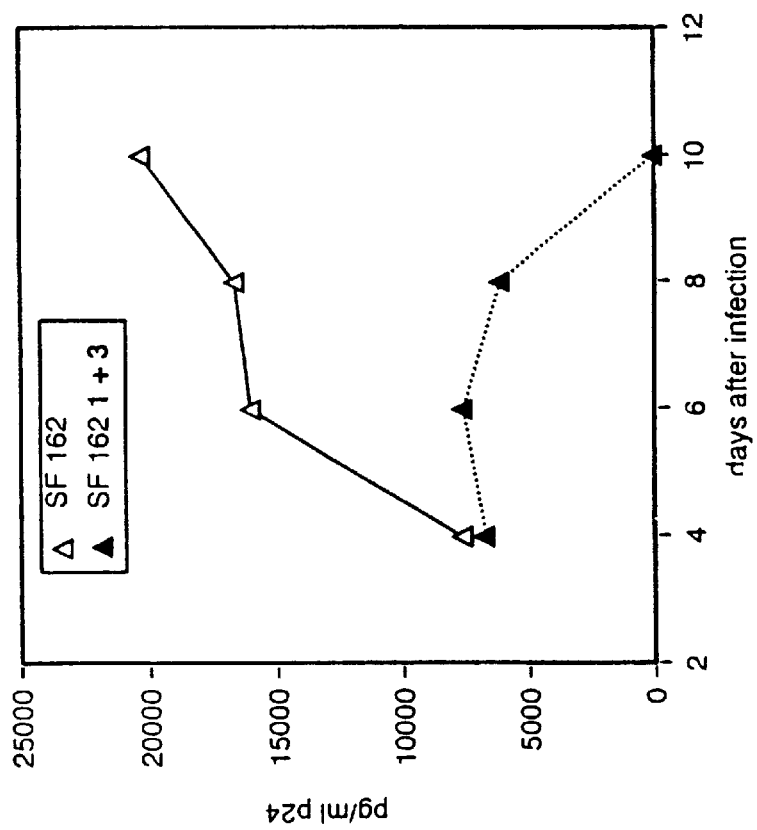
Figure 23D:
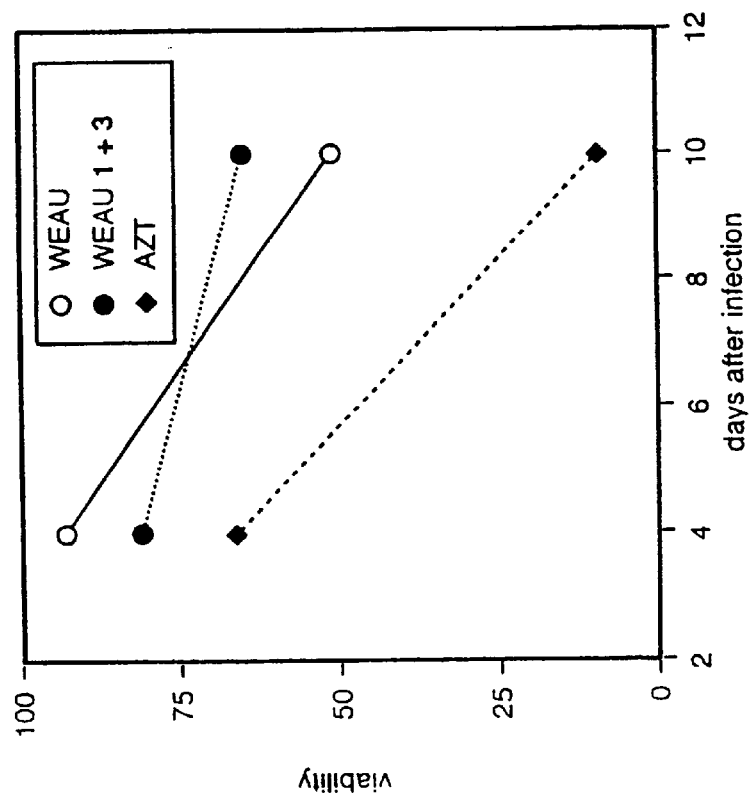
Figure 23C:
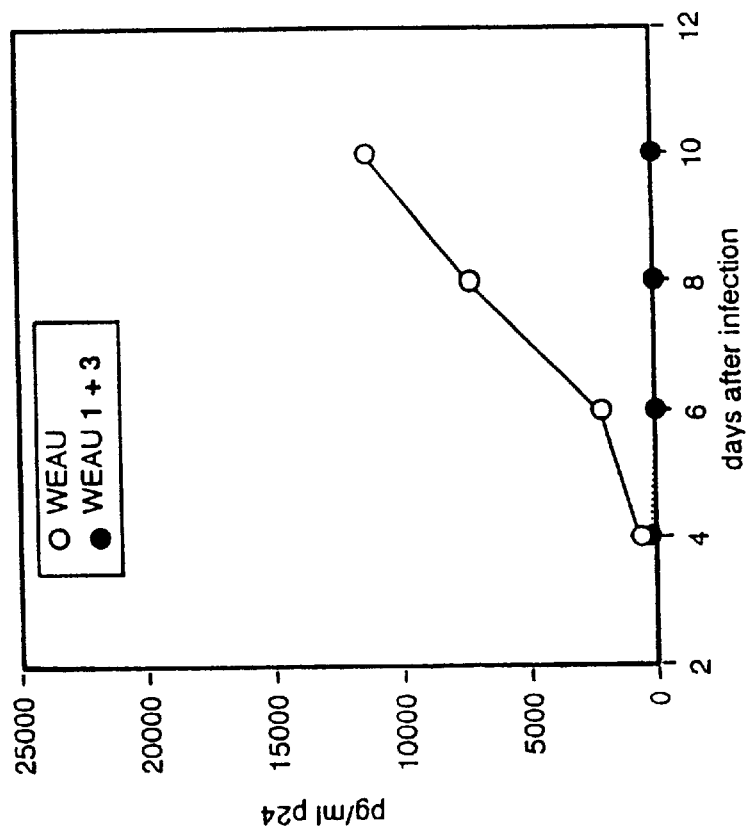

The combination of polyamides 1 and 3 at 1 $\mu$M each can act in synergy to reduce viral p24 levels to below the threshold of detection (<10 pg/ml; greater than 99.9% inhibition of viral replication) (FIGS. 22D, 23A & C), and were as effective as 1 $\mu$M azidothymidine (AZT) in blocking HIV-1 replication (FIG. 22D). The macrophage-tropic SF162 isolate, which replicates in both macrophages and CD4$^+$ T lymphocytes, was more difficult to inhibit with single polyamides, but the combination of 1 $\mu$M polyamides 1 and 3 was able to reduce and eventually block its replication (FIG. 23A). These results demonstrate that cell-permeable synthetic DNA ligands can effectively inhibit HIV-1 replication in isolated human lymphocytes in culture and suggest that inhibition of virus replication is due to inhibition of transcription factor-DNA interactions and gene transcription of viral and possibly cellular genes by RNA polymerase II. The observed polyamide inhibition of virus replication is likely due to interference with the DNA binding activities of TBP and Ets-1 by polyamide 1 and the binding activity of LEF-1 by polyamide 3. The inhibitory effects of polyamides singly or in combination was not due to obvious toxicity. No significant decrease in cell viability was apparent in PBMC cultures treated with polyamides 1 and 3 for 10 days, in contrast to 90% mortality observed for PBMC cells treated with 1 $\mu$M AZT for the same period (FIGS. 23B & D). Cell viability was not impacted by polyamide treatment, but was reduced by AZT treatment.

Figures 24A, 24B:
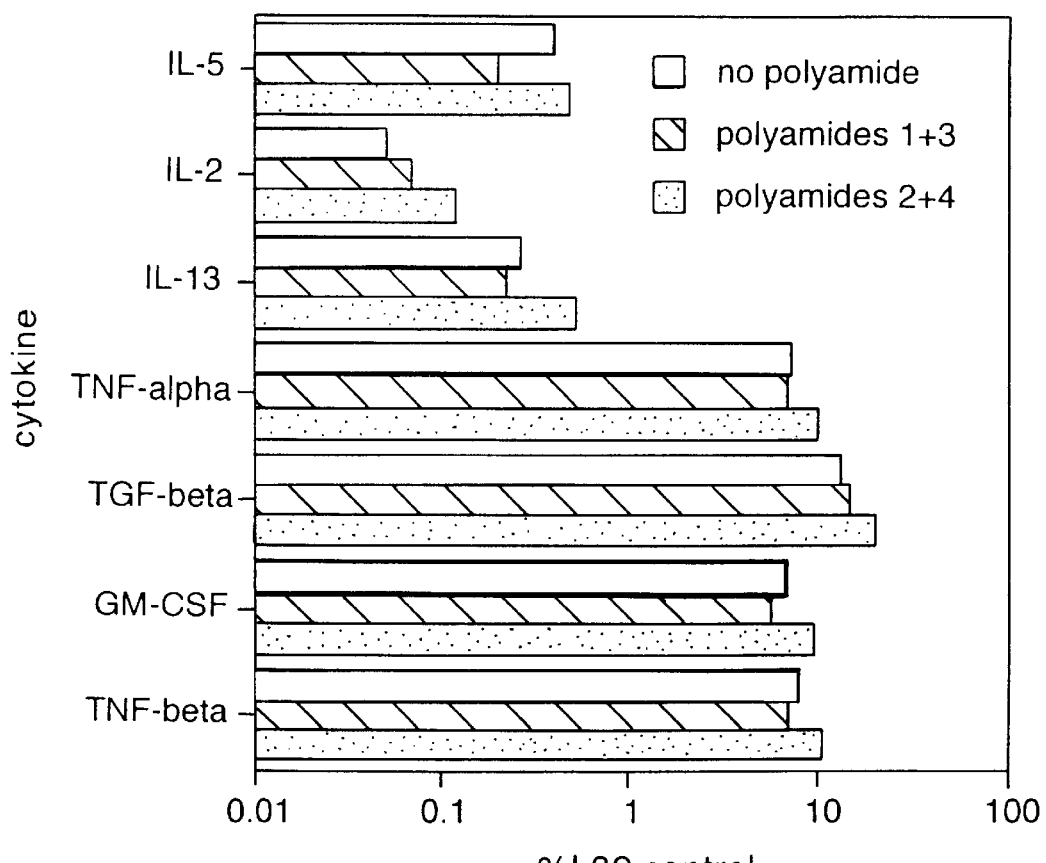
FIG. 24 is a graphical representation of the results of a experiment demonstrating the specificity of polyamides.

The combination of polyamides 1+3 inhibited HIV-1 replication, but the closely related polyamides 2+4 did not. The simplest explanation for this finding is that polyamides 1+3 inhibited HIV-1 RNA transcription in cells as well as in the in vitro assays (FIG. 22), but it is possible that inhibition of cellular genes involved in T cell activation could result in an indirect effect on HIV-1 replication. To further assess this possibility, a sensitive RNAase protection assay was performed for transcripts of a number of cytokine genes, including IL-2, IL-5, and IL-13 which differ by only single base mismatches from the target sequences flanking the TATA box in the HIV-1 LTR. Four other cytokine genes that lack binding sites for either polyamide 1 or 3 in their promoters were also examined (FIG. 24A). The results (FIG. 24B) show that exposure of activated human PBMC to a combination of either polyamides 1+3 or 2+4 (1 $\mu$M each) for 6 days failed to inhibit cytokine RNA expression. This lack of inhibition of cytokine gene transcription suggests that the polyamides reduce virus replication in cells by a direct effect on HIV-1 RNA transcription.

Our present studies have utilized polyamides designed to target DNA sequences 6–7 bp in length and have shown that these compounds are effective inhibitors of gene transcription in cell-free systems and, vida infra, in human cells. Because sequences of these lengths would be highly redundant in the human genome, it had seemed likely that these ligands would have deleterious effects on cell metabolism due to interference with the activity of cellular genes. However, the results described here indicate that a battery of polyamides which recognize 6–7 bp sequences will be sufficient for gene-specific regulation in vivo. It is interesting to compare these small molecule transcription factors to eukaryotic transcriptional regulatory proteins which also recognize multiple sequences of similar length in tandem in order to increase functional specificity. Tile observations that polyamides do not interfere with pol II elongation, and that polyamides can bind simultaneously with certain major groove binding proteins should further enhance gene-specificity. M. G. Oakley, M. Mrksich, P. B. Dervan describe simultaneous binding of polyamide in the minor groove with a protein in the major groove. *Biochemistry* 31, 10969 (1992).

As shown in FIG. 16, polyamides are not limited to 6–7 base-pair recognition, but can bind as cooperative dimers to sequences up to sixteen base pairs in length. Trauger, J. W., Baird, E. E. Mrksich, M., Dervan, P. B. describes the recognition of 9–13 base pairs of DNA by a β-alanine linked extended polyamide dimer.

The specific inhibition of genes transcribed by RNA polymerase II represents an important first step toward asking whether cell-permeable small molecule transcription antagonists might regulate gene expression in complex organisms. TBP and sequences adjacent to the TATA element for inhibition of basal transcription by RNA polymerase II were chosen. Since most tissue-specific cellular genes and viral genes contain TATA elements, this approach is generally applicable for the inhibition of most target genes.

The inhibition of HIV-1 replication in peripheral blood mononuclear cells by polyamides is shown in FIG. 22. Panels A–D depict three separate experiments in which polyamides alone (A, B) or in combination (C, D) were added to cultures of human peripheral blood mononuclear cells (PBMC) stimulated 3 days earlier with phytohemagglutinin and interleukin-2. PBMC cultures were infected with the primary HIV-1 isolate WEAU 1.6 (kindly provided by G. Shaw), and virus replication measured by release of p24 capsid antigen into the medium that was detected by antibody-capture ELISA (Dupont). Each experiment involved a separate PBMC donor. Values shown are for day 6 or day 8 after virus infection. When two polyamides were combined, the concentration shown is for each component of the mixture. In panel D, the combination of 1 μM polyamide 1+1 μM polyamide 3 cooperatively blocked virus infection and p24 release (below 10 pg/ml, the detection limit of the assay), as did the addition of 1 μM azidothymidine (AZT). Assays of p24 concentration were performed in duplicate and showed less than 5% variation from the mean value reported.

FIG. 23 shows the kinetics of the inhibition of HIV-1 replication and effects on cell viability by a combination of polyamides added to PBMC cultures. PBMC were isolated as in FIG. 22 and infected either with the macrophage-tropic HIV-1 isolate SF162 (panels A and B) or the T-cell tropic isolate WEAU 1.6 (panels C and D). Polyamides 1 and 3 were added in combination at 1 μM each. Although each polyamide alone was not very effective in blocking replication of HIV-1 SF162 (data not shown), the combination of both polyamides was able to stabilize and later reduce virus p24 production to undetectable levels (panel A, filled triangles) while untreated cultures (open triangles) continued viral replication. Cell viability was determined at days 4 and 10 of culture by trypan blue exclusion.

The combination of polyamides 1 and 3 caused a small decrease in viability compared to cultures that were untreated (panel B, filled versus open triangles), but parallel cultures treated with 1 μM azidethymidine (AZT) showed a much more severe decline in cell viability. AZT completely inhibited virus replication of both HIV-1 SF162 and WEAU 1.6 at this concentration (data not shown). In contrast to these results, each polyamide alone partially inhibited replication of HIV-1 WEAU 1.6 (see FIGS. 23A & B), and the combination of polyamides 1 and 3 blocked replication at all times examined (panel C, filled circles) compared to untreated cultures (open circles). Cell viability was higher in cultures treated with polyamides 1 and 3 thin in untreated cultures (panel D, filled circles versus open circles), probably because the cytopathic effect of HIV-1 infection was completely reversed. AZT again showed substantial toxicity for cells. Assays of p24 concentration were performed in duplicate and showed less than 5% variation from the mean value reported. Similar results were obtained in two additional experiments.

A lack of inhibition of cytokine gene expression with polyamides targeted to the HIV-1 promoter and enhancer sequence can be seen in FIG. 24. In FIG. 24A the sequences of the TATA-box region (taken from GenBank listings) of each of the cytokine/growth factor genes examined are shown with the TATA box in bold and the binding site for polyamide 1 underlined. Single base mismatches are indicated in lower case. In FIG. 24B, human peripheral blood mononuclear cells were cultured under the same conditions used for HIV-1 infection. Cultures were either left untreated, or 10 μM of polyamides 1+3 or polyamides 2+4 added. After six days, cells were harvested, total RNA extracted, and a ribonuclease protection assay performed with riboprobes specific for the indicated cytokines as well as for CD4, CDS and ribosomal protein L32. M. V. Hobbs, et al., describe patterns of cytokine gene-expression by CD4+ T-cells from young and old mice *J. Immunol* 150, 3602 (1993). After digestion with RNAse T1, protected fragments were separated by polyacrylamide gel electrophoresis, and the amount of labeled probe quantitated by PhosphorImager analysis. Data are expressed as the intensity of each cytokine RNA relative to the intensity of the ribosomal L32 RNA band to standardize for RNA loading. There was no difference in the intensity of CD4 and CD8 RNA bands between groups, indicating equivalent recovery of CD4 and CD8 T cells in all cultures. Similar results were seen when the cultured cells were analyzed after 10 days, although the levels of RNA for most cytokines had declined in both polyamide treated and untreated cells.

EXAMPLE 8

Differential Inhibition of Ets-1 Binding With Two Polyamides

Figure 25:
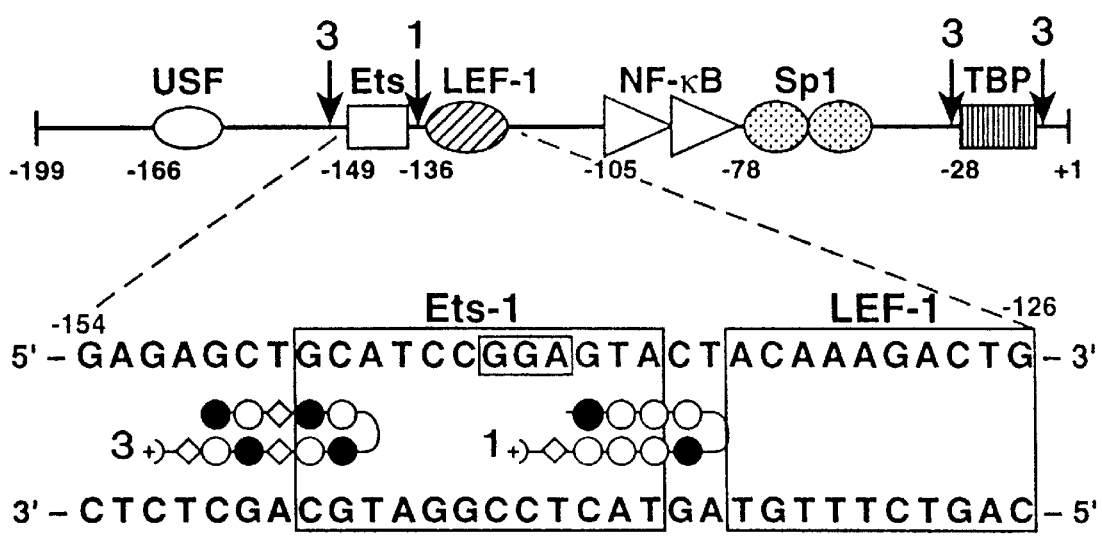
FIG. 25 is a schematic representation of polyamide binding to the DNA sequence adjacent to the Ets-1 site.

Ets-1 is another cellular transcription factor required for high levels of HIV-1 RNA synthesis (FIG. 25). FIG. 25 shows the schematic structures of polyamides targeted to the Ets-1/LEF-1 region of tile HIV-1 enhancer and the sequence of the binding sites for these polyamides. Polyamides 1 and 2 have been described above in the context of the LEF-1 inhibition experiments above . Polyamide 3 (ImPy-β-ImPy-γ-ImPy-β-ImPy-β-Dp) binds the sequence 5'-TGCTGCA-3' with a $K_d$ of 0.05 nM, while the mismatch polyamide 4 (ImIm-β-ImIm-γ-PyPy-β-PyPy-β-Dp) exhibits 100 fold lower affinity for binding that site. The binding sites for polyamides 1 and 3 are located immediately downstream (polyamide 1) and upstream (polyamide 3) of the Ets-1 DNA recognition sequence in the HIV-1 enhancer region (FIG. 25B). Polyamide 3 also recognizes sequences immediately flanking the TATA box of the HIV-1 promoter, and was shown to inhibit DNA-binding of TBP and prevent basal transcription from this promoter.

Schematic representation of the HIV-1 enhancer/promoter region with the DNA-binding sites for the transcription factors USF, Ets-1, LEF-1, NF-kappaB, Sp1 and the TATA-binding protein TBP. The positions of the polyamide binding sites are indicated by vertical arrows. The DNA-binding sites for polyamides 1 and 3 flanking the Ets-1 recognition site are shown in detail below. The Ets-1 binding site is boxed, the GGA core recognition sequence, that is conserved in most Ets-protein binding sites, is indicated by a small rectangle. The LEF-1 binding site is underlined.

Figure 26:
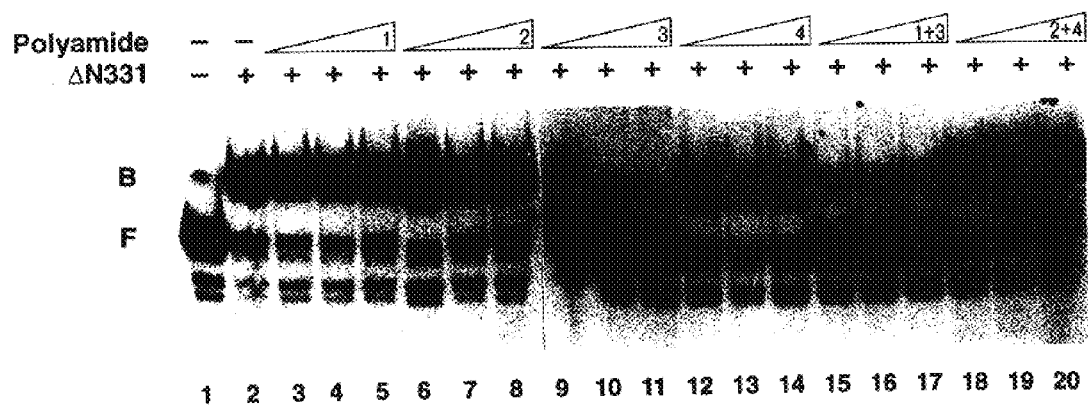
FIG. 26 is a representation of the results of a footprint experiment comparing the binding of polyamides and ΔN331 to the HIV-1 promoter region.

Since the Ets-1 binding site is flanked by and partially overlaps with both polyamide 1 and polyamide 3 binding sites, whether Ets-1 binding could be inhibited by either one, or both of these two polyamides was tested by gel mobility shift experiments. When polyamides were preincubated with a radiolabeled double-stranded HIV oligonucleotide before adding Ets-1 ΔN331, polyamide 1 had no effect on Ets-1 DNA-binding, even at a concentration as high as 400 nM (FIG. 26 lanes 3–5). Polyamide 3, however, prevented the Ets-1/DNA complex formation (FIG. 26, lanes 9–11). When both polyamides were combined, the degree of inhibition was very similar to the one observed with polyamide 3 alone (FIG. 26, lanes 15–17). The two mismatch polyamides 2 and 4 did not prevent complex formation, either alone or combined (FIG. 26, lanes 6–8, 12–14 and 18–20). A titration experiment revealed that polyamide 3 inhibited Ets-1 ΔN331/DNA complex formation by 50% at a concentration of approximately 6 nM, nearly complete inhibition was achieved between 50 and 200 nM polyamide. Mismatch polyamide 4 had virtually no effect in the same concentration range.

Figure 27A:
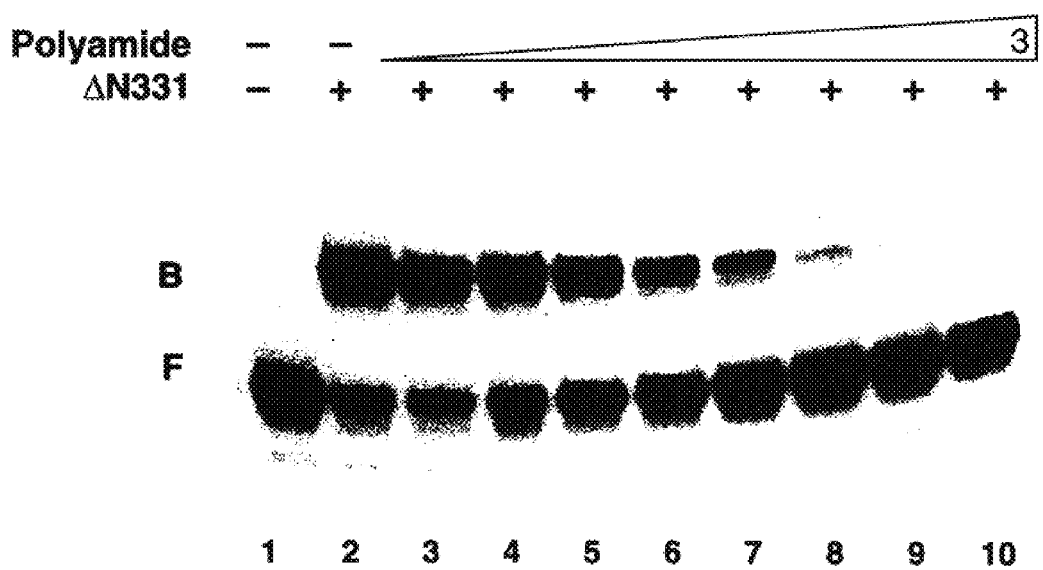
FIG. 27 is a representation of the results of experiments showing the specific Ets-1 binding inhibition produced by polyamides.
Figure 27B:
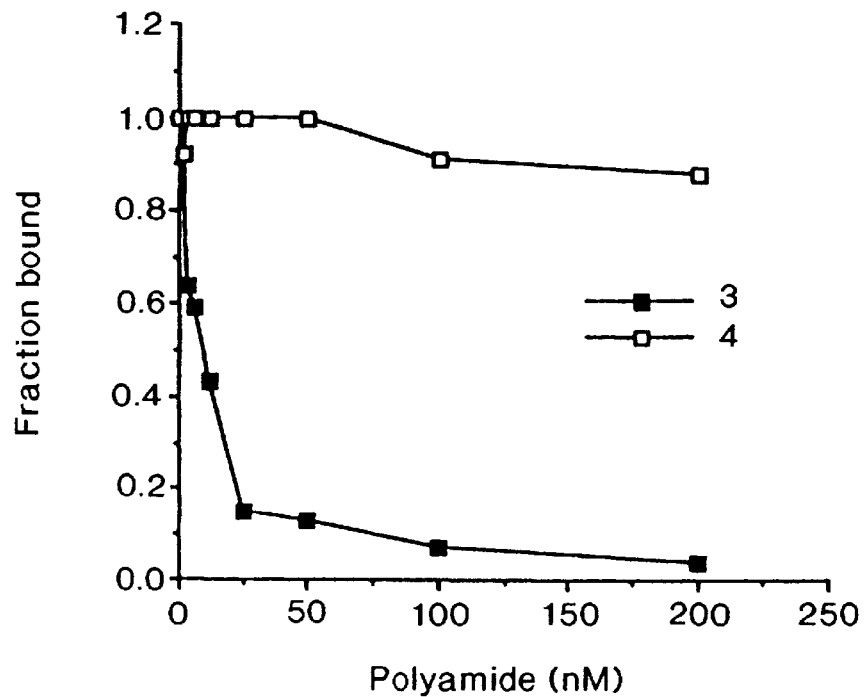
Figure 27C:
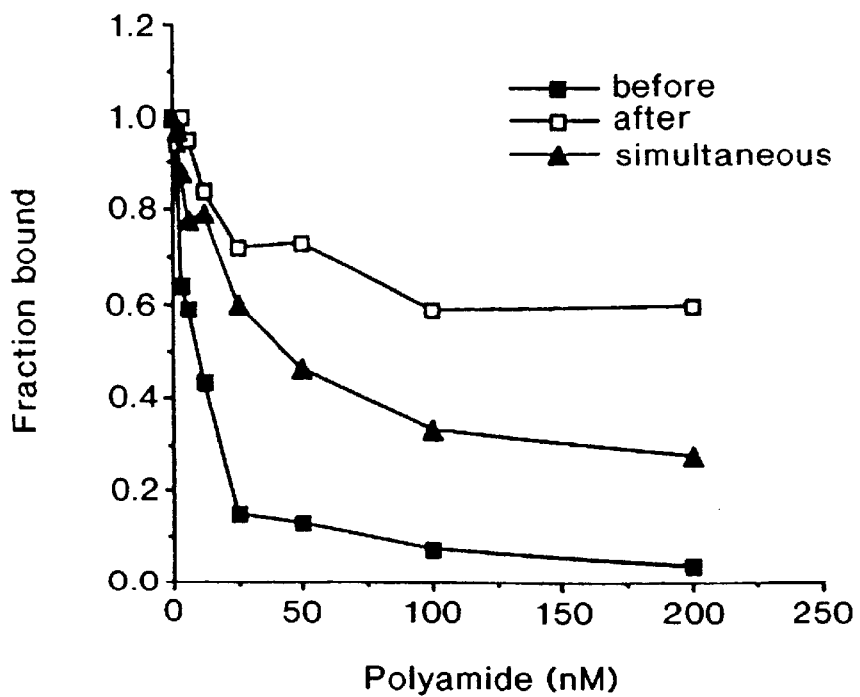

A double-stranded, labeled oligonucleotide corresponding to the Ets-1 binding site with flanking regions within the HIV-1 enhancer/promoter was used as a probe in gel mobility shift assays. Polyamides were preincubated with the DNA before addition of Ets-1, where indicated. The concentrations of polyamides were 100 nM (lanes 3, 6, 9, 12, 15 and 18), 200 nM (lanes 4, 7, 10, 13, 16 and 19), and 400 nM (lanes 5, 8, 11, 14, 17 and 20). ΔN331 protein was added at a concentration of 12 nM. Positions of the free probe (F) and bound probe (B) are indicated. FIG. 27A shows a representation of an autoradiogram of a representative gel mobility shift assay showing the inhibitory effect of polyamide 3 on ΔN331 binding. The concentration of ΔN331 was constant (12 nM in lanes 2–10), the probe concentration was 50 pM. The polyamide was preincubated for 20 min at room temperature before addition of the protein, followed by an additional 20–30 min incubation on ice. The polyamide concentrations were 1.56, 3.125, 6.25, 12.5, 25, 50, 100, 200 nM in lanes 3 to 10, respectively. FIG. 27B is a graphical representation of the decrease of the fraction of bound probe as a function of polyamide concentration. Closed squares represent the data points obtained for polyamide 3, open squares represent mismatch polyamide 4. FIG. 27C is a graphical representation of the effect of polyamide 3 on Ets-1 binding when added at different time points during the binding reaction. Polyamide 3 was added to the probe either prior to addition of Ets-1 (closed squares), or after addition of Ets-1 (open squares), or simultaneously with Ets-1 (closed triangles).

Figure 28:
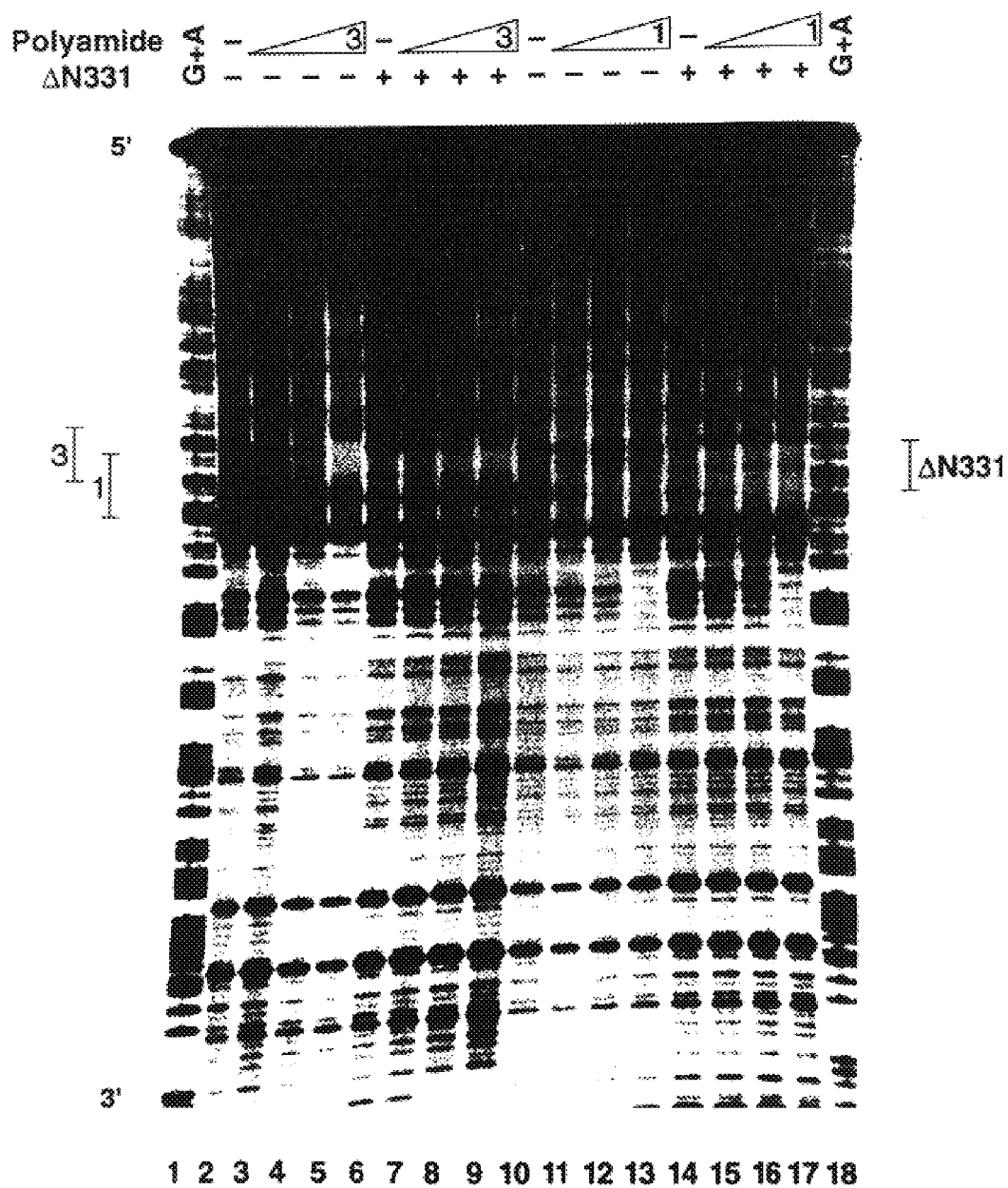
FIG. 28 is a representation of the results of a footprint experiment comparing the binding of polyamides and ΔN331 to the HIV-1 promoter region.

FIG. 28 is a representation of the results of DNase I footprint titration experiment with polyamides 1 and 3 in the absence (−) or presence (+) of 9.6 nM ΔN331 protein. Polyamides were incubated with the radiolabeled probe prior to addition of Ets-1. The polyamide concentrations were 0 nM (lanes 2, 6, 10, 14), 4 nM (lanes 3, 7, 11, 15), 20 nM (lanes 4. 8, 12, 16) and 100 nM (lanes 5, 9, 13, 17). Lanes 1 and 18 show a G+A sequencing ladder. The regions protected by polyamides and by Ets-1 are indicated alongside the sequencing ladder. Note the two DNase I hypersensitive sites characteristic of the Ets-1 footprint.

Polyamide 3 Prevents Ets-1 DNA-binding While
Polyamide 1 Coexists With Ets-1 on Overlapping
DNA Binding Sites A labele.I DNA fragment derived from the HIV-1 enhancer was incubated with each polyamide either alone, or followed by addition of Ets-1 and a further 30 minute incubation. As expected, both polyamides bound their target site with similar affinities, polyamide 1 even bound with a slightly higher affinity than polyamide 3, complete protection was observed with 20 nM polyamide 1, and (with 100 nM polyamide 3 (FIG. 28, lanes 3–5 and 11–13). The Ets-1 footprint is characterized by two DNase I hypersensitive bands appearing in the center and at the 5' boundary of the footprint. These hypersensitive sites disappear with the addition of 20 to 100 nM polyamide 3 (FIG. 28, lanes 7–9), but remain unchanged with the addition of polyamide 1 (FIG. 28, lanes 15–17). The simultaneous presence of polyamide 1 and Ets-1 results in a broadening of the footprint, corresponding to a combined footprint created by Ets-1 and polyamide 1 (FIG. 28, lanes 14–17), while the Ets-1 footprint is replaced by the polyamide 3 footprint (lanes 7–9). Based on the structure of the Ets family protein PU.1 in complex with its DNA recognition element, it has been proposed that DNA recognition is mediated by both major groove and minor groove contacts. In the case of Ets-1, minor groove contacts would be expected to occur at the 5' end of the recognition element. This structural prediction is in complete agreement with our polyamide inhibition experiments. A polyamide located at the 5' end of the Ets-1 site is inhibitory to DNA binding whereas a polyamide located at the 3' end of the Ets-1 site is not inhibitory to DNA binding.

EXAMPLE 9

Inhibition of TBP Binding and Basal Transcription with Polyamides Designed to Bind Sequences Adjacent to the TATA Element The previous Examples demonstrate that polyamides which bind sequences adjacent to the well-conserved TATA sequence upstream from the transcription start-site of messenger RNA-coding genes inhibit TBP binding and basal transcription by RNA polymerase II. This method is a useful general approach for modulation of gene expression. For example, specific polyamides have been designed and synthesized that bind to double stranded DNA adjacent to the TATA element of the human cytomegalovirus major immediate early promoter (CMV MIEP). Polyamide CMV-1, ImImPyPy-γ-ImPyPyPy-β-Dp, binds the identified target sequence 5'-AGGTCT-3', where the last T of this sequence is the 5' T of the TATA element. Polyamide CMV-1 binds the CMV MIEP with an apparent dissociation constant of 1 nM and is an effective inhibitor of TBP binding and basal transcription. Appropriate mismatch polyamides do not inhibit either TBP binding or transcription.

In another example, a polyamide was designed to bind immediately downstream of the TATA element found in the human Her-2/neu breast cancer oncogene promoter. This polyamide, Her2-1, of composition ImPy-β-PyIm-γ-PyPy-β-PyPy-β-Dp, binds the sequence 5'AGAATGA-3' (which the 5' A of this sequence is the 3' A of the TATA element) with an apparent dissociation constant of 20 pM and is an effective inhibitor of TBP binding and transcription. Her-2/neu is recognized to be over-expressed in several cancers, including human gynecologic adenocarcinomas, including those of the ovary, endometrium, breast, fallopian tube and cervix (Cirisano, F. D., & Karlan, B. Y., *J. Soc. Gynecol. Investig.* 3 99–105 (1996)).

These additional data confirm the generality of this approach and demonstrate that polyamides located either upstream or downstream of the TATA element are effective transcription inhibitors. Table 3, below, lists the gene promoters, TATA sequences and composition of the polyamides which have been shown to be inhibitors of TBP binding and transcription.

TABLE 3

Polyamide Inhibition of TBP Binding and Basal Transcription by Targeting Sequences Adjacent to the TATA Element

| GENE | TATA SEQUENCE | POLYAMIDE |
|---|---|---|
| Artificial TATA | 5'-TATA<u>AGTACTT</u>-3' (SEQ ID NO:11) | ImPyPyPy-γ-ImPyPyPy-β-Dp |
| HIV-1 Promoter | 5'-<u>TGCTGC</u>ATATAA-3' (SEQ ID NO:12) 5'-TATA<u>AGCAGCT</u>-3' (SEQ ID NO:13) | ImPy-β-PyIm-γ-PyPy-β-PyPy-β-Dp |
| CMV MIEP | 5'-AGGTCTATAA-3' (SEQ ID NO:14) | ImPy-β-Im-γ-PyPy-β-PyPy-β-Dp |
| Her-2/neu oncogene (Breast Cancer) | 5'-TATA<u>AGAATGA</u>-3' (SEQ ID NO:15) | ImPy-β-PyIm-γ-PyPy-β-PyPy-β-Dp |

EXAMPLE 10

Anti-repression of Polymerase II Transcription by a Designed Ligand

Pyrrole-imidazole polyamides can exert a positive effect on transcription by interfering with the activity of a specific repressor protein. The human cytomegalovirus (HCMV) IE86 repressor protein is well suited for this study, because transcriptional repression is dependent on IE86 binding to its DNA target site. IE86 negatively regulates the major immediate early promoter (MIEP) of HCMV by binding to a sequence element (the cis repression signal, crs) located between the TATA box and the start of transcription. It was shown that IE86 exerts its negative effect on transcription by binding to the crs element, thereby blocking recruitment of RNA polymerase II. The polyamides that specifically recognize the crs, prevent IE86 from binding and relieve transcriptional repression, while a mismatch polyamide or a polyamide which binds to a nearby site, have no effect. Furthermore, occupancy of the crs element by a small polyamide is not sufficient to repress transcription, supporting the model that IE86-mediated repression results from steric interference with the recruitment of RNA polymerase II to the preinitiation complex.

FIG. 29 is a schematic representation of the sequence of the HCMV MIEP region from position −34 to +7. The TATA box and the repressor binding site (located at −14 to +1 relative to the start site of transcription) are boxed. The polyamides are schematically represented at their respective DNA binding sites. The shaded and open circles represent imidazole and pyrrole rings, respectively, the hairpin junction is formed by γ-aminobutyric acid, and the diamond represents β-alanine. Polyamides 2 and 3 contain an additional amino group at the hairpin junction. The mismatch in polyamide 4 is boxed. Structures of five polyamides are shown schematically: ImPyImPy-γ-PyPyPyPy-β-Dp (1), ImPyImPy-2,4D-PyPyPyPy-β-Dp (2), Im-β-ImPy-2,4D-PyPyPyPy-β-Dp (3), ImPyPyPy-γ-PyPyPyPy-β-Dp (4) and ImImPyPy-γ-ImPyPyPy-β-Dp (5), which binds the sequence 5'-AGGTCT-3' adjacent to the TATA box. Im=imidazole, Py=pyrrole, γ=γ-aminobutyric acid, β=β-alanine, 2,4D=2,4 diaminobutyric acid, and Dp=dimethylaminopropylamide.

The eight ring polyamide 1, ImPyImPy-γ-PyPyPyPy-β-Dp, binds the six base pair sequence 5'-AGTGAA-3' within the IE86 binding site with an apparent dissociation constant of 1.4 nM. The predicted structure of this complex is shown in FIG. 29 (polyamide 1). Two additional polyamides were synthesized that bind the same site, but with higher affinities: polyamide ImPyImPy-D-PyPyPyPy-β-Dp (polyamide 2, where 2,4D represents 2,4 diaminobutyric acid) and Im-β-ImPy-2,4D-PyPyPyPy-β-Dp (polyamide 3) bind the sequence 5'-AGTGAA-3' with $K_d$s of 1 nM and 0.25 nM, respectively. A single atom substitution in this molecule, changing an imidazole to a pyrrole (nitrogen to C—H; polyamide 4, shown in FIG. 29), reduces the affinity of this compound by ~30 to 100-fold for its target site. A control polyamide, ImImPyPy-γ-ImPyPyPy-β-Dp (polyamide 5) binds the sequence 5'-AGGTCT-3' adjacent to the TATA box of the MIEP with a $K_d$ of 1 nM.

Figure 30:
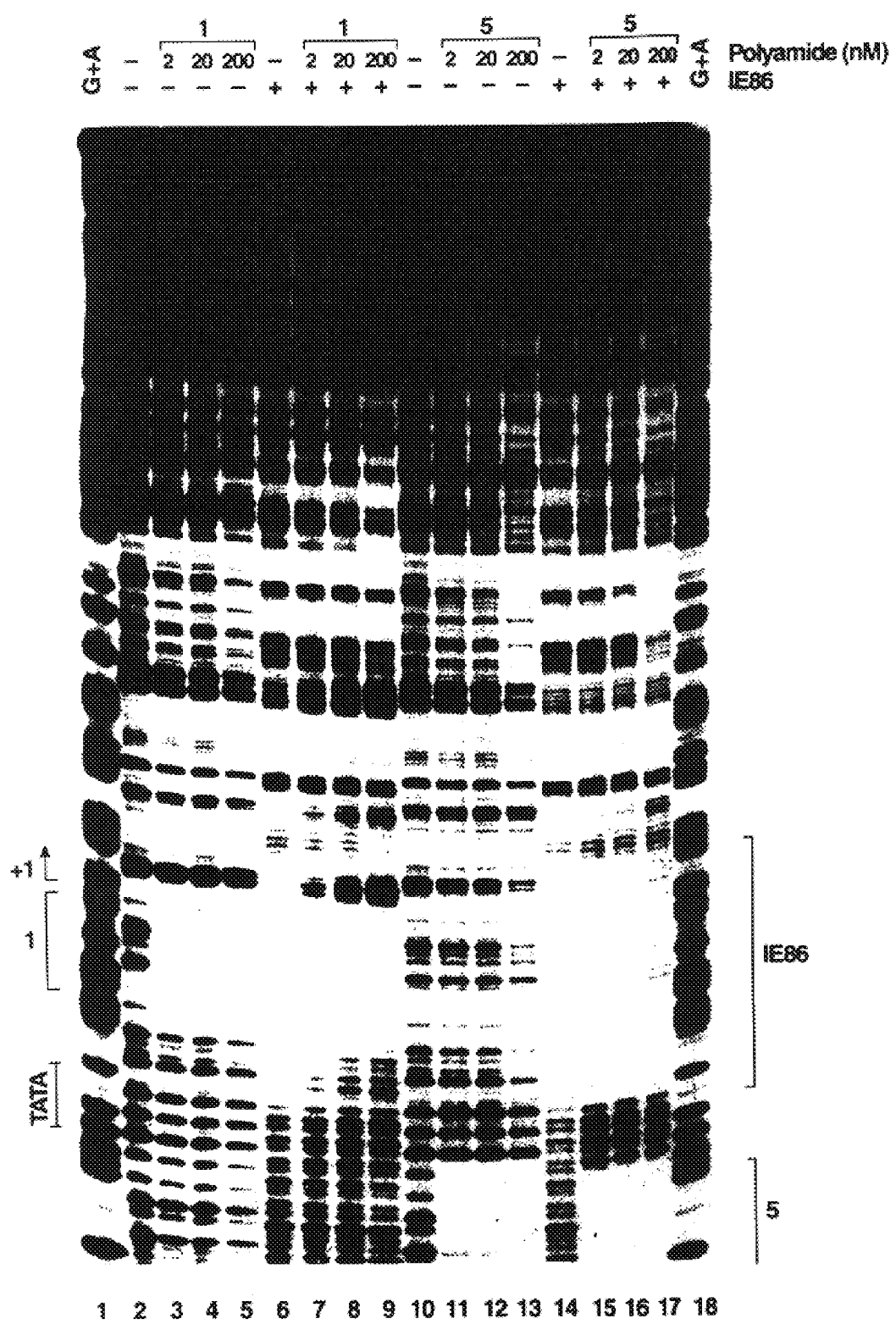
FIG. 30 is a representation of the results of a footprint experiment comparing the binding of polyamides 1 and 5 and IE86 to the repressor region of the CMV genome.

These compounds together with purified recombinant IE86 protein were used in DNase I footprint experiments with a singly end-labeled restriction fragment derived from the CMV major immediate early promoter. As predicted, polyamide 1 protects the sequence 5'-AGTGAA-3' in the center of the IE86 binding site. Approximately 50% protection is seen with 2 nM polyamide, and complete protection is obtained with 200 nM polyamide 1 (FIG. 30, lanes 3–5). Recombinant protein IE86 protects a region extending between positions −24 and +3. Approximately 250 nM IE86 is required to give complete protection (FIG. 30, lanes 6 and 14). When polyamide 1 is preincubated with DNA for 15 minutes prior to addition of protein, the IE86 footprint is partially replaced by the polyamide 1 specific footprint at a concentration of 2 nM polyamide, and is completely replaced at a concentration of 200 nM polyamide (FIG. 30, lanes 7–9). The control polyamide 5, which protects a site 5'-AGGTCT-3' immediately upstream of the TATA box, does not interfere with IE86 binding in a concentration range of 2–200 WM. Both the IE86-specific footprint and the polyamide 5 footprint coexist, even though they are only 9 base-pairs apart (FIG. 30, lanes 14–17). A singly-end labeled restriction fragment was used in DNase I footprinting reactions. Reactions contained approximately 250 nM his-tagged IE86 where indicated, and polyamide 1 in the concentrations indicated at the top of the lanes. Lanes 1 and 18 represent a G+A sequencing ladder. The extent of the footprints created by polyamide 1, IE86 and the control polyamide 5 are indicated by brackets alongside the autoradiogram. The location of the TATA box and the start of transcription are indicated.

Figure 31:
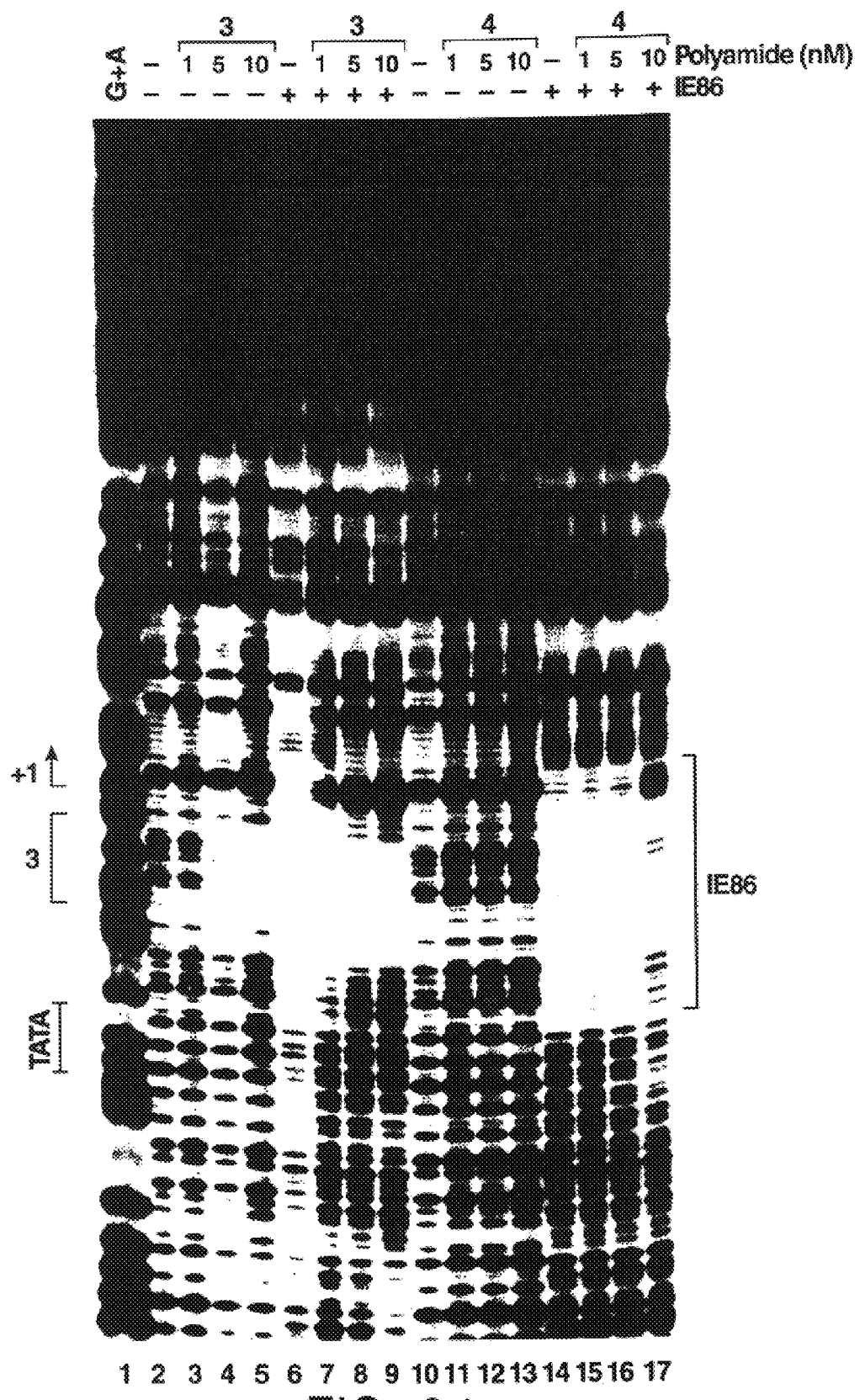
FIG. 31 is a representation of the results of a footprint experiment comparing the binding of polyamides 3 and 4 and IE86 to the repressor region of the CMV genome.

The same experiment was repeated with polyamides 2 and 3, which bind the same site 5'-AGTGAA-3' with higher affinities than polyamide 1. A complete protection is seen with 5 and 10 nM polyamide 3 (FIG. 31, lane 4), which are also the concentrations required to completely inhibit IE86 from binding (FIG. 31, lanes 8 and 9). A partial inhibition of IE86 binding is detected at 1 nM polyamide 3 (FIG. 31, lane 7). A similar result was obtained with polyamide 2 (data not shown). The mismatch polyamide 4 did not give a footprint on the CMV fragment in the concentration range used in these experiments (1–200 nM), and it did not interfere with IE86 binding (FIG. 31, lanes 11–13 and 15–17). The IE86 concentration was approximately 250 nM. The concentrations of the polyamide are indicated in nM at the top of the lanes. The extent of the footprints for polyamide 3 and IE86 protein as well as the TATA box and transcription start site are shown at the side of the autoradiogram.

The effects of the polyamides on MIEP transcription were tested in an in vitro system consisting of a cell-free extract prepared from cultured human CEM cells. It is known from previous studies that E86 inhibits transcription by binding to the cis repression sequence, and physically blocks the access of RNA polymerase II to the preinitiation complex. Whether polyamide 1, which has a relatively low binding affinity (in about the same range as IE86), could counteract the negative effect of IE86 on transcription was tested. Run-off transcription reactions were performed with linearized plasmid and CEM extract. The concentration of IE86 that was needed to give approximately 75% inhibition of transcription was empirically determined. The polyamides were added at a concentration of 1 $\mu$M.

Figure 32:
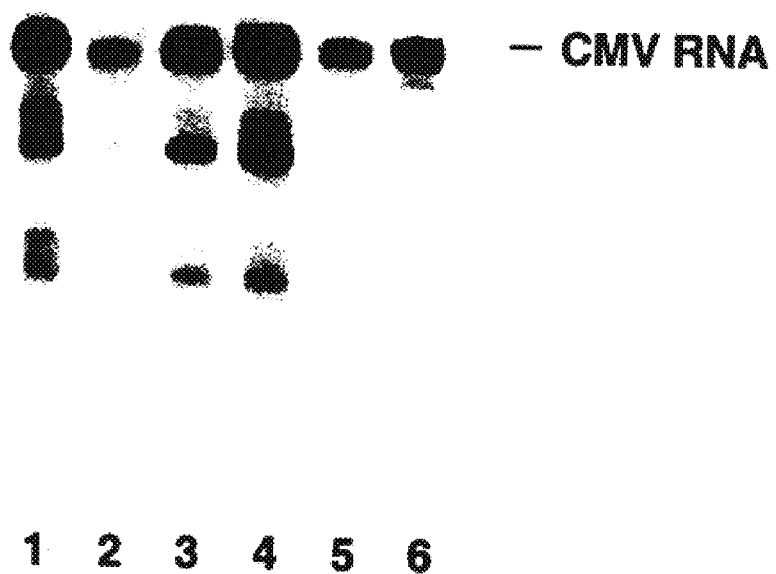
FIG. 32 is a representation of the results of an experiment comparing the binding of polyamide 1 and IE86 on the transcription of CMV RNA.

FIG. 32 shows that IE86 inhibits CMV transcription by approximately 75% (lane 2). When polyamide 1 is preincubated with DNA prior to addition of IE86 protein, the level of transcription is restored to approximately 75% of the control (FIG. 32, lane 3). Interestingly, the presence of polyamide 1 bound to the crs in the absence of IE86, has no effect on transcription, even at a concentration of 1 $\mu$M (FIG. 32, lane 4). An unrelated polyamide, which has no binding site in the CMV promoter, has no effect on IE86-mediated repression, even at a concentration of 1 $\mu$M (FIG. 32, lane 5). Thus, polyamide 1 is able to specifically counteract transcriptional repression mediated by IE86 protein.

The foregoing is intended to be illustrative of the present invention, but not limiting. Numerous variations and modifications of the present invention may be effected without departing from the true spirit and scope of the invention.

We claim:

1. A method of inhibiting the replication of a pathogen by administering a transcription inhibiting amount of at least one polyamide compound having the form $$X_1X_2 \ldots X_m\text{-}\gamma\text{-}X_{(m+1)} \ldots X_{(2m-1)}X_{2m}\text{-}\beta\text{-Dp}$$

wherein $X_1$, $X_2$, $X_mX_{(m+1)}$, $X_{(2m-1)}$, and $X_{2m}$ are carboxamide residues forming carboxamide binding pairs $X_1/X_{2m}$, $X_2/X_{(2m-1)}$, $X_m/X_{(m+1)}$, and $\gamma$ is $\gamma$-aminobutyric acid or 2,4-diaminobutyric acid, $\beta$ is $\beta$-alanine, and Dp is dimethylaminopropylamide, where m is an integer having a value from 3 to 6.

2. The method of claim 1 wherein the pathogen is chosen from the group consisting of viruses, bacteria, fungi and protozoans.

3. The method of claim 1 wherein the pathogen is a retrovirus.

4. The method of claim 1 wherein the pathogen is HIV-1.

5. A method of inhibiting the replication of a pathogen by administering a transcription inhibiting amount of at least one polyamide wherein the polyamide is chosen from the group consisting of ImPyPyPy-γ-ImPyPyPy-β-Dp, ImPy-β-ImPy-γ-ImPy-β-ImPy-β-Dp, ImPy-β-PyPyPyPy-β-ImPy-β-Dp, ImPy-β-ImPy-β-PyPyPyPy-β-ImPy-β-ImPy-β-Dp, ImPy-β-ImPyPyPy-β-ImPyPyPy-β-PyPy-β-Dp, ImImPyPy-γ-ImPyPyPy-β-Dp, and mixtures thereof wherein Im is N-methylimidazole, Py is N-methylpyrrole, γ is γ-aminobutyric acid, β is β-alanine, and Dp is dimethylaminopropylamide.

6. A method of treating a human patient with an HIV-1 infection comprising the step of administering a composition comprising a transcription inhibiting amount of at least one polyamide chosen from the group consisting of ImPyPyPy-γ-ImPyPy-β-Dp, ImPy-β-ImPy-γ-ImPy-β-ImPy-β-Dp and mixtures thereof and a pharmaceutically acceptable excipient.

7. A method of treating HIV-1 infected human- blood cells in vitro comprising the step of administering a composition comprising a transcription inhibiting amount of at least one polyamide chosen from the group consisting of ImPyPyPy-γ-ImPyPy-β-Dp, ImPy-β-ImPy-γ-ImPy-β-ImPy-β-Dp and mixtures thereof.

* * * * *